United States Patent [19]

Branca et al.

[11] Patent Number: 5,688,946
[45] Date of Patent: *Nov. 18, 1997

[54] AMINO ACID DERIVATIVES HAVING RENIN INHIBITING ACTIVITY

[75] Inventors: Quirico Branca, Basel, Switzerland; Werner Neidhart, Freiburg im Breisgau, Germany; Henri Ramuz, Birsfelden; Heinz Stadler, Rheinfelden, both of Switzerland; Wolfgang Wostl, Grenzach-Wyhlen, Germany

[73] Assignee: Hoffmann La Roche Inc., Nutley, N.J.

[*] Notice: The term of this patent shall not extend beyond the expiration date of Pat. No. 5,134,123.

[21] Appl. No.: 277,111

[22] Filed: Jul. 19, 1994

Related U.S. Application Data

[63] Continuation of Ser. No. 571,689, Aug. 23, 1990, abandoned.

[30] Foreign Application Priority Data

| Sep. 4, 1989 | [CH] | Switzerland | 3192/89 |
| Jul. 12, 1990 | [CH] | Switzerland | 2336/90 |

[51] Int. Cl.[6] .............. C07D 295/12; C07D 295/22; A61K 31/95; A61K 37/00
[52] U.S. Cl. .............. 544/242; 514/326; 514/397; 514/380; 514/399; 514/400; 514/616; 514/18; 514/19; 514/394; 514/231.5; 546/138; 548/215; 548/338.1; 548/339.1; 548/306.1
[58] Field of Search .............. 514/400, 616, 514/231.5, 326, 397, 380; 548/339.1, 215, 338.1, 306.1; 544/242; 546/138; 549/74, 491

[56] References Cited

U.S. PATENT DOCUMENTS

| 4,652,551 | 3/1987 | Luly et al. | 514/18 |
| 4,845,079 | 7/1989 | Luly et al. | 514/18 |
| 5,032,577 | 7/1991 | Fung et al. | 514/18 |
| 5,134,123 | 7/1992 | Branca et al. | 514/18 |

FOREIGN PATENT DOCUMENTS

| 0230266 | 7/1987 | European Pat. Off. | 514/18 |
| 0309766 | 4/1989 | European Pat. Off. | 514/18 |
| 0313847 | 5/1989 | European Pat. Off. | 514/18 |
| WO87/04348 | 7/1987 | WIPO | 514/18 |
| WO87/04349 | 7/1987 | WIPO | 514/18 |
| WO88/05050 | 7/1988 | WIPO | 514/18 |

OTHER PUBLICATIONS

Burger, A. Medicinal Chemistry, 2nd Ed., pp. 565–571, 578–81, 600–601 (1960).
Denkewalter et al., Progress in Drug Research, vol. 10, pp. 510–512 (1966).
Bolis et al., J. Med. Chem, vol. 30, pp. 1729–1737 (1987).
Haber et al., J. Cardiovascular Pharmacology, vol. 10 (Supp. 7), S54–S58 (1987).
Plattner et al., J. Med. Chem., vol. 31, pp. 2277–2288 (1988).

*Primary Examiner*—Floyd D. Higel
*Attorney, Agent, or Firm*—George W. Johnston; Dennis P. Tramaloni; Bruce A. Pokras

[57] ABSTRACT

The compounds of the formula

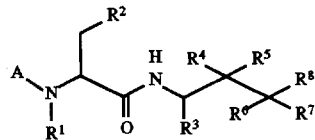

in the form of optically pure diastereomers, mixtures of diastereomers, diastereomeric racemates or mixtures of diastereomeric racemates as well as pharmaceutically usable salts thereof inhibit the activity of the natural enzyme renin and can accordingly be used in the form of pharmaceutical preparations in the control or prevention of high blood pressure and cardiac insufficiency.

20 Claims, No Drawings

AMINO ACID DERIVATIVES HAVING RENIN INHIBITING ACTIVITY

This is a continuation of application Ser. No. 07/571,689, filed Aug. 23, 1990 now abandoned.

SUMMARY OF THE INVENTION

The present invention is concerned with amino acid derivatives. In particular, it is concerned with amino acid derivatives of the general formula

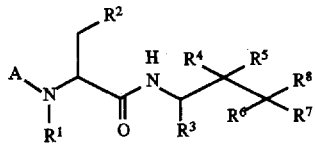   I wherein $R^1$ is hydrogen or methyl, $R^2$ is ethyl, propyl, isopropyl, thioalkyl, imidazol-2-yl, imidazol-4-yl, 5-iodoimidazol-4-yl, 5-cyanoimidazol-4-yl, N-methylimidazol-2-yl, N-methylimidazol-4-yl, C-methylated imidazol-2-yl, C-methylated imidazol-4-yl, N-substituted imidazol-2-yl, N-substituted imidazol-4-yl, pyrazol-3-yl, thiazol-4-yl, thien-2-yl, ethoxycarbonyl, aminocarbonyl, aminocarbonylmethyl, t-butoxycarbonylmethyl, benzyloxycarbonylmethyl or t-butoxy, $R^3$ is isobutyl, cyclohexylmethyl, substituted cyclohexylmethyl, cyclohexenylmethyl, cyclohexanonylmethyl, bicyclo[3.1.0]hexylmethyl, bicyclo[4.1.0]heptylmethyl, cycloalkylalkylthiomethyl, 1,3-dithiolan-2-ylmethyl, 1,3-dithian-2-ylmethyl, halobenzyl or benzyl, $R^4$ is hydrogen and $R^6$ is hydrogen or alkyl and $R^5$ and $R^7$ each independently are hydroxy, alkylcarbonyloxy optionally mono- or multiply-substituted by amino, monoalkylamino, dialkylamino, alkanoylamino, alkoxycarbonylamino, alkylcarbonyloxy, carboxy, alkoxy or hydroxy, or arylcarbonyloxy, arylalkylcarbonyloxy, cycloalkylcarbonyloxy, heteroarylalkylcarbonyloxy, the group —OSO$_3$H or —PO(OR)$_2$, wherein R is alkyl, or hydroxy which is protected with an O-protecting group, or $R^5$ is amino or amino substituted by a protecting group which is readily cleavable under physiological conditions and $R^7$ is hydroxy, amino, amino substituted by a protecting group which is readily cleavable under physiological conditions or azido or $R^5$ and $R^7$ together are hydroxy protected with a cyclic O-protecting group, or $R^4$ and $R^5$ together are an oxo group and $R^6$ is hydrogen or fluorine and $R^7$ is fluorine, or $R^4$ is hydrogen, $R^5$ is hydroxy, $R^6$ is hydrogen and $R^7$ is amino, amino substituted by a protecting group which is readily cleavable under physiological conditions, azido or fluorine or $R^6$ and $R^7$ each are fluorine or together are oximino or an oxo group, $R^8$ is hydroxymethyl, alkylhydroxymethyl, cycloalkylhydroxymethyl, cycloalkylaminomethyl, cycloalkylcarbonyl or one of the groups

 (a)

and

 (b)

or $R^7$ and $R^8$ together are 2-oxo-3-cycloalkyloxazolidin-5-yl and A is one of the groups

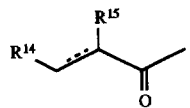 (c)

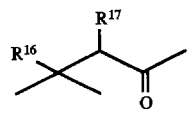 (d)

and

—(Y)$_n$Z, (e)

wherein D is a methyne group or a nitrogen atom, $R^9$ is alkyl, aryl or arylalkyl and $R^{10}$ is hydrogen, alkyl, aryl or arylalkyl or $R^9$ and $R^{10}$ together with the two atoms to which they are attached are aryl, heteroaryl, cycloalkenyl or heterocycloalkenyl, $R^{11}$ is hydrogen or alkyl and $R^{12}$ and $R^{13}$ each independently are alkyl, aryl, arylalkyl, cycloalkyl or the group —CH$_2$—X—R$^{18}$ (f)

or together with the carbon atom to which they are attached are cycloalkyl or heterocycloalkyl, with the proviso that, where $R^{11}$ is alkyl, $R^{12}$ and $R^{13}$ also are alkyl, the dotted line can be an additional bond, $R^{14}$ and $R^{16}$ each are phenyl, substituted phenyl, benzyl, naphthyl, cyclohexyl, thienyl or furyl and $R^{15}$ and $R^{17}$ each are hydrogen, alkoxycarbonylalkyl, alkylcarbonylalkyl, cycloalkylcarbonylalkyl, heterocycloalkylcarbonylalkyl, arylcarbonylalkyl, aminocarbonylalkyl, substituted aminocarbonylalkyl, alkoxycarbonylhydroxyalkyl, alkylcarbonylhydroxyalkyl, cycloalkylcarbonylhydroxyalkyl, heterocycloalkylcarbonylhydroxyalkyl, arylcarbonylhydroxyalkyl, aminocarbonylhydroxyalkyl, substituted aminocarbonylhydroxyalkyl, dialkoxyphosphoroxyalkyl, diphenyloxyphosphoroxyalkyl, arylalkyl, alkoxycarbonylamino, arylalkoxycarbonylamino, alkylthioalkyl, alkylsulphinylalkyl, alkylsulphonylalkyl, cycloalkylsulphonylalkyl, cycloalkylalkylsulphonylalkyl, substituted phenylsulphonylalkyl, substituted aminocarbonyloxy, aminoalkylcarbonylalkyl, substituted aminoalkylcarbonylalkyl, heterocycloalkylcarbonyloxy, guanidinium methylsulphonate, substituted aminoalkylsulphonylalkyl or substituted aminosulphonylalkyl, with the proviso that $R^{15}$ cannot be alkoxycarbonylamino or arylalkoxycarbonylamino when $R^{14}$ is phenyl, halophenyl, hydroxyphenyl, methoxyphenyl, benzyl, α-naphthyl, cyclohexyl, thienyl or furyl, Y is the bivalent residue of optionally N- and/or α-methylated phenylalanine, halophenylalanine, cyclohexylalanine, thienylalanine, furylalanine, pyridylalanine, tyrosine, O-methyltyrosine, α-naphthylalanine, homophenylalanine or 2-hydroxy-3-amino-4-phenylbutyric acid linked with Z at the N-terminal, Z is hydrogen, acyl or 1-azabicyclo[2.2.2]octan-3-yl, n is the number 0 or 1, X is an oxygen or sulphur atom or the group —NH— and $R^{18}$ is hydrogen, alkyl, cycloalkyl, arylalkyl, cycloalkylalkyl, alkylcarbonyl, arylcarbonyl or arylalkylcarbonyl, with the provisos that (i) where $R^4$ and $R^6$ each are hydrogen and $R^5$ and $R^7$ each independently are hydroxy, alkylcarbonyloxy optionally mono- or multiply-substituted by amino, monoalkylamino, dialkylamino, alkanoylamino, alkoxycarbonylamino, carboxy, alkoxy or hydroxy or an O-protecting group or together are a cyclic O-protecting group, then A is group (c) in which $R^{14}$ is cyclohexyl, thienyl or furyl and/or $R^{15}$ is cycloalkylsulphonylalkyl, cycloalkylalkylsulphonylalkyl, substituted phenylsulphonylalkyl, substituted aminocarbonyloxy-aminoalkylcarbonylalkyl, substituted aminocarbonylalkyl, substituted aminoalkylsulphonylalkyl or substituted aminosulphonylalkyl, group (d) or (e) in which n is the number 0 or Y is thienylalanine, furylalanine or pyridylalanine and/or Z is 1-azabicyclo [2.2.2]octan-3-yl and/or $R^2$ is thioalkyl, N-substituted imidazol-2-yl or N-substituted imidazol-4-yl and/or $R^3$ is cyclohexylmethyl, cyclohexenylmethyl, cyclohexanonylmethyl, bicyclo[3.1.0]-hexylmethyl, bicyclo[4.1.0]heptylmethyl, cycloalkylalkylthiomethyl, 1,3-dithiolan-2-ylmethyl or 1,3-dithian-2-ylmethyl and/or $R^8$ is hydroxymethyl, cycloalkylhydroxymethyl, cycloalkylaminomethyl or cycloalkylcarbonyl, (ii) where $R^4$ and $R^6$ are hydrogen, $R^5$ is amino and $R^7$ is hydroxy, amino or azido or is $R^4$ is hydrogen, $R^5$ is hydroxy, $R^6$ is hydrogen and $R^7$ is amino, azido or fluorine or $R^6$ and $R^7$ each are fluorine or together are an oxo group or $R^4$ and $R^5$ together are an oxo group and $R^6$ is hydrogen or fluorine and $R^7$ is fluorine, then $R^8$ is group (a) or (b), (iii) where $R^8$ is hydroxymethyl, alkylhydroxymethyl, cycloalkylhydroxymethyl, cycloalkylaminomethyl or cycloalkylcarbonyl, then $R^4$ and $R^6$ each are hydrogen and $R^5$ and $R^7$ each are hydroxy or, where $R^7$ and $R^8$ together are 2-oxo-3-cycloalkyloxazolidin- 5-yl, then $R^4$ and $R^6$ each are hydrogen and $R^5$ is hydroxy, and (iv) where $R^8$ is cycloalkylaminomethyl, then $R^{15}$ is different from alkylthioalkyl, alkylsulphinylalkyl, alkylsulphonylalkyl, substituted aminoalkylsulphonylalkyl or substituted aminosulphonylalkyl, in the form of optically pure diastereomers, mixtures of diastereomers, diastereomeric racemates or mixtures of diastereomeric racemates as well as pharmaceutically usable salts of these compounds.

These compounds are novel and are distinguished by valuable pharmacodynamic properties.

Objects of the present invention are the compounds of formula I and their pharmaceutically usable salts per se and for use as therapeutically active substances, the manufacture of these compounds, medicaments containing these and the manufacture of such medicaments, as well as the use of compounds of formula I and their pharmaceutically usable salts in the control or prevention of illnesses or in the improvement of health, especially in the control or prevention of high blood pressure and cardiac insufficiency.

DETAILED DESCRIPTION OF THE INVENTION

The following definitions of the general terms used in the present description apply irrespective of whether the terms in question appear alone or in combination.

The term "alkyl" used in the present description is straight-chain and branched, saturated hydro-carbon residues with 1–8, preferably 1–4, carbon atoms such as methyl, ethyl, n-propyl, isopropyl, n-butyl, isobutyl, sec.-butyl, t-butyl, pentyl, hexyl and the like. The term "alkoxy" is alkyl ether groups in which the term "alkyl" has the above significance, such as methoxy, ethoxy, propoxy, isopropoxy, butoxy, isobutoxy, sec.-butoxy, t-butoxy and the like. The term "cycloalkyl" is saturated, cyclic hydrocarbon residues with 3–8, preferably 3–6, carbon atoms such as cyclopropyl, cyclobutyl, cyclopentyl, cyclohexyl and the like. The term "alkanoyl" is the acid residue of a straight-chain or branched alkanoic acid with 1–8, preferably 1–4, carbon atoms such as formyl, acetyl, propionyl, butyryl, valeryl, isovaleryl and the like. The term "heterocycloalkyl" relates in a similar manner to saturated, 3–8-membered, preferably 5- or 6-membered, cyclic hydrocarbon residues in which one or two methylene groups is/are replaced by one or two oxygen, sulphur or optionally alkyl-, phenylalkyl-, alkylcarbonyl- or alkylcarbonyloxy-substituted nitrogen atoms, such as piperidinyl, pyrazinyl, N-benzylpyrazinyl, morpholinyl, N-methylpiperidinyl, N-benzylmorpholinyl and the like. The term "cycloalkenyl" relates to unsaturated cyclic hydrocarbon residues with 3–8, preferably 3–6, carbon atoms such as 1-cyclohexenyl, 1,4-cyclohexadienyl and the like. The term "heterocycloalkenyl" relates in a similar manner to unsaturated, 3–8-membered, preferably 5- or 6-membered, cyclic hydrocarbon residues in which one or two methylene groups is/are replaced by one or two oxygen, sulphur or optionally alkyl-, phenyl- alkyl-, alkylcarbonyl- or alkylcarbonyloxy-substituted nitrogen atoms, such as dihydropyranyl, dihydropyridyl, dihydrothienyl and the like. The term "aryl" denotes a mono- or bicyclic aromatic hydrocarbon residue with 6–14 carbon atoms which is optionally mono- or multiply-substituted by alkyl, alkoxy, alkylcarbonyloxy, amino, alkylamino, dialkylamino, alkylcarbonylamino, hydroxy, halogen, trifluoromethyl or nitro, such as phenyl, α- or β-naphthyl, indenyl, anthryl or phenanthryl and the like. The term "heteroaryl" denotes a mono- or bicyclic aromatic hydrocarbon residue in which one or more carbon atoms is/are replaced by one or two nitrogen atoms and/or an oxygen or sulphur atom and which is optionally substituted on a nitrogen atom by alkyl, phenyl or phenylalkyl and/or on one or more carbon atoms by alkyl, phenyl, phenylalkyl, halogen, hydroxy, alkoxy, phenylalkoxy or oxo and which can be partially saturated, such as pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl or a benz-fused cyclopenta-, cyclohexa- or cyclohepta-fused derivative thereof, e.g. 2- or 3-pyrrolyl, phenylpyrrolyl, e.g. 4- or 5-phenyl-2-pyrrolyl, 2-furyl, 2-thienyl, 2-imidazolyl, 2-, 3-, or 4-pyridyl, 2-, 3- or 5-indolyl, substituted 2-indolyl, for example 1-methyl-, 5-methyl-, 5-methoxy-, 5-benzyloxy-, 5-chloro or 4,5-dimethyl-2-indolyl, 1-benzyl-2-indolyl, 1-benzyl-3-indolyl, 4,5,6,7-tetrahydro-2-indolyl, cyclohepta[b]-5-pyrrolyl, 2-, 3- or 4-quinolyl, 4-hydroxy-2-quinolyl, 1-, 3- or 4-isoquinolyl, 1-oxo-1,2-dihydro-3-isoquinolyl, 2-quinoxalinyl, 2-benzofuranyl, 2-benzoxazolyl, 2-benzthiazolyl, benz[e]indol-2-yl, β-carbolin-3-yl and the like. The term "arylalkyl" denotes straight-chain or branched alkyl groups in which one or more hydrogen atoms is/are replaced by aryl groups, such as benzyl, diphenylmethyl, trityl, α- or β-naphthylmethyl, 2-phenylethyl, 3-phenyl-2-propyl, 4-phenyl-3-butyl, 2-(α- or β-naphthyl)ethyl, 3-α-naphthyl-2-propyl, 4-α-naphthyl-3-butyl and the like, whereby the aromatic residue can in each case be mono- or multiply-substituted as indicated above. The term "N-substituted imidazol-2-yl" or "N-substituted imidazol-4-yl" denotes corresponding imidazolyl residues which are substituted on one of the nitrogen atoms by alkoxycarbonyl, alkenyloxycarbonyl, arylalkoxycarbonyl, arylsulphonyl, alkylcarbonyloxyalkoxycarbonyl, alkylcarbonyloxyalkyl, alkoxycarbonylalkylidenealkyl, arylalkyl or 2,4-dinitrophenyl and the like, such as ethoxycarbonyl-, t-butoxycarbonyl-, allyloxycarbonyl-, benzyloxycarbonyl-, 9-fluorenylmethoxycarbonyl-, p-toluenesulphonyl, 1-methylcarbonyloxyethoxycarbonyl-, t-butylcarbonyloxymethyl, methoxycarbonylmethylideneethyl-, triphenylmethyl or 2,4-dinitrophenyl-substituted imidazol-2-yl. The term "substituted cyclohexylmethyl" denotes cyclohexylmethyl which is substituted by hydroxy or halogen, especially fluorine, and the like, such as 4-hydroxycyclohexylmethyl, 4-fluorocyclohexylmethyl, 4,4-difluorocyclohexylmethyl and the like. The term "substituted phenyl" denotes phenyl which is mono- or multiply-substituted by alkyl, alkoxy, alkoxycarbonyl, alkylcarbonyloxy, hydroxy, halogen or trifluoromethyl, such as 4-hydroxyphenyl, 4-methoxyphenyl, 4-methylphenyl, 4-chlorophenyl and the like. The term "substituted amino" is an amino group which is mono- or di-substituted by alkyl, arylalkyl, alkylcarbonyl, alkoxycarbonyl or arylalkoxycarbonyl or disubstituted by $C_3$-$C_6$-alkylene which is optionally interrupted by an oxygen, sulphur or optionally alkyl-, phenylalkyl-, alkylcarbonyl- or alkylcarbonyloxy-substituted nitrogen atom. The term "$C_3$-$C_6$-alkylene" denotes straight-chain or branched residues with 3–6 carbon atoms such as trimethylene, propylene, tetra- methylene, pentamethylene, hexamethylene and the like. The term "acyl" relates to the acyl group of a carboxylic acid, of an optionally N-substituted carbamic acid, of a sulphonic acid or of an optionally N-substituted amidosulphonic acid, especially those with the partial formulae $R^a$—CO—, $(R^a)(R^a)N$—CO—, $R^a$—$SO_2$—, or $(R^a)(R^a)N$—$SO_2$— in which $R^a$ is hydrogen, an unsubstituted or substituted, saturated aliphatic, cycloaliphatic, cycloaliphatic-aliphatic hydrocarbon residue with up to 10, preferably 6, carbon atoms which is optionally functionalized with hydroxy and/or amino, monoalkylamino. dialkylamino, alkanoylamino, alkoxycarbonylamino, arylalkoxycarbonylamino or substituted aminocarbonyl, an unsubstituted or substituted aromatic, heteroaromatic, aromatic-aliphatic or heteroaromatic-aliphatic hydrocarbon residue with up to 18, preferably 10, carbon atoms which is optionally functionalized with hydroxy and/or amino, monoalkylamino, dialkylamino, alkanoylamino, alkoxycarbonylamino, arylalkoxycarbonylamino or substituted aminocarbonyl, or an unsubstituted or substituted, saturated 5- or 6-membered heterocycle. The term "acyl" also relates to a monovalent residue of an amino acid linked via the α- or, when present, ω-carboxyl group. The term "O-protecting group" is a protecting group which is cleavable with base or preferably with acid, such as the tetrahydropyranyl or methoxymethyl residue, an alkylcarbonyloxymethyl or alkoxycarbonyloxymethyl residue and the like. Examples of "cyclic O-protecting groups" are acetals, ketals and cyclic esters such as the ketal of acetone, the acetal of pivalic aldehyde or benzaldehyde or the cyclic carbonate. The term "amino substituted by a protecting group which is readily cleavable under physiological conditions" is formylamino, alkylcarbonylamino such as acetylamino or pivaloylamino, hydroxyalkylcarbonylamino such as hydroxyacetamino, aminoalkylcarbonylamino such as aminoacetylamino, arylcarbonylamino such as benzoylamino, alkoxycarbonylamino such as methoxy or tert.butoxycarbonylamino, arylalkoxycarbonylamino such as benzyloxycarbonylamino, arylmethylamino such as diphenylmethylamino or tritylamino and the like.

An unsubstituted or substituted, saturated, aliphatic, cycloaliphatic or cycloaliphatic-aliphatic hydrocarbon residue $R^a$ is, for example, unsubstituted or substituted alkyl, mono-, bi- or tricycloalkyl or cycloalkylalkyl. "Substituted alkyl" is an alkyl residue in which one or more hydrogen atoms can be replaced by hydroxy, alkoxy, alkylcarbonyloxy, halogen, amino or oxo, whereby the substituents are present in the 1-position of the alkyl residue only when this is present in the partial formula

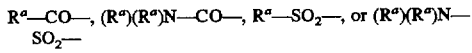

Examples of substituted alkyl are 2-hydroxyethyl, methoxymethyl, 2-methoxyethyl, acetoxymethyl, 2-acetoxyethyl, chloromethyl, bromomethyl, 2-chloro- or 2-bromoethyl, 2-oxopropyl, 2-oxobutyl.

The term "bicycloalkyl" relates to bicyclic saturated hydrocarbon residues with 5–10, preferably 6–9, carbon atoms such as bicyclo-[3.1.0]hex-1-yl, bicyclo[3.1.0]hex-2-yl, bicyclo[3.1.0]hex-3-yl, bicyclo[4.1.0]hept-1-yl, bicyclo[4.1.0]hept-4-yl, bicyclo[2.2.1]hept-2-yl, bicyclo[3.2.1]oct-2-yl, bicyclo[3.3.0]oct-3-yl, bicyclo[3.3.1]-non-9-yl, α- or β-decahydronaphthyl and the like.

The term "tricycloalkyl" relates to a tricyclic saturated hydrocarbon residue with 8–10 carbon atoms such as 1-adamantyl.

Cyclopropylmethyl, cyclobutylmethyl, cyclopentylmethyl, cyclohexylmethyl and the like are examples of cycloalkylalkyl.

The mentioned cycloaliphatic and cycloaliphatic-aliphatic residues can be substituted by the same substituents as alkyl.

An optionally substituted aromatic or aromatic-aliphatic hydrocarbon residue is, for example, unsubstituted or substituted aryl or arylalkyl.

In a heteroaromatic or heteroaromatic-aliphatic hydrocarbon residue the heterocycle is mono-, bi- or tricyclic and contains one to two nitrogen atoms and/or an oxygen or sulphur atom and is linked with the group —CO—, >N—CO—, —$SO_2$ or >N—$SO_2$— via one of its ring carbon atoms. Examples of such heteroaromatic hydrocarbon residues are pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl or a benzfused cyclopenta-, cyclohexa- or cyclohepta-fused derivative of these residues. The heteroaromatic residue can be substituted on a nitrogen atom by alkyl, phenyl or phenylalkyl, e.g. benzyl, and/or on one or more carbon atoms by alkyl, phenyl, phenylalkyl, halogen, hydroxy, alkoxy, phenylalkoxy or oxo and can be partially saturated. Examples of such heteroaromatic residues are 2- or 3-pyrrolyl, phenylpyrrolyl, e.g. 4- or 5-phenyl-2-pyrrolyl, 2-furyl, 2-thienyl, 2-imidazolyl, 2-, 3- or 4-pyridyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2-indolyl, 1-benzyl-3-indolyl, 4,5,6,7-tetrahydro-2-indolyl, cyclohepta[b]-5-pyrrolyl, 2-, 3- or 4-quinolyl, 4-hydroxy-2-quinolyl, 1-, 3- or 4-isoquinolyl, 1-oxo-1,2-dihydro-3-isoquinolyl, 2-quinoxalinyl, 2-benzofuranyl, 2-benzoxazolyl, 2-benzthiazolyl, benz[e]indol-2-yl, β-carbolin-3-yl and the like.

Examples of heteroaromatic-aliphatic hydrocarbon residues are 2- or 3-pyrrolylmethyl, 2-, 3- or 4-pyridylmethyl, 2-(2-, 3- or 4-pyridyl)ethyl, 4-imidazolylmethyl, 2-(4-imidazolyl)ethyl, 2-indolylmethyl, 3-indolylmethyl, 2-(3-indolyl)ethyl, 2-quinolylmethyl and the like.

A saturated 5- or 6-membered heterocyclic residue has at least one carbon atom, 1–3 nitrogen atoms and/or 1–2 oxygen and/or sulphur atoms as the ring members and is linked with the group —CO—, >N—CO—, —SO$_2$— or >N—SO$_2$— via one of its ring carbon atoms. The heterocycle can be substituted on one of its carbon atoms or on a ring nitrogen atom by alkyl, e.g. methyl or ethyl, phenyl or phenylalkyl, e.g. benzyl, or on one of its carbon atoms by hydroxy or oxo and/or can be benz-fused on two adjacent carbon atoms. Examples of such heterocyclic residues are pyrrolidin-3-yl, 4-hydroxypyrrolidin-2-yl, 5-oxopyrrolidin-2-yl, piperidin-2-yl, piperidin-3-yl, 1-methylpiperidin-2-yl, 1-methylpiperidin-3-yl, 1-methylpiperidin-4-yl, morpholin-2-yl, morpholin-3-yl, thiomorpholin-2-yl, thiomorpholin-3-yl, 1,4-dimethylpiperazin-2-yl, 2-indolinyl, 3-indolinyl, 1,2,3,4-tetrahydroquinol-2-, -3- or -4-yl, 1,2,3,4-tetrahydroisoquinol-1-, -3- or -4-yl, 1-oxo-1,2,3,4-tetrahydroisoquinol-3-yl and the like.

As residues of an amino acid linked via the α- or, when present, ω-carboxyl group there come into consideration mono- and dibasic α- and β-amino acids having the L- or D-configuration, which are optionally alkylated in the u-position and/or amino-alkylated at the N-atom and whose amino group(s) and/or second carboxyl group are optionally protected. Suitable protecting groups are in both cases those which are usual in peptide chemistry, such as tert-butoxycarbonyl, benzyloxycarbonyl, tert-butyl ester, benzyl ester and the like. Furthermore, when a second carboxyl group is present, this can be intramolecularly amidated. Examples of such amino acids are proline, pyroglutamic acid, aminobutyric acid, aminoethylglycine, aminoethylaspartic acid ester and the like.

The term "pharmaceutically usable salts" embraces salts with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like or, where $R^5$ and/or $R^7$ are the group —OSO$_3$H, also with inorganic or organic bases such as sodium or potassium hydroxide, ammonia, triethylamine, diisopropylethylamine, pyridine and the like. Such salts can be manufactured readily by any person skilled in the art having regard to the state of the art and taking into consideration the nature of the compound to be converted into a salt.

The compounds of formula I have at least three asymmetric carbon atoms and are therefore present in the form of optically pure diastereomers, mixtures of diastereomers, diastereomeric racemates or mixtures of diastereomeric racemates. The present invention embraces all forms. Mixtures of diastereomers, diastereomeric racemates or mixtures of diastereomeric racemates can be separated according to usual methods, e.g. by column chromatography, thin-layer chromatography, HPLC and the like.

A special group of compounds of formula I comprises those in which $R^2$ is other than thioalkyl, aminocarbonyl and aminocarbonylmethyl, $R^3$ is other than cycloalkylalkylthiomethyl, $R^{15}$ and $R^{17}$ are each other than cycloalkylsulphonylalkyl, cycloalkylalkylsulphonylalkyl, substituted phenylsulphonylalkyl and aminoalkylcarbonylalkyl, Y is other than pyridylalanine and Z is other than 1-azabicyclo[2.2.2]octan-3-yl.

Those compounds of formula I in which $R^1$ is hydrogen are preferred. $R^2$ preferably is imidazol-2-yl, imidazol-4-yl, thiazol-4-yl, aminocarbonyl or aminocarbonylmethyl, particularly imidazol-4-yl. Further, those compounds of formula I in which $R^3$ is cyclohexylmethyl, substituted cyclohexylmethyl or cyclohexenylmethyl, particularly cyclohexylmethyl or 4,4-difluorocyclohexylmethyl, are preferred. $R^4$ and $R^6$ each preferably are hydrogen. $R^5$ preferably is hydroxy, amino or alkylcarbonyloxy monosubstituted by amino, particularly hydroxy or aminomethylcarbonyloxy. Further, those compounds of formula I in which $R^7$ is hydroxy, amino, alkylcarbonyloxy monosubstituted by amino, azido or fluorine, particularly hydroxy or aminomethylcarbonyloxy, are also preferred. Also preferred are those compounds of formula I in which $R^8$ is alkylhydroxymethyl, cycloalkylhydroxymethyl or group (b), particularly group (b). Likewise preferred are the compounds of formula I in which $R^7$ and $R^8$ together are 2-oxo-3-cycloalkyl-oxazolidin-5-yl. Furthermore, those compounds of formula I in which A is group (c) or (e), particularly group (c), are also preferred. Hydrogen is the preferred significance for $R^{11}$. Preferably, $R^{12}$ and $R^{13}$ each are alkyl or together with the carbon atom to which they are attached are cycloalkyl, particularly cyclopropyl or cyclobutyl. $R^{14}$ preferably is phenyl or substituted phenyl, particularly phenyl. The preferred significance of $R^{15}$ is alkylcarbonylalkyl, heterocycloalkylcarbonylalkyl, substituted aminocarbonylalkyl, alkylsulphonylalkyl, cycloalkylsulphonylalkyl, cycloalkylalkylsulphonylalkyl, substituted aminoalkylcarbonylalkyl, heterocycloalkylcarbonyloxy, aminoalkylsulphonylalkyl or substituted aminosulphonylalkyl, preferably $C_1$–$C_4$-alkylcarbonylmethyl, heterocycloalkylcarbonylmethyl, substituted aminocarbonylmethyl, $C_1$–$C_4$-alkylsulphonylmethyl, $C_3$–$C_6$-cycloalkylsulphonylmethyl, $C_3$–$C_6$-cycloalkyl-$C_1$–$C_4$-alkylsulphonylmethyl, substituted amino-$C_1$–$C_4$-alkylcarbonylmethyl, heterocycloalkylcarbonyloxy, amino-$C_1$–$C_4$-alkylsulphonylmethyl or substituted amino-$C_1$–$C_4$-alkylsulphonylmethyl. Where A is group (e), then there are preferred those compounds of formula I in which Y is the bivalent residue of phenylalanine or O-methyltyrosine linked with Z at the N-terminal. Z preferably is the group $R^a$—CO— in which $R^a$ is an unsubstituted or substituted, saturated aliphatic hydrocarbon residue with up to 10 carbon atoms which is optionally functionalized with hydroxy and/or amino, monoalkylamino, dialkylamino, alkanoylamino, alkoxycarbonylamino, arylalkoxycarbonylamino or substituted aminocarbonyl or an unsubstituted or substituted heteroaromatic hydrocarbon residue with up to 18 carbon atoms, particularly the group $R^a$—CO— in which $R^a$ is a saturated, aliphatic hydrocarbon residue with up to 6 carbon atoms which is optionally functionalized with hydroxy and/or amino, alkanoylamino, alkoxycarbonylamino, aryloxycarbonylamino or substituted aminocarbonyl or a heteroaromatic residue with up to 10 carbon atoms which is optionally substituted by alkyl, halogen, hydroxy or alkoxy. A preferred significance of Z is also the monovalent residue of proline, pyroglutamic acid, α-methylalanine, aminoethylglycine, D-alanine, β-alanine or β,β-dimethylalanine linked via the carboxyl group.

From the above it follows that there are particularly preferred those compounds of formula I in which A, $R^1$, $R^2$, $R^3$, $R^4$, $R^5$, $R^6$, $R^7$ and $R^8$ have the preferred significances given above, especially those in which $R^1$ is hydrogen, $R^2$ is imidazol-4-yl, $R^3$ is cyclohexylmethyl or 4,4-difluorocyclohexylmethyl, $R^4$ and $R^6$ each are hydrogen, $R^5$ and $R^7$ each are hydroxy or aminomethylcarbonyloxy. $R^8$ is group (b), $R^{11}$ is hydrogen, $R^{12}$ and $R^{13}$ together with the carbon atom to which they are attached are cyclopropyl or cyclobutyl, $R^{14}$ is phenyl and $R^{15}$ is $C_1$–$C_4$-alkylcarbonylmethyl, heterocycloalkylcarbonylmethyl, substituted aminocarbonylmethyl, $C_1$–$C_4$-alkylsulphonylmethyl, $C_3$–$C_6$-cycloalkylsulphonylmethyl, $C_3$–$C_6$-cycloalkyl-$C_1$–$C_4$-alkylsulphonylmethyl, substituted amino-$C_1$-$C_4$-alkylcarbonylmethyl, heterocycloalkylcarbonyloxy, amino-$C_1$-$C_4$-alkylsulphonylmethyl or substituted amino-$C_1$-$C_4$-alkylsulphonylmethyl Especially preferred compounds of formula I are:

(S)-α-[(S)-α-[[(2-Amino-1,1-dimethylethyl)sulphonyl]methyl]hydrocinnamamido]-N-[(1S,2R,3S)-1-(cyclohexylmethyl)-3-cyclopropyl-2,3-dihydroxypropyl]imidazole-4-propionamide dihydrochloride, (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]-5-cyanoimidazole-4-propionamide, (S)-α-[(S)-α-[(tert-butylsulphonyl)methyl]hydrocinnamamido]-N-[(1S,2R,3S)-3-cyclopropyl-1-[(4,4-difluorocyclohexyl)methyl]-2,3-dihydroxypropyl]imidazole-4-propionamide, (S)-α-[(S)-α-[(tert-butylsulphonyl)methyl]hydrocinnamamido]-N-[(1S,2R,3S)-3-cyclopropyl-1-(p-fluorobenzyl)-2,3-dihydroxypropyl]imidazole-4-propionamide and (S)-α-[(S)-α-[[(2-amino-2-methylpropyl)sulphonyl]methyl]hydrocinnamamido]-N-[(1S,2R,3S)-1-(cyclohexylmethyl)-3-cyclopropyl-2,3-dihydroxypropyl]imidazole-4-propionamide diacetate.

Further specially preferred compounds of formula I are:

(S)-N-[(1S,2R,3S)-3-Azido-1-(cyclohexylmethyl)-3-cyclopropyl-2-hydroxypropyl]-α-[(S)-α-(tert-butylsulphonyl)methyl]hydrocinnamamido]imidazole-4-propionamide, (S)-α-[(S)-α-[(tert-butylsulphonyl)methyl]hydrocinnamamido]-N-[(1S,2R)-1-(cyclohexylmethyl)-2-[(R or S)-3-cyclopropyl-2-oxo-5-oxazolidinyl]-2-hydroxyethyl]-imidazole-4-propionamide, (S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl 1-piperidinecarboxylate, (S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl 4-morpholinecarboxylate, tert.butyl (R)-2-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl]carbamoyl]-1-pyrrolidinecarboxylate, (S)-α-[(S)-α-[(tert-butylsulphonyl)methyl]hydrocinnamamido]-N-[(1S,2R,3S)-1-(cyclohexylmethyl)-3-cyclopropyl-3-fluoro-2-hydroxypropyl]imidazole-4-propionamide, tert-butyl [1-[(S)-α-[[(S)-1-[[(1S,2R,3S)-1-(cyclohexylmethyl)-3-cyclopropyl-2,3-dihydropropyl]carbamoyl]-2-imidazol-4-ylethyl]carbamoyl]phenethyl]carbamoyl]-1-methylethyl]carbamate, di-tert-butyl N-[(S)-1-(tert-butoxycarbonyl)-2-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl]carbamoyl]ethyl]ethylenedicarbamate, (S)-α-[(S)-α-[(tert-butylsulphonyl)methyl]hydrocinnamamido]-N-[(1S,2R,3RS)-1-(cyclohexylmethyl)-2,3,4-trihydroxybutyl]imidazole-4-propionamide, (S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropanesulphonic acid guanidine salt, di-tert-butyl N-[[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl]carbamoyl]methyl]ethylenedicarbamate, N-[(S)-1-[[(1S,2R,3S)-1-(cyclohexylmethyl)-3-cyclopropyl-2,3-dihydroxypropyl]carbamoyl]-2-imidazol-4-ylethyl]indole-2-carboxamide, (S)-N-[(1S,2R,3S)-1-(cyclohexylmethyl)-3-cyclopropyl-2,3-dihydroxypropyl]-α-(2,2-dibenzylacetamido)imidazole-4-propionamide, (S)-α-[(S)-α-[2-[(2-aminoethyl)amino]acetamido]hydrocinnamamido]-N-[(1S,2R,3S)-1-(cyclohexylmethyl)-3-cyclopropyl-2,3-dihydroxypropyl]imidazole-4-propionamide, N-[(S)-1-[[(1S,2R,3S)-1-(cyclohexylmethyl)-3-cyclopropyl-2,3-dihydroxypropyl]carbamoyl]-2-imidazol-4-ylethyl]-2-benzimidazolecarboxamide and (S)-α-[(S)-α-[(tert-butylsulphonyl)methyl]hydrocinnamamido]-N-[(1S,2R,3R or S,4R or S)-1-(cyclohexylmethyl)-2,3,4-trihydroxyhexyl]imidazole-4-propionamide.

Compounds of formula I in the form of optically pure diastereomers, mixtures of diastereomers, diastereomeric racemates or mixtures of diastereomeric racemates as well as pharmaceutically usable salts thereof can be manufactured by:

a) reacting a compound of the general formula

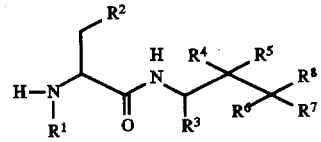

II wherein $R^1$, $R^2$, $R^3$, $R^4$, $R^5$, $R^6$, $R^7$ and $R^8$ have the significance given above, with an acylating agent yielding the group

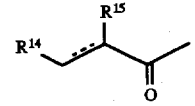 (c)

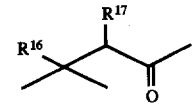 (d)

or

 (e)

wherein $R^{14}$, $R^{15}$, $R^{16}$, $R^{17}$ Y, Z n and the dotted line have the above significance, or b) reacting a compound of the general formula

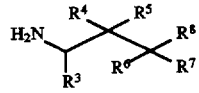

III wherein $R^3$, $R^4$, $R^5$, $R^6$, $R^7$ and $R^8$ have the significance given above, with a compound of the general formula

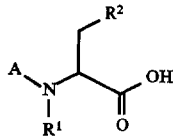

wherein $R^1$, $R^2$ and A have the significance given above, or an activated derivative thereof, or c) for the manufacture of a compound of formula I in which A is group (e) and Z is a monovalent residue of an amino acid linked via the carboxyl group and the remaining symbols have the significance given above, reacting a compound of formula I in which Z is hydrogen and the remaining symbols have the significance given above with an amino acid, or d) for the manufacture of a compound of formula I in which $R^5$ and/or $R^7$ are alkylcarbonyloxy optionally mono- or multiply-substituted by amino, monoalkylamino, dialkylamino, alkanoylamino, alkoxycarbonylamino, alkylcarbonyloxy, carboxy, alkoxy or hydroxy, or arylcarbonyloxy, arylalkylcarbonyloxy, cycloalkylcarbonyloxy, heteroarylalkylcarbonyloxy, the group —$OSO_3H$ or —$PO(OR)_2$, wherein R is alkyl, or hydroxy protected with an O-protecting group or amino substituted by a protecting group which is readily cleavable under physiological conditions or together are hydroxy protected with a cyclic O-protecting group and the remaining symbols have the significance given above, reacting a compound of formula I in which $R^5$ and/or $R^7$ are hydroxy or amino and the remaining symbols have the significance given above with an alkanoylating agent which is optionally mono- or multiply-substituted by amino, monoalkylamino, dialkylamino, alkanoylamino, alkoxycarbonylamino, alkylcarbonyloxy, carboxy, alkoxy or hydroxy or an aroylating, arylalkanoylating, cycloalkanoylating or heteroarylalkanoylating agent, a sulphating or phosphorylating agent or with an agent forming a N- and/or O-protecting group or a cyclic O-protecting group, or e) for the manufacture of a compound of formula I in which $R^2$ is N-substituted, optionally C-methylated imidazol-2-yl or N-substituted, optionally C-methylated imidazol-4-yl and the remaining symbols have the significance given above, reacting a compound of formula I in which $R^2$ is optionally C-methylated imidazol-2-yl or optionally C-methylated imidazol-4-yl and the remaining symbols have the significance given above with a suitable acylating, alkylating, arylalkylating or arylating agent, or f) for the manufacture of a compound of formula I in which A contains a free amino group and/or $R^2$ is imidazol-2-yl, imidazol-4-yl, C-methylated imidazol-2-yl, C-methylated imidazol-4-yl or pyrazol-3-yl and/or $R^5$ and/or $R^7$ are amino and/or $R^8$ contains a primary or secondary amino group, cleaving off the N-protecting group(s) from a compound of the general formula

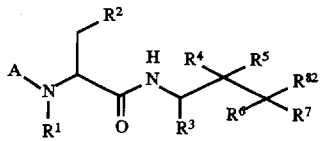

wherein $R^{82}$ has the same significance as $R^8$, but is in addition N-protected cycloalkylaminomethyl and the remaining symbols have the significance given above, with the proviso that at least one of A, $R^2$, $R^5$, $R^7$ and $R^{82}$ contains a N-protecting group, and g) if desired, separating a mixture of diastereomeric racemates into the diastereomeric racemates or optically pure diastereomers, and/or h) if desired, separating a mixture of diastereomers into the optically pure diastereomers, and/or i) if desired, converting a compound obtained into a pharmaceutically usable salt.

The acylation of a compound of formula II is effected according to methods known in the art. Especially suitable acylating agents are activated acid derivatives such as esters, mixed esters, acid halides and acid anhydrides or mixed anhydrides. The reaction is carried out in an organic solvent or solvent mixture which is inert under the reaction conditions at a temperature between about 0° C. and room temperature. As solvents there come into consideration especially aromatic hydrocarbons such as benzene, toluene or xylene, chlorinated hydrocarbons such as methylene chloride or chloroform, ethers such as diethyl ether, tetrahydrofuran or dioxan, and the like. When the acylating agent is a peptide, the reaction is effected under reaction conditions which are usual in peptide chemistry, i.e. preferably in the presence of a condensation agent such as HBTU (O-benzotriazolyl-N,N,N',N'-tetramethyluronium hexafluorophosphate), HOBTU (1,1,3,3-tetramethyl-2-[4-oxo-1,2,3-benzotriazin-3(4H)yl]uronium hexafluorophosphate), BOP (benzotriazol-1-yloxy-tris (dimethylamino)phosphonium hexafluorophosphate), BOPC (bis(2-oxo-2-oxozolidinyl)phosphine chloride), HOBT (N-hydroxybenzotriazole), HOOBT (3,4-dihydro-3-hydroxy-4-oxo-1,2,3-benzotriazine), DBU (1,8-diazabicyclo[5.4.0]undec-7-ene), DCC (dicyclohexylcarbodiimide), EDC (N-ethyl-N'(3-dimethylaminopropyl)carbodiimide hydrochloride), Hünig base (ethyldiisopropylamine), and the like. The reaction is conveniently carried out in an organic solvent or solvent mixture which is inert under the reaction conditions at a temperature between about 0° C. and 50° C. preferably at about room temperature. As solvents there come into consideration especially dimethylformamide, methylene chloride, acetonitrile, tetrahydrofuran, and the like.

The reaction of a compound of formula III with a compound of formula IV is also effected according to methods which are known in the peptide chemistry art, i.e. under the same conditions as have been given above for the reaction of a compound of formula II with a peptide. Examples of suitable activated derivatives of a compound of formula IV are acid halides, acid anhydrides, mixed anhydrides, esters, mixed esters, and the like.

The reaction of a compound of formula I in which Z is hydrogen with an amino acid in accordance with process variant c) is also effected according to methods which are known in the peptide chemistry art, i.e., under the conditions given above for the reaction of a compound of formula II with a peptide.

The reaction of a compound of formula I in which $R^5$ and/or $R^7$ are hydroxy or amino with an alkanoylating agent which is optionally mono- or multiply-substituted by amino, monoalkylamino, dialkylamino, alkanoylamino, alkoxycarbonylamino, alkylcarbonyloxy, carboxy, alkoxy or hydroxy or an aroylating, arylalkanoylating, cycloalkanoylating or heteroarylalkanoylating agent is also effected according to methods known in the art. Suitable acylating agents are acid anhydrides and acid halides, preferably acid chlorides. The reaction is effected in an organic solvent or solvent mixture which is inert under the reaction conditions, such as methylene chloride, dimethylformamide and the like, at a temperature between about room temperature and the reflux temperature of the reaction mixture, preferably at about room temperature. The reaction can be carried out in the presence or absence of an acid-binding agent such as sodium or potassium carbonate, pyridine, triethylamine and the like. The reaction with a sulphating or phosphorylating agent is likewise effected in a manner known in the art. Suitable sulphating agents are complexes of sulphur trioxide with an organic base such as the sulphur trioxide-dimethylformamide complex, the sulphur trioxide-triethylamine complex, the sulphur trioxide-ethyldiisopropylamine complex, the sulphur trioxide-pyridine complex and the like. The reaction is effected in an organic solvent which is inert under the reaction conditions, such as dimethylformamide and the like, at a temperature between about 0° and 50° C., conveniently at room temperature. Suitable phosphorylating agents are, for example, dialkyl chlorophosphate in pyridine, such as diethyl chlorophosphate in pyridine. Moreover, the reaction is effected at a temperature between about 0° and 50° C., preferably at room temperature. The reaction of a compound of formula I in which $R^5$ and/or $R^7$ are hydroxy or amino with an agent forming a N- and/or O-protecting group is also effected according to methods known in the art. Thus, for example, the tetrahydropyranyl ether can be manufactured by reaction with dihydropyran in the presence of an acid catalyst such as p-toluenesulphonic acid and the like and the acetone ketal can be manufactured by reaction with 2,2-dimethoxypropane in the presence of an acid catalyst such as p-toluenesulphonic acid. The reaction with an agent forming a N-protecting group depends on the nature of the agent which is used. Where the agent is an acylating agent, then the reaction is effected in an analogous manner to the O-acylation, i.e. with acid anhydrides, acid chlorides and the like under the same reaction conditions. On the other hand, the reaction with an arylmethylating agent, e.g. trityl chloride and the like, is carried out in the presence of an organic or inorganic base such as triethylamine, ethyldiisopropylamine, potassium carbonate and the like at a temperature between about 0° and 50° C., preferably at room temperature, in an organic solvent which is inert under the reaction conditions, such as methylene chloride, dimethylformamide, methanol and the like.

The N-substitution on the imidazole ring in accordance with process variant e) is also effected according to methods known in the art. Thus, for example, a compound of formula I in which $R^2$ is imidazol-2-yl, imidazol-4-yl, C-methylated imidazol-2-yl or imidazol-4-yl is reacted with a suitable acylating, alkylating, arylalkylating or arylating agent in the presence of an organic or inorganic base such as triethylamine, potassium carbonate and the like at a temperature between about 0° and 50° C., preferably at room temperature, in an organic solvent or solvent mixture which is inert under the reaction conditions, such as methylene chloride, dimethylformamide, or also methanol for the alkylation or arylalkylation, and the like. Examples of suitable acylating, alkylating, arylalkylating and arylating agents are acid halides such as e.g. allyl chloroformate, carbonates such as di-tert-butyl dicarbonate, halides such as trityl chloride and 2,4-dinitrofluorobenzene, and the like.

The cleavage of the N-protecting group(s) in accordance with process variant f) is also effected according to methods known in the art depending on the nature of the N-protecting group to be cleaved off. However, the cleavage is conveniently effected by acidic or basic hydrolysis. For the acidic hydrolysis there is advantageously used a solution of a mineral acid such as hydrochloric acid, hydrobromic acid, trifluoroacetic acid, sulphuric acid, phosphoric acid and the like in an inert solvent or solvent mixture. Suitable solvents are alcohols such as methanol or ethanol, ethers such as tetrahydrofuran or dioxan, chlorinated hydrocarbons such as methylene chloride, and the like. For the basic hydrolysis there can be used alkali metal hydroxides and carbonates such as potassium or sodium hydroxide or potassium or sodium carbonate, organic amines such as piperidine, and the like. Inert organic solvents such as have been named above for the acidic hydrolysis can be added as solubilizers. The reaction temperature for the acidic and basic hydrolysis can be varied in a range from about 0° C. to the reflux temperature, with the reaction preferably being carried out between about 0° C. and room temperature. The t-butoxycarbonyl residue is conveniently cleaved off with trifluoroacetic acid or formic acid in the presence or absence of an inert solvent. The Fmoc protecting group is conveniently cleaved off with piperidine at about room temperature. The benzyloxycarbonyl group can be cleaved off in a known manner by acidic hydrolysis as described above or hydrogenolytically.

The starting materials of formula II are partly novel and partly known. These compounds can be prepared by reacting a compound of formula III with a corresponding compound of formula IV in which, however, A is hydrogen. This reaction is also effected according to methods which are known in the peptide chemistry art, i.e. under the reaction conditions which are described above for the reaction of a compound of formula II with an acylating agent.

The starting materials of formula III are also partly novel and partly known. Thus, for example, those compounds of formula III in which $R^4$ and $R^6$ each are hydrogen and $R^5$ and $R^7$ each are hydroxy can be prepared by cleaving off the amino protecting group and, where applicable, simultaneously also the O-protecting group in a compound of the general formula

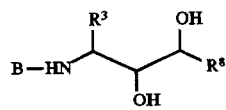

V or

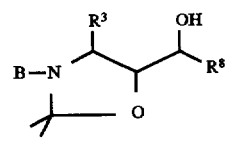

VI wherein B is an amino protecting group, preferably t-butoxycarbonyl or benzyloxycarbonyl, and $R^3$ and $R^8$ have the significance given above, or by treating a compound of the general formula

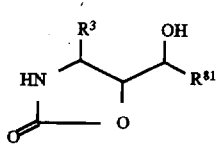

VII wherein $R^3$ has the significance given above and $R^{81}$ is group (a) or (b),
with a base.

The cleavage of the N-protecting group and, where applicable, the O-protecting group is also effected according to methods known in the art, for example in an organic solvent or solvent mixture which is inert under the reaction conditions at a temperature between about 0° C. and room temperature with an acid such as hydrochloric acid, trifluoroacetic acid, and the like. Suitable solvents are ethers such as tetrahydrofuran or dioxan, alcohols such as methanol or chlorinated hydrocarbons such as methylene chloride and the like. Under these reaction conditions the oxazolidine ring in a compound of formula VI is—as already mentioned—simultaneously cleaved. Of course, if only the cleavage of the oxazolidine ring is desired, then other reaction conditions must be chosen: the reaction must be carried out at low temperatures and in aqueous solvents or, for example, with iron trichloride/silica gel.

The reaction of a compound of formula VII with a base is also effected according to methods known in the art in a solvent or solvent mixture which is inert under the reaction conditions at a temperature between about room temperature and the reflux temperature. Suitable solvents are, for example, methanol, ethanol, dioxan, tetrahydrofuran, water or mixtures thereof. Sodium hydroxide, potassium hydroxide or barium hydroxide and the like come into consideration as bases.

The remaining compounds of formula III can be obtained in a manner analogous to the preparation of those compounds of formula III in which $R^4$ and $R^6$ each are hydrogen and $R^5$ and $R^7$ each are hydroxy. As starting materials there are used compounds corresponding to formulae V and VI in which $R^4$, $R^5$, $R^6$ and $R^7$ have the remaining possible significances. In Schemes I–III hereinafter there are presented by way of formulae various processes for the preparation of compounds of formulae V, VI and VII as well as the remaining starting materials required for the preparation of the compounds of formula III. Formulae V and VI do not appear in the Schemes: but formula Xa falls under formula V and formulae Xb, XV, XIX and XXII fall under formula VI. The symbols B, $R^3$ and $R^{81}$ used in the Schemes have the significance given above, while $R^{19}$ is alkyl or cycloalkyl, B' is an amino protecting group, P is an O-protecting group and Q is a leaving group such as alkylsulphonyl or arylsulphonyl, for example methylsulphonyl, trifluoromethylsulphonyl, p-toluenesulphonyl and the like.

The steps which are presented in Schemes I–III are without exception reactions which are usual in synthetic chemistry and which can also be carried out according to methods known in the art. With respect to the precise reaction conditions, reference is made to the experimental section. To complete the picture, it must be mentioned that certain reaction steps shown in Schemes I–III can also be carried out at a later stage of the synthesis, for example as the final step for the manufacture of the compounds of formula I, such as, for example, the oxazolidine ring closure in accordance with step XVII→XVI, the cleavage of an O-protecting group in accordance with step XXXIII→XXXIV or the oxime formation in accordance with step XLII→XLVI and the like. This, of course, only when the molecule contains no other groups which could thereby be affected.

The starting materials of formula IV are known or can be obtained in a manner analogous to the preparation of the known compounds.

Scheme I

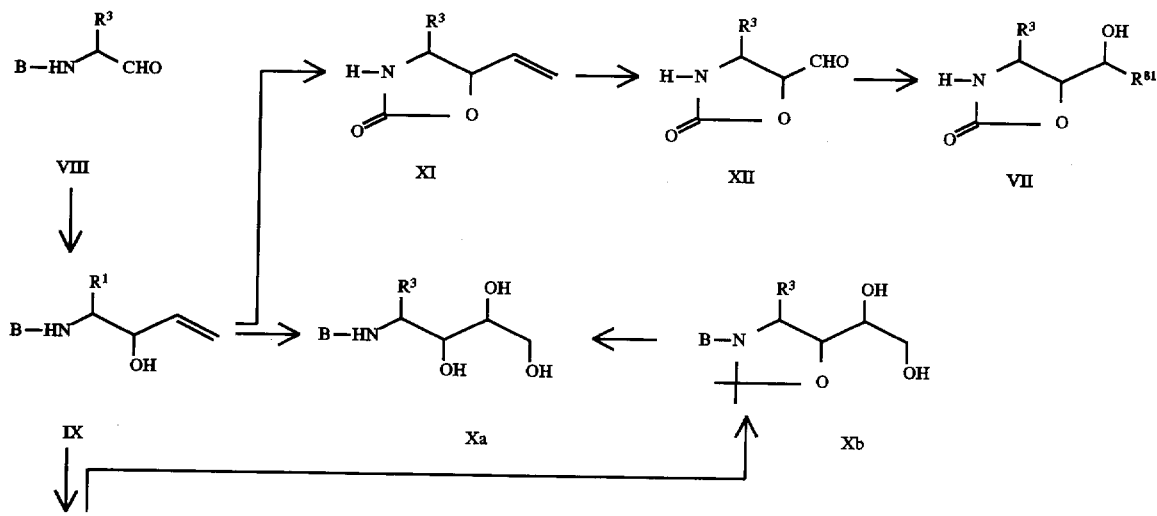

-continued
Scheme I
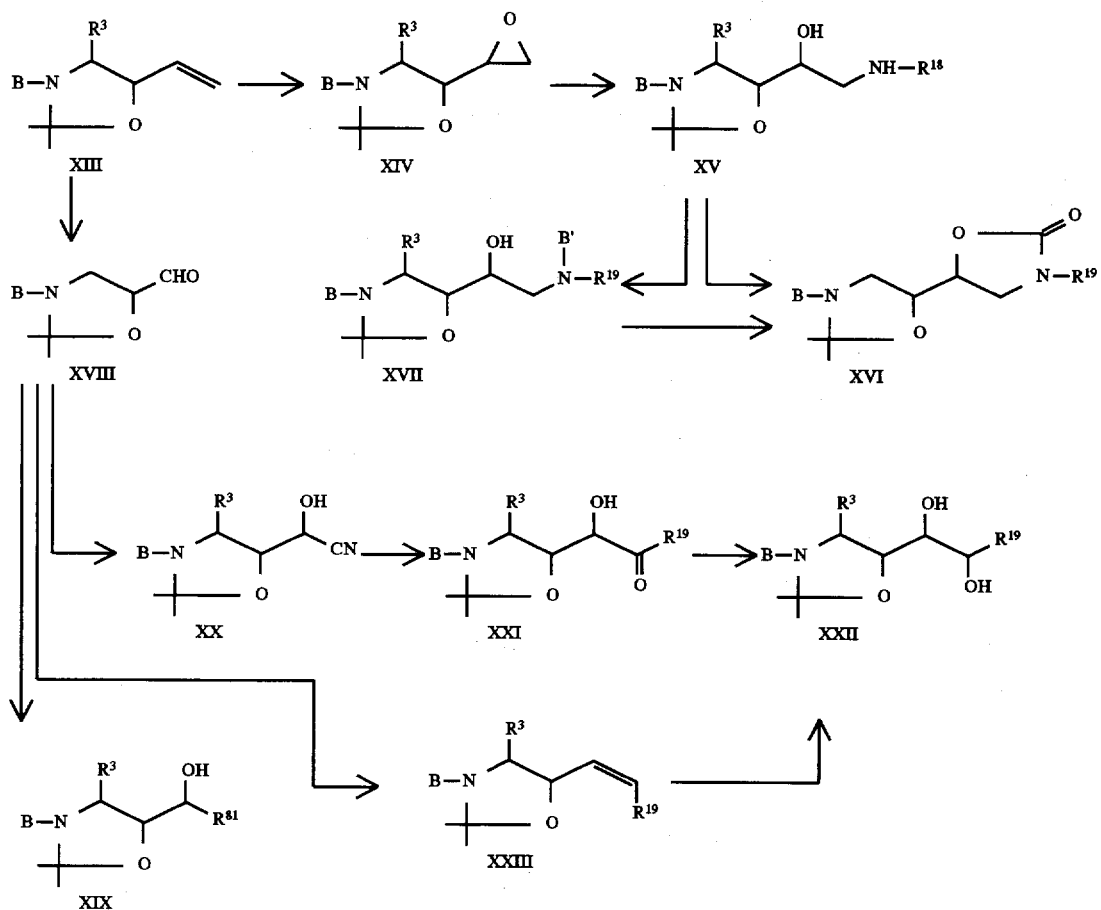
Scheme II
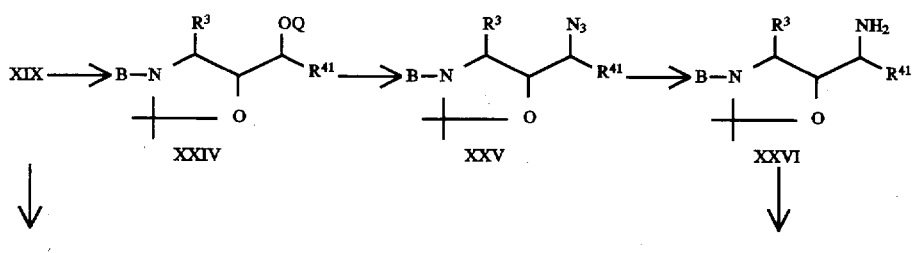

-continued
Scheme II
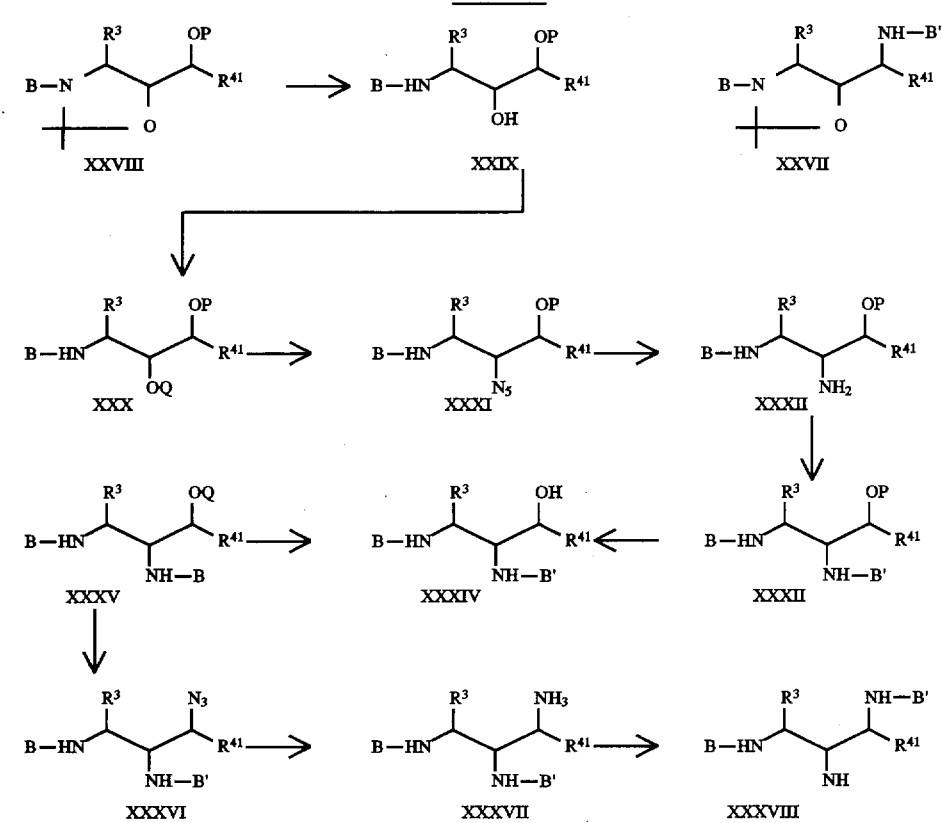
Scheme III
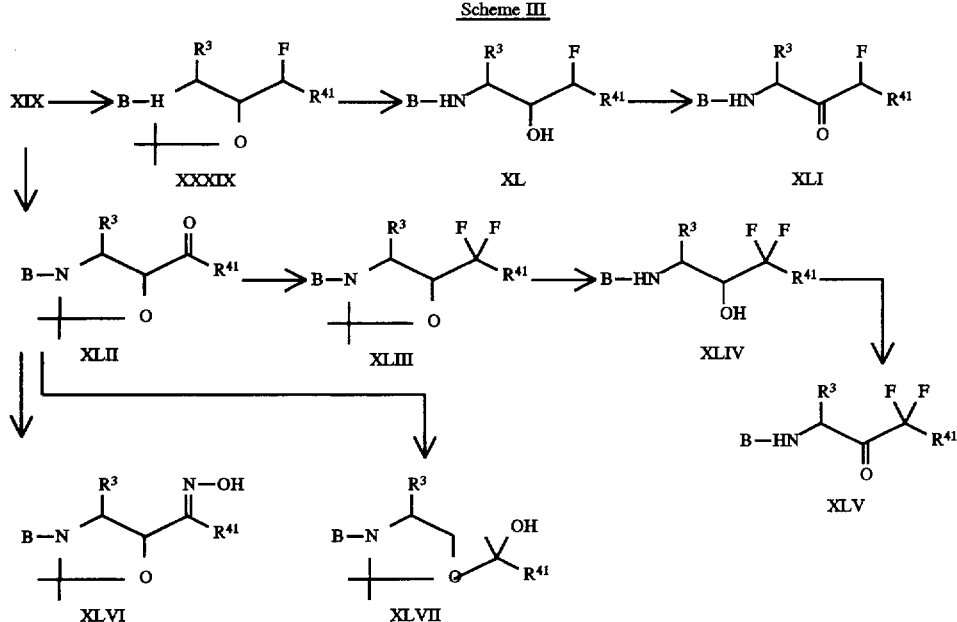
The still novel starting materials of formula II and III as well as of the formulae given in Schemes I–III are also objects of the present invention.
The compounds of formula I and their pharmaceutically usable salts have an inhibitory activity on the natural enzyme renin. The latter passes from the kidneys into the blood and there brings about the cleavage of angiotensinogen with the formation of the decapeptide angiotensin I which is then cleaved in the lungs, the kidneys and other organs to the octapeptide angiotensin II. Angiotensin II increases the blood pressure not only directly by arterial constriction, but also indirectly by the liberation of the sodium ion-retaining hormone aldosterone from the adrenal gland, with which is associated an increase in the extracellular fluid volume. This increase is attributed to the action of angiotensin II itself or to the heptapeptide angiotensin III which is formed therefrom as a cleavage product. Inhibition of the enzymatic activity of renin brings about a decrease in the formation of angiotensin I and as a consequence thereof the formation of a smaller amount of angiotensin II. The reduced concentration of this active peptide hormone is the actual reason for the blood pressure-lowering activity of renin inhibitors.

The activity of renin inhibitors can be demonstrated experimentally by means of the in vitro test described hereinafter:

In vitro test with pure human renin

The test is carried out in Eppendorf test tubes. The incubation mixture consists of (1) 100 μl of human renin in buffer A (0.1M sodium phosphate solution, pH 7.4, containing 0.1% bovine serum albumin, 0.1% sodium azide and 1 mM ethylenediaminetetraacetic acid), sufficient for a renin activity of 2–3 ng of angiotensin I/ml/hr.; (2) 145 μl of buffer A; (3) 30 μl of 10 μM human tetradecapeptide renin substrate (hTD) in 10 mM hydrochloric acid; (4) 15 μl of dimethyl sulphoxide with or without inhibitor and (5) 10 μl of a 0.03 molar solution of hydroxyquinoline sulphate in water.

The samples are incubated for three hours at 37° C. or 4° C. in triplicate. 2×100 μl samples per experimental test tube are used in order to measure the production of angiotensin I via RIA (standard radioimmunoassay; clinical assay solid phase kit). Cross reactivities of the antibody used in the RIA are: angiotensin I 100%; angiotensin II 0.0013%; hTD (angiotensin I-Val-Ile-His-Ser-OH) 0.09%. The production of angiotensin I is determined by the difference between the experiment at 37° C. and that at 4° C.

The following controls are carried out:

(a) Incubation of hTD samples without renin and without inhibitor at 37° C. and 4° C. The difference between these two values gives the base value of the angiotensin I production.

(b) Incubation of hTD samples with renin, but without inhibitor at 37° C. and 4° C. The difference between these values gives the maximal value of angiotensin I production.

In each sample the base value of the angiotensin I production is subtracted from the angiotensin I production which is determined. The difference between the maximal value and the base value gives the value of the maximal substrate hydrolysis (=100%) by renin.

The results are given as $IC_{50}$ values which denote that concentration of the inhibitor at which the enzymatic activity is inhibited by 50%. The $IC_{50}$ values are determined from a linear regression curve from a logit-log plot.

The results obtained in this test are compiled in the following Table:

TABLE

| Compound | $IC_{50}$-values in μmol/lt. |
|---|---|
| A | 0.0018 |
| B | 0.0170 |
| C | 0.0009 |
| D | 0.0012 |
| E | 0.0023 |
| F | 0.0210 |

A=(S)-α-[(S)-α-[[[(2-Amino-1,1-dimethylethyl)sulphonyl]methyl]hydrocinnamamido]-N-[(1S,2R,3S)-1-(cyclohexylmethyl)-3-cyclopropyl-2,3-dihydroxypropyl]imidazole-4-propionamide dihydrochloride, B=(S)-α-[(S)-α-[[(2-Amino-2-methylpropyl)sulphonyl]methyl]hydrocinnamamido]-N-[(1S,2R,3S)-1-(cyclohexylmethyl)-3-cyclopropyl-2,3-dihydroxypropyl]imidazole-4-propionamide diacetate, C=(S)-α-[(S)-α-[(tert-Butylsulphonyl)methyl]hydrocinnamamido]-N-[(1S,2R)-2-(cyclohexylmethyl)-2-[(R or S)-3-cyclopropyl-2-oxo-5-oxazolidinyl]-2-hydroxyethyl]-imidazole-4-propionamide, D=(S)-α-[[(S)-1-[[(1S,2R,3S)-1-(Cyclohexylmethyl)-3-cyclopropyl-2,3-dihydroxypropyl]carbamoyl]-2-imidazol-4-ylethyl]carbamoyl]phenethyl 1-piperidinecarboxylate, E=(S)-α-[(S)-α-[(tert-Butylsulphonyl)methyl]hydrocinnamamido]-N-[(1S,2R,3S)-1-(cyclohexylmethyl)-3-cyclopropyl-3-fluoro-2-hydroxypropyl]imidazole-4-propionamide and F=N-[(S)-1-[[(1S,2R,3S)-1-(Cyclohexylmethyl)-3-cyclopropyl-2,3-dihydroxypropyl]carbamoyl]-2-imidazol-4-ylethyl]indole-2-carboxamide.

The compounds of formula I as well as their pharmaceutically usable salts can be used as medicaments, e.g. in the form of pharmaceutical preparations. The pharmaceutical preparations can be administered enterally such as orally, e.g. in the form of tablets, coated tablets, dragees, hard and soft gelatine capsules, solutions, emulsions or suspensions, nasally, e.g. in the form of nasal sprays, or rectally, e.g. in the form of suppositories. However, the administration can also be effected parenterally such as intramuscularly or intravenously, e.g. in the form of injection solutions.

For the manufacture of tablets, coated tablets, dragees and hard gelatine capsules the compounds of formula I as well as their pharmaceutically usable salts can be processed with pharmaceutically inert, inorganic or organic excipients. Lactose, maize starch or derivatives thereof, talc, stearic acid or its salts etc can be used e.g. as such excipients for tablets, dragees and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are, e.g., natural or hardened oils, waxes, fats, semi-liquid or liquid polyols etc.

Moreover, the pharmaceutical preparations can contain preserving agents, solubilizers, viscosity-increasing substances, stabilizing agents, wetting agents, emulsifying agents, sweetening agents, colouring agents, flavouring agents, salts for varying the osmotic pressure, buffers, coating agents or antioxidants. They can also contain other therapeutically valuable substances.

In accordance with the invention the compounds of general formula I as well as their pharmaceutically usable salts can be used in the control or prevention of high blood pressure and cardiac insufficiency. The dosage can vary within wide limits and will, of course, be fitted to the individual requirements in each particular case. In general, in the case of oral administration there should suffice a daily dosage of about 3 mg to about 3 g, preferably about 10 mg to about 1 g, e.g., approximately 300 mg per person, divided into preferably 1–3 unit doses, which can e.g. be of the same amount, whereby, however, the upper limit just given can also be exceeded when this is found to be indicated. Usually, children receive half of the adult dosage.

The following Examples are intended to illustrate the present invention, but are not intended to be limiting in any manner. All temperatures are given in degrees Celsius. The following abbreviations are used:

H-His-OH=L-histidine
H-Phe-OH=L-phenylalanine
H-Pro-OH=L-proline
Boc=t-butoxycarbonyl
Fmoc=9-fluorenylmethoxycarbonyl

EXAMPLE 1

A mixture of 200 mg (0.5 mmol) of (S)-α-amino-N-[(1S,2R,3S)-1-(cyclohexylmethyl)-3-cyclopropyl-2,3-dihydroxypropyl]imidazole-4-propionamide, 197 mg (0.5 mmol) of (S)-α-[[[2-(1-tert-butoxyformamido)-1,1-dimethylethyl]sulphonyl]methyl]hydrocinnamic acid, 56 mg (0.5 mmol) of triethylamine, 89 mg (0.5 mmol) of HOBT and 209 mg (0.5 mmol) of HBTU in 15 ml of dimethylformamide is stirred at room temperature for 4 hours. Thereafter, the reaction mixture is evaporated to dryness in a high vacuum, the residue is taken up in 50 ml of ethyl acetate and washed twice with 20 ml of saturated sodium bicarbonate solution. After drying the organic phase over sodium sulphate the solvent is evaporated under reduced pressure. For purification, the residue (420 mg) is chromatographed on 20 g of silica gel using a 95:5:0.1 mixture of methylene chloride, methanol and ammonia as the eluent. After lyophilization from dioxan/water there is obtained tert-butyl [2-[[(S)-2-[[(S)-1-[[(1S,2R,3S)-1-(cyclohexylmethyl)-3-cyclopropyl-2,3-dihydroxypropyl)carbamoyl]-2-imidazol-4-ylethyl]carbamoyl]-3-phenylpropyl]sulphonyl]-2-methylpropyl]carbamate as a colourless, amorphous powder; MS: 746 (M+H)⁺.

The (S)-α-[[[2-(1-tert-butoxyformamido)-1,1-dimethylethyl]sulphonyl]methyl]hydrocinnamic acid used as the starting material was prepared as follows:

(a) tert-Butyl [2-(benzylthio)-2-methylpropyl]carbamate:

3.28 g (15.1 mmol) of di-tert-butyl dicarbonate are added dropwise at 0° to a mixture of 3.17 g (13.7 mmol) of 2-(benzylthio)-2-methylpropylamine hydrochloride [B. J. Sweetmann et al., J. Med. Chem. 14, 868 (1971)] and 1.45 g (14.3 mmol) of triethylamine in 30 ml of dimethylformamide. Subsequently, the reaction mixture is stirred at room temperature overnight and thereafter evaporated in a high vacuum. The residue is extracted three times with 50 ml of ether each time. The organic solutions are combined, washed with 50 ml of water, dried over sodium sulphate and evaporated. Chromatography of the thus-obtained crude product (4.18 g) on silica gel with a 6:1 mixture of hexane and ether as the eluent yields 3.5 g of tert-butyl [2-(benzylthio)-2-methylpropyl]carbamate as a colourless oil; MS: 239 (M–C$_4$H$_8$)⁺.

(b) tert Butyl [2-methyl-2-mercaptopropyl]carbamate:

3.49 g (11.8 mmol) of tert-butyl [2-(benzylthio)-2-methylpropyl]carbamate dissolved in 10 ml of ether are placed in a flask which is fitted with an ammonia condenser and a gas inlet. The solution is cooled to –78°, thereafter about 35 ml of ammonia are condensed in. Sodium (about 1 g) in small pieces is added to this solution until the blue colour of the solution persists. The mixture is allowed to warm slowly, the excess sodium is destroyed by the addition of ammonium chloride (about 3.5 g) and the ammonia is blown off using nitrogen. The residue is partitioned between 50 ml of water and 250 ml of ether. The organic phase is separated, dried over sodium sulphate and evaporated. There are obtained 2.29 g of tert-butyl [2-methyl-2-mercaptopropyl]carbamate as a colourless solid; MS: 149 (M–C$_4$H$_8$)⁺.

(c) tert-Butyl [2-[[(RS)-2-(ethoxycarbonyl)-3-phenylpropyl]sulphonyl]-2-methylpropyl]carbamate:

10.2 ml (11 mmol) of 1.08N sodium ethylate solution are added dropwise at 0° to a mixture of 1.99 g (10.47 mmol) of ethyl α-benzylacrylate and 2.26 g (11 mmol) of tert-butyl [2-methyl-2-mercaptopropyl]carbamate in 5 ml of dioxan. Thereafter, the mixture is stirred at 0° for 0.5 hours and at room temperature for 2.5 hours. The reaction mixture is treated while cooling with ice with 8.96 g (14.6 mmol) of potassium monopersulphate triple salt, suspended in 15 ml of water, and stirred at room temperature for 1 hour. Thereafter, the mixture is cooled to 0° and a suspension of 8.96 g (14.6 mmol) of potassium monopersulphate triple salt in 15 ml of water is again added. Subsequently, the mixture is stirred at room temperature for 15 hours. The reaction mixture is diluted with 50 ml of water and the aqueous solution is extracted three times with 50 ml of ether each time. The combined organic solutions are dried over sodium sulphate and evaporated. There are obtained 3.25 g of tert-butyl [2-[[(RS)-2-(ethoxycarbonyl)-3-phenylpropyl]sulphonyl]-2-methylpropyl]carbamate as a colourless oil; MS: 445 (M+NH$_4$)⁺.

(d) (S)-α-[[[2-(1-tert-Butoxyformamido)-1,1-dimethylethyl]sulphonyl]methyl]hydrocinnamic acid and ethyl (R)-α-[[[2-(1-tert-butoxyformamido)-1,1-dimethylethyl]sulphonyl]methyl]hydrocinnamate:

A 0.039N calcium hydroxide solution is added while stirring to a mixture of 1.75 g (4.1 mmol) of tert-butyl [2-[[(RS)-2-(ethoxycarbonyl)-3-phenylpropyl]sulphonyl]-2-methylpropyl]carbamate and 70 mg of α-chymotrypsin in 5 ml of ethanol and 250 ml of water in such a manner that the pH value is maintained at 7.5. When calcium hydroxide is no longer consumed, the working-up of the reaction mixture is effected by extracting the aqueous solution twice with 50 ml of ethyl acetate each time. The combined organic phases are washed with 25 ml of saturated sodium bicarbonate solution, dried over sodium sulphate and evaporated under reduced pressure. There is obtained 0.86 g of ethyl (R)-α-[[[2-(1-tert-butoxyformamido)-1,1-dimethylethyl]sulphonyl]methyl]hydrocinnamate as a yellowish oil; MS: 445 (M+NH$_4$)⁺.

The aqueous phase and the sodium bicarbonate solution are combined, adjusted to pH 3.5 with 1N hydrochloric acid and, after the addition of solid sodium chloride, extracted twice with 50 ml of ethyl acetate each time. After drying over sodium sulphate and evaporation under reduced pressure there is obtained 0.81 g of (S)-α-[[[2-(1-tert-butoxyformamido)-1,1-dimethylethyl]sulphonyl]methyl] hydrocinnamic acid as a yellowish foam; MS: 343 (M–C$_4$H$_8$)⁺.

The (S)-α-amino-N-[(1S,2R,3S)-1-(cyclohexylmethyl)-3-cyclopropyl-2,3-dihydroxypropyl]imidazole-4-propionamide used as the starting material was prepared as follows:

(e) tert-Butyl (4S,5R)-4-(cyclohexylmethyl)-5-[(S)-cyclopropylhydroxymethyl]-2,2-dimethyl-3-oxazolidinecarboxylate and tert-butyl (4S,5R)-4-(cyclohexylmethyl)-5-[(R)-cyclopropylhydroxymethyl]-2,2-dimethyl-3-oxazolidinecarboxylate:

A solution of 3.21 g (9.8 mmol) of tert-butyl (4S,5R)-4-(cyclohexylmethyl)-5-formyl-2,2-dimethyl-3-oxazolidinecarboxylate (WO 87/05302) in 25 ml of tetrahydrofuran is added dropwise at about 15° to a solution of the Grignard compound prepared from 3.94 ml (49 mmol) of cyclopropyl bromide and 1.2 g (0.049 gram atom) of magnesium shavings in 22 ml of tetrahydrofuran and the reaction mixture is subsequently stirred at room temperature under argon for 16 hours. Thereafter, the reaction mixture is poured into 40 ml of an ice-cold, saturated ammonium chloride solution and extracted twice with 50 ml of ethyl acetate each time. The ethyl acetate extracts are washed with 40 ml of ice-cold, saturated ammonium chloride solution, combined, dried over sodium sulphate and evaporated. For purification, the residue (4.33 g) is chromatographed over a column of 110 g of silica gel, prepared with toluene and 1% triethylamine, using a 95:5 mixture of toluene and ethyl acetate as the eluent. There are obtained 1.9 g of tert-butyl (4S,5R)-4-(cyclohexylmethyl)-5-[(S)-cyclopropylhydroxymethyl]-2,2-dimethyl-3-oxazolidinecarboxylate, MS: 368 (M+H)$^+$, and 0.5 g of tert-butyl (4S,5R)-4-(cyclohexylmethyl)-5-[(R)-cyclopropylhydroxymethyl]-2,2-dimethyl-3-oxazolidinecarboxylate, MS: 368 (M+H)$^+$, both as a colourless oil.

(f) (1S,2R,3S)-3-Amino-4-cyclohexyl-1-cyclopropyl-1,2-butanediol:

1.42 g (3.86 mmol) of tert-butyl (4S,5R)-4-(cyclohexylmethyl)-5-[(S)-cyclopropylhydroxymethyl]-2,2-dimethyl-3-oxazolidinecarboxylate dissolved in 15 ml of methanol and 10 ml of water are treated with 4 ml of 7.5N hydrochloric acid and stirred at 50° for 3 hours. The reaction solution is cooled to 3° in an ice bath, treated dropwise with 4 ml of 7.5N sodium hydroxide solution and stirred for 1 hour. The suspension obtained is evaporated under reduced pressure, the water is removed azeotropically twice with 10 ml of toluene and the residue is stirred three times with 10 ml of a 95:5 mixture of methylene chloride and methanol. The insoluble residue is filtered off and the filtrate is evaporated under reduced pressure. The crude product obtained (1.14 g) is suspended in 15 ml of ether and then filtered. There is obtained 0.58 g of (1S,2R,3S)-3-amino-4-cyclohexyl-1-cyclopropyl-1,2-butanediol as a colourless crystals, m.p. 141°–142°.

(g) (S)-α-Amino-N-[(1S,2R,3S)-1-(cyclohexylmethyl)-3-cyclopropyl-2,3-dihydroxypropyl]imidazole-4-propionamide:

A mixture of 343 mg (1.51 mmol) of (1S,2R,3S)-3-amino-4-cyclohexyl-1-cyclopropyl-1,2-butanediol, 995 mg (1.66 mmol) of (Fmoc)$_2$His-OH, 0.21 ml (1.61 mmol) of 4-ethylmorpholine, 449 mg (3.22 mmol) of HOBT and 347 mg (1.81 mmol) of EDC in 20 ml of dimethylformamide is left to stand at room temperature overnight. Thereafter, the reaction mixture is evaporated in a high vacuum, the residue is poured into a mixture of ice and 90 ml of sodium bicarbonate solution and extracted three times with 150 ml of ethyl acetate each time. The three ethyl acetate extracts are washed in succession with 70 ml of saturated ammonium chloride solution, 70 ml of 2N sodium bicarbonate solution and 70 ml of saturated sodium chloride solution, combined, dried over magnesium sulphate, filtered and evaporated. The crude product obtained is stirred at room temperature for 3 hours in 60 ml of methylene chloride and 2 ml of piperidine. Then, the reaction mixture is evaporated and the residue is triturated with 50 ml of hexane and filtered off. The filtrate is chromatographed on 70 g of silica gel with a 65:10:1 mixture of methylene chloride, methanol and ammonia as the eluent, whereby there are obtained 390 mg of (S)-α-amino-N-[(1S,2R,3S)-1-(cyclohexylmethyl)-3-cyclopropyl-2,3-dihydroxypropyl]-imidazole-4-propionamide as a colourless foam; MS: 365 (M+H)$^+$.

EXAMPLE 2

The following compounds were manufactured in an analogous manner to that described in Example 1:

From (S)-α-amino-N-[(1S,2R,3S)-1-(cyclohexylmethyl)-3-cyclopropyl-2,3-dihydroxypropyl]imidazole-4-propionamide and (S)-α-[[[2-(dimethylamino)-1,1-dimethylethyl]sulphonyl]methyl]hydrocinnamic acid hydrochloride the (S)-N-[(1S,2R,3S)-1-(cyclohexylmethyl)-3-cyclopropyl-2,3-dihydroxypropyl]-α-[(S)-α-[[[2-(dimethylamino)-1,1-dimethylethyl]sulphonyl]methyl]hydrocinnamamido] imidazole-4-propionamide as a colourless, amorphous solid, MS: 674 (M+H)$^+$;

from (S)-α-amino-N-[(1S,2R,3S)-1-(cyclohexylmethyl)-3-cyclopropyl-2,3-dihydroxypropyl]imidazole-4-propionamide and (S)-α-[[1,1-dimethyl-2-morpholinoethyl)sulphonyl]methyl]hydrocinnamic acid hydrochloride the (S)-N-[(1S,2R,3S)-1-(cyclohexylmethyl)-3-cyclopropyl-2,3-dihydroxypropyl]-α-[(S)-α-[[(1,1-dimethyl-2-morpholinoethyl)sulphonyl]methyl] hydrocinnamamido]imidazole-4-propionamide as a colourless, amorphous solid, MS: 716 (M+H)$^+$;

from (S)-α-amino-N-[(1S,2R,3S)-1-(cyclohexylmethyl)-3-cyclopropyl-2,3-dihydroxypropyl]imidazole-4-propionamide and (S)-α-[[[2-[1-(benzyloxy)formamido]-2-methylpropyl]sulphonyl]methyl] hydrocinnamic acid the benzyl [2-[[(S)-2-[[(S)-1-[[(1S,2R,3S)-1-(cyclohexylmethyl)-3-cyclopropyl-2,3-dihydroxypropyl]carbamoyl]-2-imidazol-4-ylethyl] carbamoyl]-3-phenylpropyl]sulphonyl]-1,1-dimethylethyl]carbamate as a colourless, amorphous solid, MS: 780 (M+H)$^+$;

from (S)-α-amino-N-[(1S,2R,3S)-1-(cyclohexylmethyl)-3-cyclopropyl-2,3-dihydroxypropyl]imidazole-4-propionamide and (S)-α-[[[2-[1-(benzyloxy)formamido]-2-methylpropyl]sulphonyl]methyl]-p-fluorohydrocinnamic acid the benzyl [2-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl] carbamoyl]-p-fluorophenethyl]sulphonyl]-1,1-dimethylethyl]carbamate as a colourless, amorphous solid, MS: 798 (M+H)$^+$;

from (S)-α-amino-N-[(1S,2R,3S)-1-(cyclohexylmethyl)-3-cyclopropyl-2,3-dihydroxypropyl]imidazole-4-propionamide and (S)-α-[(tert-butylsulphonyl)methyl] cyclohexanepropionic acid the (S)-α-[(S)-α-[(tert-butylsulphonyl)methyl]cyclohexanepropionamido]-N-[(1S,2R,3S)-1-(cyclohexylmethyl)-3-cyclopropyl-2,3-dihydroxypropyl]imidazole-4-propionamide as a colourless, amorphous solid, MS: 637 (M+H)$^+$;

from (S)-α-amino-N-[(1S,2R,3S)-1-(cyclohexylmethyl)-3-cyclopropyl-2,3-dihydroxypropyl]imidazole-4-propionamide and (S)-α-[(tert-butylsulphonyl)methyl]-2-thiophenepropionic acid the (S)-α-[(S)-α-[(tert-butylsulphonyl)methyl]-2-thiophenecarboxamido]-N-[(1S,2R,3S)-1-(cyclohexylmethyl)-3-cyclopropyl-2,3-dihydroxypropyl]imidazole-4-propionamide as a colourless, amorphous solid, MS: 637 (M+H)⁺;

from (S)-α-amino-N-[(1S,2R,3S)-1-(cyclohexylmethyl)-3-cyclopropyl-2,3-dihydroxypropyl]imidazole-4-propionamide and (RS)-α-[(tert-butylsulphonyl)methyl]-β,β-dimethylhydrocinnamic acid, after chromatographic separation of the epimers, the (S)-α-[(R or S)-α-[(tert-butylsulphonyl)methyl]-β,β-dimethylhydrocinnamamido]-N-[(1S,2R,3S)-1-cyclohexylmethyl-3-cyclopropyl-2,3-dihydroxypropyl]-3-(4-imidazolyl)propionamide, MS: 659 (M+H)⁺, and the (S)-α-[(S or R)-α-[(tert-butylsulphonyl)methyl]-β,β-dimethylhydrocinnamamido]-N-[(1S,2R,3S)-1-cyclohexylmethyl-3-cyclopropyl-2,3-dihydroxypropyl]-3-(4-imidazolyl)propionamide, MS: 659 (M+H)⁺, each as a colourless, amorphous solid.

The acids used as starting materials were prepared as follows:

(S)-α-[[[2(Dimethylamino)-1,1-dimethylethyl]sulphonyl]methyl]hydrocinnamic acid hydrochloride In an analogous manner to that described in Example 1(c), ethyl α-benzylacrylate is reacted with sodium ethylate and 1-(dimethylamino)-2-methyl-2-propanethiol [J. L. Corbin et. al., Inorg. Chem. 1984, 23(21), 3404] to give ethyl (RS)-α-[[[2-(dimethylamino)-1,1-dimethylethyl]sulphonyl]methyl]hydrocinnamate which, after enzymatic hydrolysis using α-chymotrypsin carried out in an analogous manner to Example 1(d), yields (S)-α-[[[2-(dimethylamino)-1,1-dimethylethyl]sulphonyl]methyl]hydrocinnamic acid hydrochloride; MS: 328 (M+H)⁺.

(S)-α-[[1,1-Dimethyl-2-morpholinoethyl)sulphonyl]methyl]hydrocinnamic acid hydrochloride This compound is obtained, also in an analogous manner to that described in Example 1(c) and (d), by reacting ethyl α-benzylacrylate with sodium ethylate and α,α-dimethyl-4-morpholinoethanethiol (Japan. Kokai 78 32,736) and enzymatic hydrolysis of the ethyl (RS)-α-[[1,1-dimethyl-2-morpholinoethyl)sulphonyl]methyl]hydrocinnamate using α-chymotrypsin. MS: 370 (M+H)⁺

(S)-α-[[[2-[1-(Benzyloxy)formamido]-2-methylpropyl]sulphonyl]methyl]hydrocinnamic acid In an analogous manner to that described in Example 1(c), ethyl α-benzylacrylate is reacted with tert-butyl (2-mercapto-1,1-dimethylethyl)carbamate to give tert-butyl [2-[[2-(ethoxycarbonyl)-3-phenylpropyl]sulphonyl]-1,1-dimethyl]carbamate. After cleavage of the Boc protecting group with hydrochloric acid in dioxan and introduction of the benzyloxycarbonyl protecting group with benzyloxycarbonyloxysuccinimide/triethylamine and subsequent enzymatic hydrolysis using α-chymotrypsin, as described in Example 1(d), there is obtained (S)-α-[[[2-[1-(benzyloxy)formamido]-2-methylpropyl]sulphonyl]methyl]hydrocinnamic acid as a colourless oil; MS: 389 (M—CO₂)⁺.

The tert-butyl (2-mercapto-1,1-dimethylethyl)carbamate used as the starting material was prepared as follows:

This compound was prepared from 2-(benzylthio)-1,1-dimethylethylamine hydrochloride [J. L. Corbin et al., Inorg. Chem. 1984, 23(21), 3404] in an analogous manner to that described in Example 1(a) and (b). MS: 205 (M)⁺.

(S)-α-[[[2-[1-(Benzyloxy)formamido]-2-methylpropyl]sulphonyl]methyl]-p-fluorohydrocinnamic acid:

In an analogous manner to that described above, starting from ethyl 2-(p-fluorobenzyl)acrylate and tert-butyl (2-mercapto-1,1-dimethylethyl)carbamate there is obtained, after enzymatic hydrolysis, the (S)-α-[[[2-[1-(benzyloxy)formamido]-2-methylpropyl]sulphonyl]methyl]-p-fluorohydrocinnamic acid as a colourless oil; MS: 502 (M+Na)⁺.

The ethyl 2-(p-fluorobenzyl)acrylate used as the starting material was prepared as follows:

This compound was obtained in analogy to the method described in Synthesis 1979, 29, starting from diethyl p-fluorobenzylmalonate (A. Chraibi, Ann. Pharm. Francaises, 38, 1980, 343), MS: 208 (M⁺).

(S)-α-[(tert.Butylsulphonyl)methyl]cyclohexanepropionic acid:

A mixture of 2 g (7 mmol) of (S)-α-[(tert-butylsulphonyl)methyl]hydrocinnamic acid (EPA 0236734) and 2 g of rhodium/aluminium oxide catalyst (5%) in 100 ml of ethanol is hydrogenated for 10 hours at 50° and 10 bar. After filtering off the catalyst the reaction solution is evaporated under reduced pressure and the residue is recrystallized from a 9:1 mixture of hexane and ethyl acetate. There are obtained 1.6 g of (S)-α-[(tert-butylsulphonyl)methyl]cyclohexanepropionic acid as colourless needles; MS: 308 (M+NH₄)⁺.

(S)-α-[(tert-Butylsulphonyl)methyl]-2-thiophenepropionic acid:

This compound is prepared in a manner analogous to Example 1(d) by the enzymatic hydrolysis of ethyl (S)-α-[(tert-butylsulphonyl)methyl]-2-thiophenepropionate which, in turn, is prepared analogously to the synthesis, described in EPA 0236734, of ethyl (RS)-α-[(tert-butylsulphonyl)methyl]hydrocinnamate from diethyl 2-thionylmethylmalonate (P. Cagniant et al., Bull. Soc. Chim. Fr. 1954, 1349). MS: 318 (M)⁺.

(RS)-α-[(tert-Butylsulphonyl)methyl]-β,β-dimethylhydrocinnamic acid:

This compound is prepared in a manner analogous to the synthesis, described in EPA 0236734, of (RS)-α-[(tert-butylsulphonyl)methyl]hydrocinnamic acid starting from diethyl benzyl-α,α-dimethylmalonate (C. Holmberg et al., Liebigs Ann. Chem. 1981, 748); MS: 330 (M+NH₄)⁺.

EXAMPLE 3

The following compounds were manufactured in an analogous manner to that described in Example 1:

From (S)-α-amino-N-[(1S,2R,3S)-1-(cyclohexylmethyl)-3-cyclopropyl-2,3-dihydroxypropyl]imidazole-4-propionamide and (S)-α-[(morpholinosulphonyl)methyl]hydrocinnamic acid the (S)-N-[(1S,2R,3S)-1-(cyclohexylmethyl)-3-cyclopropyl-2,3-dihydroxypropyl]-α-[(S)-α-(morpholinosulphonyl)methyl]hydrocinnamamido]imidazole-4-propionamide as a colourless, amorphous solid, MS: 660 (M+H)⁺;

from (S)-α-amino-N-[(1S,2R,3S)-1-(cyclohexylmethyl)-3-cyclopropyl-2,3-dihydroxypropyl]imidazole-4-propionamide and (S)-α-[[[(S)-2-(tert-butyloxycarbonyl)-1-pyrrolidinyl]sulphonyl]methyl]hydrocinnamic acid the 1-[[(S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulphonyl]-L-proline tert-butyl ester as a colourless, amorphous solid, MS: 744 (M+H)⁺.

The hydrocinnamic acids used as starting materials were prepared as follows:

(S)-α-[(Morpholinosulphonyl)methyl]hydrocinnamic acid:

6.6 g (75.8 mmol) of morpholine are added dropwise at −10° to a solution of 6.23 g (21.4 mmol) of ethyl 2-benzyl-3-chlorosulphonyl-propionate (EPA 0236734) in 150 ml of methylene chloride. The solution is stirred at −10° for 1 hour and at 0° for 1 hour and subsequently acidified with 1N hydrochloric acid. The organic phase is then extracted with 50 ml of water, dried over sodium sulphate and evaporated. For purification, the residue (7.64 g) is chromatographed on 300 g of silica gel using methylene chloride as the eluent. There are obtained 6.78 g of ethyl (RS)-α-[(morpholinosulphonyl)methyl]-hydrocinnamate as a colourless oil; MS: 341 (M)⁺. This is converted into (S)-α-[(morpholinosulphonyl)methyl]hydrocinnamic acid by enzymatic hydrolysis using α-chymotrypsin in an analogous manner to that described in Example 1(d).

(S)-α-[[[(S)-2-(tert-Butyloxycarbonyl)-1-pyrrolidinyl]sulphonyl]methyl]hydrocinnamic acid:

In an analogous manner to that described above, by reacting ethyl 2-benzyl-3-chlorosulphonylpropionate with L-proline tert-butyl ester in the presence of triethylamine there is obtained 1-[[(RS)-2-(ethoxycarbonyl)-3-phenylpropyl]sulphonyl]-L-proline tert-butyl ester which is converted into (S)-α-[[[(S)-2-(tert-butyloxycarbonyl)-1-pyrrolidinyl]sulphonyl]methyl]hydrocinnamic acid by enzymatic hydrolysis using α-chymotrypsin.

EXAMPLE 4

A mixture of 1.98 g (3.06 mmol) of (S)-1-(tert-butoxycarbonyl)-α-[(S)-α-[(tert-butylsulphonyl)methyl]hydrocinnamamido]imidazole-4-propionic acid, 0.58 g (2.55 mmol) of (1S,2R,3S)-3-amino-4-cyclohexyl-1-cyclopropyl-1,2-butanediol, 0.5 g (3.06 mmol) of 3,4-dihydro-3-hydroxy-4-oxo-1,2,3-benzotriazine, 0.42 ml (3.07 mmol) of triethylamine and 1.16 g. (3.06 mmol) of HBTU in 30 ml of dimethylformamide is stirred at room temperature under argon for 2 hours. Subsequently, the dimethylformamide is evaporated in a high vacuum and the residue is taken up in 60 ml of ethyl acetate. The ethyl acetate solution is extracted with 30 ml of cold 2N sodium bicarbonate solution and the aqueous phase is back-extracted twice with 60 ml of ethyl acetate. The combined organic phases are washed in sequence with 30 ml of cold, saturated ammonium chloride solution, 30 ml of cold 2N sodium bicarbonate solution and 30 ml of saturated sodium chloride solution. The organic phase is dried over sodium sulphate and evaporated under reduced pressure. There are obtained 2.82 g of (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]-1-Boc-imidazole-4-propionamide as a pale yellow foam.

The (S)-1-(tert-butoxycarbonyl)-α-[(S)-α-[(tert-butylsulphonyl)methyl]hydrocinnamamido]imidazole-4-propionic acid used as the starting material was prepared as follows:

(a) Methyl (S)-α-[(S)-α-[[(tert-butylsulphonyl)methyl]hydrocinnamamido]imidazolepropionate:

A mixture of 5.7 (20 mmol) of (S)-α-[(tert-butylsulphonyl)methyl)hydrocinnamic acid (EPA 0236734) 4.85 g (20 mmol) of L-histidine methyl ester dihydrochloride, 10.3 ml (81.7 mmol) of N-ethylmorpholine and 2.98 g (20 mmol) of HOBT in 85 ml of dimethylformamide is treated portionwise at 0°–2° under argon with 4.23 g (22 mmol) of EDC and subsequently stirred at room temperature overnight. Thereafter, the solvent is evaporated in a high vacuum, the residue is taken up in 100 ml of ethyl acetate and washed in sequence three times with 10 ml of 2N sodium bicarbonate solution, twice with 10 ml of saturated sodium chloride solution, twice with 10 ml of saturated ammonium chloride solution and twice with 5 ml of saturated sodium chloride solution. The aqueous phases are extracted three times with 20 ml of ethyl acetate and the pooled organic phases are dried over sodium sulphate and evaporated under reduced pressure. For purification, the crude product obtained (9.4 g) is chromatographed on 300 g of silica gel using a 95:5 mixture of methylene chloride and methanol as the eluent. There are obtained 8.6 g of methyl (S)-α-[(S)-α-[(tert-butylsulphonyl)methyl]hydrocinnamamido]imidazolpropionate as a colourless foam; MS: 436 (M+H)⁺.

(b) (S)-1-(tert-Butoxycarbonyl)-α-[(S)-α-[(tert-butylsulphonyl)methyl]hydrocinnamamido]imidazole-4-propionic acid:

A solution of 1.33 g (3.06 mmol) of methyl (S)-α-[(S)-α-[(tert-butylsulphonyl)methyl]hydrocinnamamido]imidazolepropionate in 4 ml of dioxan is treated dropwise with 3.98 ml of 1N sodium hydroxide solution while cooling with ice and the mixture is stirred at this temperature for 30 minutes, whereby the methyl ester is converted quantitatively into the corresponding acid.

Subsequently, the reaction mixture is treated dropwise at 0°–5° with a solution of 0.8 g (3.67 mmol) of di-tert-butyl dicarbonate in 4 ml of dioxan and, after removal of the ice bath, the mixture is stirred at room temperature for 5 hours. Thereafter, 3.98 ml of 1N hydrochloric acid and 25 ml of water are added and the mixture is extracted with 55 ml of ethyl acetate. The aqueous phase is back-washed with 50 ml of ethyl acetate and the combined organic phases are washed twice with 25 ml of water, dried over sodium sulphate and evaporated under reduced pressure. There are obtained 1.98 g of (S)-1-(tert-butoxycarbonyl)-α-[(S)-α-[(tert-butylsulphonyl)methyl]hydrocinnamamido]imidazole-4-propionic acid as a foam; MS: 522 (M+H)⁺.

EXAMPLE 5

In an analogous manner to that described in Example 4, by condensing N-[(S)-α-[(tert-butylsulphonyl)methyl]hydrocinnamoyl]-1-(2,4-dinitrophenyl)-L-histidine with (1S,2R,3S)-3-amino-4-cyclohexyl-1-cyclopropyl-1,2-butanediol there is obtained (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]-1-(2,4-dinitrophenyl)imidazole-4-propionamide as a yellow solid; MS: 797 (M+H)⁺.

The N-[(S)-α-[(tert-butylsulphonyl)methyl]hydrocinnamoyl]-1-(2,4-dinitrophenyl)-L-histidine used as the starting material was prepared as follows:

23.3 g (54.6 mmol) of methyl (S)-α-[(S)-α-[(tert-butylsulphonyl)methyl]hydrocinnamamido]imidazolepropionate in 250 ml of methylene chloride are treated with 7.43 ml (54.6 mmol) of triethylamine. Subsequently, 9.94 g (54.6 mmol) of 2,4-dinitro-1-fluorobenzene in 100 ml of methylene chloride are added dropwise while cooling with ice within about 20 minutes and the reaction mixture is stirred at room temperature until the reaction has finished, this being the case after 4 hours (checked by thin-layer chromatography). Usual working-up of the reaction mixture yields 20.5 g (62%) of N-[(S)-α-[(tert-butylsulphonyl)methyl]hydrocinnamoyl]-1-(2,4-dinitrophenyl)-L-histidine methyl ester as a brown foam, Rf value 0.4 in a 30:1 mixture of methylene chloride and methanol, MS: 602 (M+H)⁺.

20.5 g (34.07 mmol) of N-[(S)-α-[(tert-butylsulphonyl)methyl]hydrocinnamoyl]-1-(2,4-dinitrophenyl)-L-histidine methyl ester are dissolved in 180 ml of dioxan, treated with 85 ml (170.34 mmol) of 2N hydrochloric acid and subsequently heated to 80° for 2.5 hours. Usual working-up and crystallization from ether/hexane yields 15.7 g (78%) of N-[(S)-α-[(tert-butylsulphonyl)methyl]hydrocinnamoyl]-1-(2,4-dinitrophenyl)-L-histidine in the form of a pale yellow amorphous solid, Rf value 0.2 in a 5:1 mixture of methylene chloride and methanol, MS: 588 (M+H)$^+$.

EXAMPLE 6

The following compounds were manufactured in an analogous manner to that described in Example 4:

From (S)-1-(tert-butoxycarbonyl)-α-[(S)-α-[(tert-butylsulphonyl)methyl]hydrocinnamamido]imidazole-4-propionic acid and (1S,2R,3S)-3-amino-1-cyclopropyl-4-(4,4-difluorocyclohexyl)-1,2-butanediol the (S)-α-[(S)α-[(tert-butylsulphonyl)methyl] hydrocinnamamido]-N-[(1S,2R,3S)-3-cyclopropyl-1-[(4,4-difluorocyclohexyl)methyl]-2,3-dihydroxypropyl]-1-Boc-imidazole-4-propionamide;

from (S)-1-(tert-butoxycarbonyl)-α-[(S)-α-[(tert-butylsulphonyl)methyl]hydrocinnamamido]imidazole-4-propionic acid and (1S,2R)-3-amino-1-cyclopropyl-4-[(RS)-4-hydroxycyclohexyl]-1,2-butanediol the (S)-α-[(S)-α-[(tert-butylsulphonyl)methyl] hydrocinnamamido]-N-[(1S,2R,3S)-1-[[(RS)-4-hydroxycyclohexyl]methyl]-3-cyclopropyl-2,3-dihydroxypropyl]-1-Boc-imidazole-4-propionamide;

from (S)-1-(tert-butoxycarbonyl)-α-[(S)-α-[(tert-butylsulphonyl)methyl]hydrocinnamamido]imidazole-4-propionic acid and (1S,2R,3S)-3-amino-1-cyclopropyl-4-(p-fluorophenyl)-1,2-butanediol the (S)-α-[(S)-α-[(tert-butylsulphonyl)methyl] hydrocinnamamido]-N-[(1S,2R,3S)-3-cyclopropyl-1-(p-fluorobenzyl)-2,3-dihydroxypropyl]-1-Boc-imidazole-4-propionamide;

from (S)-1-(tert-butoxycarbonyl)-α-[(S)-α-[(tert-butylsulphonyl)methyl]hydrocinnamamido]imidazole-4-propionic acid and (1S,2R,3S)-3-amino-4-[(S)-3-cyclohexen-1-yl]-1-cyclopropyl-1,2-butanediol the (S)-α-[(S)-α-[(tert-butylsulphonyl)methyl] hydrocinnamamido]-N-[(1S,2R,3S)-1-[[(S)-3-cyclohexen-1-yl]methyl]-3-cyclopropyl-2,3-dihydroxypropyl]-1-Boc-imidazole-4-propionamide;

from (S)-1-(tert-butoxycarbonyl)-α-[(S)-α-[(tert-butylsulphonyl)methyl]hydrocinnamamido]imidazole-4-propionic acid and (1S,2R,3S)-3-amino-4-[(R)-3-cyclohexen-1-yl]-1-cyclopropyl-1,2-butanediol the (S)-α-[(S)-α-[(tert-butylsulphonyl)methyl] hydrocinnamamido]-N-[(1S,2R,3S)-1-[[(R)-3-cyclohexen-1-yl]methyl]-3-cyclopropyl-2,3-dihydroxypropyl]-1-Boc-imidazole-4-propionamide;

from (S)-1-(tert-butoxycarbonyl)-α-[(S)-α-[(tert-butylsulphonyl)methyl]hydrocinnamamido]imidazole-4-propionic acid and (2RS,3R,4S)-4-Amino-5-cyclohexyl-1,2,3-pentanetriol the (S)-α-[(S)-α-[(tert-butylsulphonyl)methyl]hydrocinnamamido]-N-[(1S,2R,3RS)-1-(cyclohexylmethyl)-2,3,4-trihydroxybutyl]-1-Boc-imidazole-4-propionamide;

from (S)-1-(tert-butoxycarbonyl)-α-[(S)-α-[(tert-butylsulphonyl)methyl]hydrocinnamamido]imidazole-4-propionic acid and (2S,3R,4R or S,5R or S)-2-amino-1-cyclohexyl-3,4,5-heptanetriol the (S)-α-[(S)-α-[(tert-butylsulphonyl)methyl]hydrocinnamamido]-N-[(1S,2R,3R or S,4R or S)-1-(cyclohexylmethyl)-2,3,4-trihydroxyhexyl]-1-Boc-imidazole-4-propionamide.

The aminodiols used as starting materials were prepared analogously to the process which is described in WO 87/05302 for the synthesis of tert-butyl (4S,5R)-4-(cyclohexylmethyl)-5-formyl-2,2-dimethyl-3-oxazolidinecarboxylate starting from Boc-cyclohexylalanine methyl ester followed by the Grignard reaction with cyclopropylmagnesium bromide and cleavage of the Boc and isopropylidene protecting groups analogously to Example 1(f). Replacement of the Boc-cyclohexylalanine methyl ester gives starting from Boc-(4,4-difluorocyclohexyl)alanine methyl ester the (1S,2R,3S)-3-amino-1-cyclopropyl-4-(4,4-difluorocyclohexyl)-1,2-butanediol as a colourless solid, MS: 264 (M+H)$^+$;

starting from Boc-[(RS)-4-hydroxycyclohexyl]alanine methyl ester the (1S,2R)-3-amino-1-cyclopropyl-4-[(RS)-4-hydroxycyclohexyl]-1,2-butanediol as an amorphous solid, MS: 244 (M+H)$^+$;

starting from Boc-(p-fluorophenyl)alanine methyl ester the (1S,2R,3S)-3-amino-1-cyclopropyl-4-(p-fluorophenyl)-1,2-butanediol as a colourless solid, MS: 240 (M+H)$^+$;

starting from Boc-3-[(S)-2-cyclohexen-1-yl]-L-alanine methyl ester the (1S,2R,3S)-3-amino-4-[(S)-3-cyclohexen-1-yl]-1-cyclopropyl-1,2-butanediol as a yellowish oil, MS: 154 (M–C$_4$H$_7$O)$^+$;

starting from Boc-3-[(R)-2-cyclohexen-1-yl]-L-alanine methyl ester the (1S,2R,3S)-3-amino-4-[(R)-3-cyclohexen-1-yl]-1-cyclopropyl-1,2-butanediol as a yellowish oil, MS: 225 (M)$^+$.

The aminotriols used as starting materials were prepared as follows:

(2RS,3R,4S)-4-Amino-5-cyclohexyl-1,2,3-pentanetriol (a) tert-Butyl [(1S,2R,3RS)-1-(cyclohexylmethyl) 2,3,4-trihydroxybutyl]carbamate:

A solution of 1.5 g (2.24 mmol) of tert-butyl [(1S,2S)-1-(cyclohexylmethyl)-2-hydroxy-3-butenyl]carbamate, prepared according to the procedure of J. J. Plattner et al. in J. Med. Chem., 30, (10), (1987), 1729, in 10 ml of pyridine is treated with 845 mg (3.36 mmol) of osmium tetroxide and left to stand at room temperature in the dark for 3 days. Subsequently, the reaction mixture is cooled to 0°, treated with 3 ml of 38% sodium bisulphite solution and stirred for 2 hours. Thereafter, the mixture is poured on to ice and water and extracted three times with 250 ml of ethyl acetate. The combined organic extracts are washed in succession with in each case 60 ml of sodium bicarbonate solution, 20% copper sulphate solution and saturated sodium chloride solution, dried over magnesium sulphate and evaporated under reduced pressure. For purification, the residue (1.20 g) is chromatographed on 30 g of silica gel using a 100:10:1 mixture of methylene chloride, methanol and ammonia as the eluent, whereby there are obtained 590 mg of tert-butyl [(1S,2R,3RS)-1-(cyclohexylmethyl)-2,3,4-trihydroxybutyl] carbamate as a foam, MS: 318 (M+H)$^+$.

(b) (2RS,3R,4S)-4-Amino-5-cyclohexyl-1,2,3-pentanetriol:

A solution of 270 mg of tert-butyl [(1S,2R,3RS)-1-(cyclohexylmethyl)-2,3,4-trihydroxybutyl]carbamate, 15 ml of methanol and 10 ml of 2N hydrochloric acid is heated to 50° overnight. Subsequently, the reaction solution is evaporated to dryness under reduced pressure, the residue obtained is taken up twice in toluene and evaporated to dryness under reduced pressure each time. The crude (2RS,3R,4S)-4-amino-5-cyclohexyl-1,2,3-pentanetriol obtained is used in the next step without further purification; MS: 218 (M+H)$^+$.

2S,3R,4R or S,5R or S)-2-Amino-1-cyclohexyl-3,4,5-heptanetriol (c) tert-Butyl (4S,5R)-5-[(Z)-1-butenyl]-4-(cyclohexylmethyl)-2,2-dimethyl-3-oxazolidinecarboxylate:

A mixture of 1.4 g (4.3 mmol) of tert-butyl (4S,5R)-4-(cyclohexylmethyl)-5-formyl-2,2-dimethyl-3-oxazolidinecarboxylate (WO 87/05302) and 1.79 g (4.3 mmol) of instantylide, consisting of propyltriphenylphosphonium bromide and sodium amide, in 50 ml of tetrahydrofuran is stirred at room temperature under nitrogen for 30 minutes. Subsequently, the reaction mixture is partitioned between water and ethyl acetate. The organic phase is separated, dried over sodium sulphate and evaporated under reduced pressure. For purification, the residue is chromatographed on 80 g of silica gel using a 1:1 mixture of methylene chloride and petroleum ether as the eluent. There are obtained 900 mg of tert-butyl (4S,5R)-5-[(Z)-1-butenyl]-4-(cyclohexylmethyl)-2,2-dimethyl-3-oxazolidinecarboxylate as a resin; MS: 352 (M+H)$^+$.

(d) tert-Butyl (4S,5R)-4-(cyclohexylmethyl)-5-[(1R or S,2R or S)-1,2-dihydroxybutyl]-2,2-dimethyl-3-oxazolidinecarboxylate:

22 mg (0.089 mmol) of osmium tetroxide in the form of a 2% ethylene chloride solution are added under argon to a solution of 900 mg (2.68 mmol) of tert-butyl (4S,5R)-5-[(Z)-1-butenyl]-4-(cyclohexylmethyl)-2,2-dimethyl-3-oxazolidinecarboxylate and 832 mg (6.16 mmol) of 4-methylmorpholine 4-oxide monohydrate in 20 ml of tetrahydrofuran. The reaction mixture is stirred at room temperature for 2.5 hours, then treated with 150 ml of saturated sodium chloride solution and extracted with 150 ml of ethyl acetate. The organic phase is washed in succession with 10% sodium sulphite solution, 1N phosphoric acid and water, dried over sodium sulphate and evaporated under reduced pressure. For purification, the residue is chromatographed on silica gel using a 2:1 mixture of methylene chloride and petroleum ether as the eluent. There are obtained 370 mg of tert-butyl (4S,5R)-4-(cyclohexylmethyl)-5-[(1R or S,2R or S)-1,2-dihydroxybutyl]-2,2-dimethyl-3-oxazolidinecarboxylate as a resin; MS: 370 (M–CH$_3$)$_+$.

(e) (2S,3R,4R or S,5R or S)-α-Amino-1-cyclohexyl-3,4,5-heptanetriol:

Analogously to the procedure described above for the preparation of (2RS,3R,4S)-4-amino-5-cyclohexyl-1,2,3-pentanetriol, by reacting tert-butyl (4S,5R)-4-(cyclohexylmethyl)-5-[(1R or S,2R or S)-1,2-dihydroxybutyl]-2,2-dimethyl-3-oxazolidinecarboxylate there is obtained (2S,3R,4R or S,5R or S)-2-amino-1-cyclohexyl-3,4,5-heptanetriol as an amorphous solid which is used in the next step without further purification.

The alanine methyl esters used as starting materials were prepared as follows:

Boc-(4,4-Difluorocyclohexyl)alanine methyl ester and Boc-[(RS)-4-hydroxycyclohexyl]alanine methyl ester (f) A suspension of 65.8 g (0.22 mmol) of Boc-tyrosine methyl ester and 6.6 g of rhodium/aluminium oxide catalyst (5%) in 175 ml of methanol is hydrogenated for 3 hours at 50° and 4 bar of hydrogen. Subsequently, the catalyst is filtered off, the filtrate is evaporated under reduced pressure and, for purification, the residue obtained is chromatographed on 1 kg of silica gel using a 4:1 mixture of toluene and ethyl acetate as the eluent. There are obtained 41.97 g of Boc-[(RS)-4-hydroxycyclohexyl]alanine methyl ester, MS: 302 (M+H)$^+$, and 6.1 g of Boc-(4-oxocyclohexyl)alanine methyl ester, MS: 300 (M+H)$^+$, each as a colourless oil.

(g) A solution of 300 mg (1 mmol) of Boc-(4-oxocyclohexyl)alanine methyl ester in 1.5 ml of methylene chloride is added at −78° by means of a syringe to a solution of 322 mg (2 mmol) of diethylamino-sulphur trifluoride in 0.5 ml of methylene chloride. The reaction mixture is allowed to warm to −10° and is stirred at this temperature for 1.5 hours. Thereafter, the mixture is poured on to ice and 30 ml of 2N sodium hydrogen carbonate solution and extracted twice with 60 ml of methylene chloride each time. The organic phase is washed with 30 ml of water, dried over sodium sulphate and evaporated. The crude product (450 mg) is chromatographed on 30 g of silica gel using a 9:1 mixture of hexane and ethyl acetate as the eluent. There are obtained 280 mg of Boc-(4,4-difluorocyclohexyl)alanine methyl ester as an oil; MS: 322 (M+H)$^+$.

Boc-3-[(S)-2-Cyclohexen-1-yl]-L-alanine methyl ester (h) (S)-3-Cyclohexene-1-methanol:

0.57 g (15 mmol) of lithium aluminium hydride is added to a solution of 3.57 g (15 mmol) of (R)-tetrahydro-4,4-dimethyl-2-oxo-3-furyl (S)-3-cyclohexene-1-carboxylate (G. Helmchen et al., Tetrahedron Letters 1985, 26, 3095–3098) in 60 ml of absolute tetrahydrofuran and 20 ml of absolute ether. The mixture is heated to reflux for 1 hour, thereafter cooled to −20°, treated dropwise with saturated ammonium chloride solution and extracted three times with ether. The combined organic extracts are washed with water, dried over sodium sulphate and concentrated under pressure. The residual oil is distilled in a high vacuum. (S)-3-Cyclohexene-1-methanol is obtained at a temperature of 58° and a pressure of 0.3 mm as a colourless oil, MS: 94 (M–H$_2$O)$^+$.

Analysis for C$_7$H$_{12}$O: Calculated: C 74.97; H 10.78% Found : C 74.83; H 11.00%.

(i) [(S)-3-Cyclohexene-1-yl]methyl p-toluenesulphonate:

A solution of 10.48 g (55 mmol) of p-toluenesulphonyl chloride in 10 ml of pyridine is slowly added dropwise to a solution, cooled to −10°, of 5.6 g (50 mmol) of (S)-3-cyclohexene-1-methanol in 20 ml of pyridine. The solution is stirred at −10° for 64 hours, thereafter evaporated in a high vacuum and the residue is taken up in ether. The ether solution is washed in succession with 1N hydrochloric acid, water and saturated sodium bicarbonate solution and subsequently evaporated under reduced pressure. [(S)-3-Cyclohexen-1-yl]methyl p-toluenesulphonate is thereby obtained as a colourless oil; MS: 173 (M)$^+$.

(j) (S)-1-(Bromomethyl)-3-cyclohexene:

A mixture of 13.3 g (50 mmol) of [(S)-3-cyclohexen-1-yl]methyl p-toluenesulphonate and 13.0 g (150 mmol) of lithium bromide in 100 ml of absolute acetone is boiled under-reflux for 16 hours. Subsequently, the precipitate is filtered off, the filtrate is evaporated and the residue is taken up in absolute ether. The ether solution is filtered and evaporated. There is obtained (S)-1-(bromomethyl)-3-cyclohexene, MS: 174 (M)$^+$, as a colourless oil which is used directly in the following step.

(k) (2S,5R)-2-[(S)-3-Cyclohexen-1-ylmethyl]-2,5-dihydro-5-isopropyl-3,6-dimethoxypyrazine:

A solution, cooled to −78°, of 1.78 ml (10 mmol) of (2R)-(−)-2,5-dihydro-3,6-dimethoxy-2-isopropylpyrazine in 5 ml of absolute tetrahydrofuran is treated dropwise with 6.8 ml (11 mmol) of a solution of butyllithium in hexane. The reaction solution is left at −78° for 1 hour and at −20° for 1 hour and then again cooled to −78°. Subsequently, a solution of 1.75 g (10 mmol) of (S)-1-(bromomethyl)-3-cyclohexene in 5 ml of absolute tetrahydrofuran is added. After 2 hours at room temperature the solution is again cooled to −10°, treated with 5 ml of saturated ammonium chloride solution and extracted with ether. The organic phase is washed with water, dried over sodium sulphate and evaporated under reduced pressure. For purification, the residue is chromatographed twice on silica gel using a 9:1 mixture of toluene and ethyl acetate as the eluent. (2S,5R)-2-[(S)-3-Cyclohexen-1-ylmethyl]-2,5-dihydro-5-isopropyl-3,6-dimethoxypyrazine is obtained as a colourless oil; MS: 278 (M)⁺.

Analysis for $C_{16}H_{26}N_2O_2$: Calculated: C 69.03; H 9.41; N 10.06% Found : C 69.31; H 9.52; N 10.14%.

(1) Boc-3-[(S)-2-Cyclohexen-2-yl]-L-alanine methyl ester:

A mixture of 1.39 g (5 mmol) of (2S,5R)-2-[(S)-3-cyclohexen-1-ylmethyl]-2,5-dihydro-5-isopropyl-3,6-dimethoxypyrazine, 1.90 g (10 mmol) of p-toluenesulphonic acid, 10 ml of 0.25N hydrochloric acid and 5 ml of methanol is stirred at room temperature for 16 hours and then at 80° for 2 hours. Subsequently, the reaction mixture is evaporated under reduced pressure and the residue is dried in a high vacuum. The thus-obtained solid mass is suspended in 30 ml of dimethylformamide, treated with 1.70 g (7.8 mmol) of di-tert-butyl dicarbonate and 1.98 ml (14.3 mmol) of triethylamine and stirred at room temperature for 2 hours. The reaction mixture is thereafter evaporated in a high vacuum and the residue is partitioned between ether and water. The ether phase is dried over sodium sulphate and evaporated. The residue is chromatographed on silica gel using a 4:1 mixture of toluene and ethyl acetate as the eluent. There is obtained Boc-3-[(S)-2-cyclohexen-1-yl]-L-alanine methyl ester as a colourless oil; MS: 227 (M–$C_4H_8$)⁺.

Analysis for $C_{15}H_{25}NO_4$: Calculated: C 62.36; H 8.93; N 4.28% Found : C 62.05; H 9.02; N 4.15%.

Boc-3-[(R)-2-Cyclohexen-1-yl]-L-alanine methyl ester

In an analogous manner to that described above, starting from (S)-tetrahydro-4,4-dimethyl-2-oxo-3-furyl (R)-3-cyclohexene-1-carboxylate there is obtained Boc-3-[(R)-2-cyclohexen-1-yl]-L-alanine methyl ester as a colourless oil, MS: 227 (M–$C_4H_8$)⁺.

EXAMPLE 7

A solution of 32 mg (0.043 mmol) of tert-butyl [2-[[(S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulphonyl]-2-methylpropyl]carbamate in 2 ml of dioxan is treated with 2 ml (4 mmol) of 2N hydrochloric acid in dioxan while cooling with ice and stirred for 1 hour. Subsequently, the solution is lyophilized and there are obtained 30 mg of (S)-α-[(S)-α-[[[(2-amino-1,1-dimethylethyl)sulphonyl]methyl]hydrocinnamamido]-N-[(1S,2R,3S)-1-(cyclohexylmethyl)-3-cyclopropyl-2,3-dihydroxypropyl]imidazole-4-propionamide dihydrochloride as a colourless powder; MS: 646 (M+H)⁺.

EXAMPLE 8

A mixture of 300 mg (0.38 mmol) of benzyl [2-[[(S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulphonyl]-1,1-dimethylethyl]carbamate and 30 mg of palladium/carbon (10%) in 8 ml of acetic acid is hydrogenated at room temperature for 3 hours. Thereafter, the catalyst is filtered off, the reaction solution is evaporated and the residue obtained is lyophilized from water. There are obtained 240 mg of (S)-α-[(S)-α-[[(2-amino-2-methylpropyl)sulphonyl]methyl]hydrocinnamamido]-N-[(1S,2R,3S)-1-(cyclohexylmethyl)-3-cyclopropyl-2,3-dihydroxypropyl]imidazole-4-propionamide diacetate as a colourless, amorphous powder; MS: 646 (M+H)⁺.

EXAMPLE 9

In an analogous manner to that described in Example 8, by catalytically hydrogenating benzyl [2-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-p-fluorophenethyl]sulphonyl]-1,1-dimethylethyl]carbamate there is obtained (S)-α-[(S)-α-[[(2-amino-2-methylpropyl)sulphonyl]methyl]-p-fluorohydrocinnamamido]-N-[(1S,1R,3S)-1-(cyclohexylmethyl)-3-cyclopropyl-2,3-dihydroxypropyl] imidazole-4-propionamide diacetate as a colourless, amorphous powder; MS: 664 (M+H)⁺.

EXAMPLE 10

A solution of 2.82 g (about 3.8 mmol) of crude (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]-1-Boc-imidazole-4-propionamide and 0.35 g (2.55 mmol) of potassium carbonate in 20 ml of methanol is stirred at room temperature under argon for 1 hour. Thereafter, 0.33 g (6.1 mmol) of ammonium chloride is added and the mixture is stirred at room temperature for a further 15 minutes. The reaction mixture is subsequently evaporated under reduced pressure, the residue is taken up in 60 ml of ethyl acetate and this solution is washed in succession with 30 ml of water and 30 ml of saturated sodium chloride solution. The aqueous phases are back-extracted twice with 60 ml of ethyl acetate. The combined organic phases are dried over sodium sulphate and evaporated under reduced pressure. The residue is triturated in 15 ml of ether, then filtered off under suction and, for further purification, chromatographed on 150 g of silica gel using a 4:1:0.1 mixture of methylene chloride, methanol and ammonia as the eluent. There are obtained 1.13 g of (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]-imidazole-4-propionamide as a colourless solid; MS: 631 (M+H)⁺.

EXAMPLE 11

The following compounds were prepared in an analogous manner to that described in Example 10:

From (S)-α-[(S)-α-[(tert-butylsulphonyl)methyl] hydrocinnamamido]-N-[(1S,2R,3S)-3-cyclopropyl-1-[(4,4-difluorocyclohexyl)methyl]-2,3-dihydroxypropyl]-1-Boc-imidazole-4-propionamide the (S)-α-[(S)-α- [(tert-butylsulphonyl)methyl] hydrocinnamamido]-N- [(1S,2R,3S)-3-cyclopropyl-1-[(4,4-difluorocyclohexyl)methyl]-2,3-dihydroxypropyl]imidazole-4-propionamide as a colourless solid, MS: 667 (M+H)⁺;

from (S)-α-[(S)-α-[(tert-butylsulphonyl)methyl] hydrocinnamamido]-N-[(1S,2R,3S)-1-[[(RS)-4-hydroxycyclohexyl]methyl]-3-cyclopropyl-2,3-dihydroxypropyl]-1-Boc-imidazole-4-propionamide the (S)-α-[(S)-α-[(tert-butylsulphonyl)methyl] hydrocinnamamido]-N-[(1S,2R,3S)-1-[[(RS)-4-hydroxycyclohexyl]methyl]-3-cyclopropyl-2,3-dihydroxypropyl]imidazole-4-propionamide as a colourless solid, MS: 647 (M+H)⁺;

from (S)-α-[(S)-α-[(tert-butylsulphonyl)methyl] hydrocinnamamido]-N-[(1S,2R,3S)-3-cyclopropyl-1-(p-fluorobenzyl)-2,3-dihydroxypropyl]-1-Boc-imidazole-4-propionamide the (S)-α-[(S)-α-[(tert-butylsulphonyl)methyl]hydrocinnamamido]-N-[(1S,2R,3S)-3-cyclopropyl-1-(p-fluorobenzyl)-2,3- dihydroxypropyl]-imidazole-4-propionamide as a colourless solid, MS: 643 (M+H)⁺;

from (S)-α-[(S)-α-[(tert-butylsulphonyl)methyl] hydrocinnamamido]-N-[(1S,2R,3S)-1-[(S)-3-cyclohexen-1-ylmethyl]-3-cyclopropyl-2,3-dihydroxypropyl]-1-Boc-imidazole-4-propionamide the (S)-α-[(S)-α-[(tert-butylsulphonyl)methyl] hydrocinnamamido]-N-[(1S,2R,3S)-1-[(S)-3-cyclohexen-1-ylmethyl]-3-cyclopropyl-2,3-dihydroxypropyl]imidazole-4-propionamide as an amorphous solid, MS: 737 (M+H+matrix)⁺;

from (S)-α-[(S)-α-[(tert-butylsulphonyl)methyl] hydrocinnamamido]-N-[(1S,2R,3S)-1-[(R)-3-cyclohexen-1-ylmethyl]-3-cyclopropyl-2,3-dihydroxypropyl]-1-Boc-imidazole-4-propionamide the (S)-α-[(S)-α-[(tert-butylsulphonyl)methyl] hydrocinnamamido]-N-[(1S,2R,3S)-1-[(R)-3-cyclohexen-1-ylmethyl]-3-cyclopropyl-2,3-dihydroxypropyl]imidazole-4-propionamide as an amorphous solid, MS: 629 (M)⁺;

from (S)-α-[(S)-α-[(tert-butylsulphonyl)methyl] hydrocinnamamido]-N-[(1S,2R,3RS)-1-(cyclohexylmethyl)-2,3,4-trihydroxybutyl]-1-Boc-imidazole-4-propionamide the (S)-α-[(S)-α-[(tert-butylsulphonyl)methyl]hydrocinnamamido]-N-[(1S, 2R,3RS)-1-(cyclohexylmethyl)-2,3,4-trihydroxybutyl] -imidazole-4-propionamide as a colourless solid, MS: 621 (M+H)⁺;

from (S)-α-[(S)-α-[(tert-butylsulphonyl)methyl] hydrocinnamamido]-N-[(1S,2R,3R or S,4R or S)-1-(cyclohexylmethyl)-2,3,4-trihydroxyhexyl]-1-Boc-imidazole-4-propionamide the (S)-α-[(S)-α-[(tert-butylsulphonyl)methyl]hydrocinnamamido]-N-[(1S, 2R,3R or S,4R or S)-1-(cyclohexylmethyl)-2,3,4-trihydroxyhexyl]-imidazole-4-propionamide as a crystalline solid, MS: 649 (M+H)⁺.

EXAMPLE 12

A mixture of 100 mg (0.16 mmol) of (S)-α-[(S)-α-[(tert-butylsulphonyl)methyl]hydrocinnamamido]-N-[(1S,2R,3S) -1-(cyclohexylmethyl)-3-cyclopropyl-2,3-dihydroxypropyl] imidazole-4-propionamide, 46 mg (0.24 mmol) of ethyl 2-(bromomethyl)acrylate and 0.044 ml (0.32 mmol) of triethylamine in 3 ml of methylene chloride is stirred at room temperature under argon for 24 hours. Subsequently, the reaction mixture is evaporated and, for purification, the residue is chromatographed on 30 g of silica gel using a 14:1:0.1 mixture of methylene chloride, methanol and ammonia as the eluent. There are obtained mg of ethyl 4-[(S)-2-[(S)-α-[(tert-butylsulphonyl)methyl] hydrocinnamamido]-2-[[(1S,2R,3S)-1-(cyclohexylmethyl)-3-cyclopropyl-2,3-dihydroxypropyl]carbamoyl]ethyl]-α-methyleneimidazole-1-propionate as an amorphous solid; MS: 743 (M+H)⁺.

EXAMPLE 13

The following compounds were manufactured in an analogous manner to that described in Example 12:

From (S)-α-[(S)-α-[(tert-butylsulphonyl)methyl] hydrocinnamamido]-N-[(1S,2R,3S)-1-(cyclohexylmethyl)-3-cyclopropyl-2,3-dihydroxypropyl]imidazole-4-propionamide and 1-(acetyloxy)ethyl-4-nitrophenylcarbonate (J. Med. Chem. 1988, 31, 318) the ethylideneacetate 4-[(S)-2-[(S)-α-[(tert-butylsulphonyl)methyl] hydrocinnamamido]-2-[[(1S,2R,3S)-1-(cyclohexylmethyl)-3-cyclopropyl-2,3-dihydroxypropyl]carbamoyl]ethyl]imidazole-1-carboxylate as an amorphous solid, MS: 761 (M+H)⁺;

from (S)-α-[(S)-α-[(tert-butylsulphonyl)methyl] hydrocinnamamido]-N-[(1S,2R,3S)-1-(cyclohexylmethyl)-3-cyclopropyl-2,3-dihydroxypropyl]imidazole-4-propionamide and (1-chloroethyl)ethyl carbonate the ethyl 4-[(S)-2-[(S)-α-[(tert-butylsulphonyl)methyl]hydrocinnamamido]-2-[[(1S,2R,3S)-1-(cyclohexylmethyl)-3-cyclopropyl-2,3-dihydroxypropyl]carbamoyl]ethyl]imidazole-1-carboxylate, MS: 703 (M+H)⁺, and the ethyl 5-[(S)-2-[(S)-α-[(tert-butylsulphonyl)methyl] hydrocinnamamido]-2-[[(1S,2R,3S)-1-(cyclohexylmethyl)-3-cyclopropyl-2,3-dihydroxypropyl]carbamoyl]ethyl]imidazole-1-carboxylate, MS: 703 (M+H)⁺, each as a colourless oil;

from (S)-α-[(S)-α-[(tert-butylsulphonyl)methyl] hydrocinnamamido]-N-[(1S,2R,3S)-1-(cyclohexylmethyl)-3-cyclopropyl-2,3-dihydroxypropyl]imidazole-4-propionamide and allyl chloroformate the allyl 4-[(S)-2-[(S)-α-[(tert-butylsulphonyl)methyl]hydrocinnamamido]-2-[[(1S, 2R,3S)-1-(cyclohexylmethyl)-3-cyclopropyl-2,3-dihydroxypropyl]carbamoyl]ethyl]imidazole-1-carboxylate as an amorphous solid, MS: 715 (M+H)⁺, from (S)-α-[(S)-α-[(tert-butylsulphonyl)methyl] hydrocinnamamido]-N-[(1S,2R,3S)-1-(cyclohexylmethyl)-3-cyclopropyl-2,3-dihydroxypropyl]imidazole-4-propionamide and triphenylchloromethane the (S)-α-[(S)-α-[(tert-butylsulphonyl)methyl]hydrocinnamamido]-N-[(1S, 2R,3S)-1-(cyclohexylmethyl)-3-cyclopropyl-2,3-dihydroxypropyl]-1-tritylimidazole-4-propionamide as an amorphous solid, MS: 873 (M+H)⁺.

EXAMPLE 14

A suspension of 250 mg (0.4 mmol) of (S)-α-[(S)-α-[(tert-butylsulphonyl)methyl]hydrocinnamamido]-N-[(1S, 2R,3S)-1-(cyclohexylmethyl)-3-cyclopropyl-2,3-dihydroxypropyl]imidazole-4-propionamide, 60 mg of 18-crown-6, 250 mg of potassium carbonate and 2 ml of chloromethyl pivalate is stirred at room temperature overnight. Thereafter, the reaction mixture is taken up in ethyl acetate and the ethyl acetate solution is washed with saturated ammonium chloride solution. After drying over sodium sulphate the solution is evaporated under reduced pressure and subsequently, for purification, the crude product obtained (1.3 g) is chromatographed on 120 g of silica gel using a 200:10:1 mixture of methylene chloride, methanol and ammonia as the eluent. There are obtained 145 mg of [4-[(S)-2-[(S)-α-[(tert-butylsulphonyl)methyl] hydrocinnamamido]-2-[[(1S,2R,3S)-1-(cyclohexylmethyl)-3-cyclopropyl-2,3-dihydroxypropyl]carbamoyl]ethyl] imidazol-1-yl]methyl pivalate as a colourless solid; MS: 745 (M+H)⁺.

EXAMPLE 15

10.4 ml (2.08 mmol) of a 0.2N methanolic iodine solution and 2.4 ml (0.48 mmol) of 0.2N sodium hydroxide solution are simultaneously added dropwise at 0° while stirring to a mixture of 630 mg (1 mmol) of (S)-α-[(S)-α-[(tert-butylsulphonyl)methyl]hydrocinnamamido]-N-[(1S,2R,3S) -1-(cyclohexylmethyl)-3-cyclopropyl-2,3-dihydroxypropyl] imidazole-4-propionamide and 20 ml (4 mmol) of 0.2N sodium hydroxide solution in 20 ml of methanol. The colourless reaction mixture is stirred at 0° for 5 minutes and thereafter at room temperature for 2.5 hours. Subsequently, the mixture is diluted with 25 ml of water and extracted twice with 80 ml of ethyl acetate each time. The combined organic phases are washed with saturated sodium chloride solution, dried over sodium sulphate and evaporated under reduced pressure. For purification, the residue (750 mg) is chromatographed using a 15:1 mixture of methylene chloride and methanol as the eluent. There are obtained 504 mg of (S)-α-[(S)-α-[(tert-butylsulphonyl)methyl] hydrocinnamamido]-N-[(1S,2R,3S)-1-(cyclohexylmethyl)-3-cyclopropyl-2,3-dihydroxypropyl]-5-iodoimidazole-4-propionamide, MS: 757 (M+H)$^+$, and 38 mg of (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]-2,5-iodoimidazole-4-propionamide, MS: 883 (M+H)$^+$, each as a colourless solid.

EXAMPLE 16

A mixture of 355 mg (0.58 mmol) of (S)-α-amino-N-[(1S,2R,3S)-1-(cyclohexylmethyl)-3-cyclopropyl-2,3-dihydroxypropyl]-1-tritylimidazole-4-propionamide, 95 mg (0.58 mmol) of benzimidazole-2-carboxylic acid [Chem. Ber. 45, 3489 (1912)], 256 mg (0.58 mmol) of BOP and 0.12 ml (0.58 mmol) of Hünig base in 50 ml of acetonitrile is stirred at room temperature for 20 hours. Thereafter, the reaction mixture is evaporated under reduced pressure, the residue is taken up in 60 ml of ethyl acetate and washed twice with 20 ml of saturated potassium hydrogen carbonate solution. After drying the organic phase over sodium sulphate the solvent is evaporated under reduced pressure. For purification, the residue is chromatographed on 30 g of silica gel using a 15:1 mixture of methylene chloride and methanol as the eluent. There are obtained 379 mg of N-[(S)-1-[[(1S,2R,3S)-1-(cyclohexylmethyl)-3-cyclopropyl-2,3-dihydroxypropyl]carbamoyl]-2-(1-tritylimidazol-4-yl)ethyl]-2-benzimidazolecarboxamide as a colourless foam; MS: 751 (M+H)$^+$.

The (S)-α-amino-N-[(1S,2R,3S)-1-(cyclohexylmethyl)-3-cyclopropyl-2,3-dihydroxypropyl]-1-tritylimidazole-4-propionamide used as the starting material was prepared as follows:

(a) tert-Butyl (4S,5R)-4-(cyclohexylmethyl)-5-[(S)-cyclopropylhydroxymethyl]-2,2-dimethyl-3-oxazolidinecarboxylate and tert-butyl (4S,5R)-4-(cyclohexylmethyl)-5-[(R)-cyclopropylhydroxymethyl]-2,2-dimethyl-3-oxazolidinecarboxylate:

A solution of 3.21 g (9.8 mmol) of tert-butyl (4S,5R)-4-(cyclohexylmethyl)-5-formyl-2,2-dimethyl-3-oxazolidinecarboxylate (WO 87/05302) in 25 ml of tetrahydrofuran is added dropwise at about 15° to a solution of the Grignard compound prepared from 3.94 ml (49 mmol) of cyclopropyl bromide and 1.2 g (0.049 gram atom) of magnesium shavings in 22 ml of tetrahydrofuran and the reaction mixture is subsequently stirred at room temperature under argon for 16 hours. Thereafter, the reaction mixture is poured into 40 ml of an ice-cold, saturated ammonium chloride solution and extracted twice with 50 ml of ethyl acetate each time. The ethyl acetate extracts are washed with 40 ml of ice-cold, saturated ammonium chloride solution, combined, dried over sodium sulphate and evaporated under reduced pressure. For purification, the residue (4.33 g) is chromatographed over a column of 110 g of silica gel, prepared with toluene and 1% triethylamine, using a 95:5 mixture of toluene and ethyl acetate as the eluent. There are obtained 1.9 g of tert-butyl (4S,5R)-4-(cyclohexylmethyl)-5-[(S)-cyclopropylhydroxymethyl]-2,2-dimethyl-3-oxazolidinecarboxylate, MS: 368 (M+H)$^+$, and 0.5 g of tert-butyl (4S,5R)-4-(cyclohexylmethyl)-5-[(R)-cyclopropylhydroxymethyl]-2,2-dimethyl-3-oxazolidinecarboxylate, MS: 368 (M+H)$^+$, each as a colourless oil.

(b) (1S,2R,3S)-3-Amino-4-cyclohexyl-1-cyclopropyl-1,2-butanediol:

1.42 g (3.86 mmol) of tert-butyl (4S,5R)-4-(cyclohexylmethyl)-5-[(S)-cyclopropylhydroxymethyl]-2,2-dimethyl-3-oxazolidinecarboxylate dissolved in 15 ml of methanol and 10 ml of water are treated with 4 ml of 7.5N hydrochloric acid and stirred at 50° for 3 hours. The reaction solution is cooled to 3° in an ice bath, treated dropwise with 4 ml of 7.5N sodium hydroxide solution and stirred for 1 hour. The suspension obtained is evaporated under reduced pressure, the water is removed azeotropically twice with 10 ml of toluene and the residue is stirred up three times with 10 ml of a 95:5 mixture of methylene chloride and methanol. The insoluble residue is filtered off and the filtrate is evaporated under reduced pressure. The crude product obtained (1.14 g) is suspended in 15 ml of ether and thereafter filtered off. There is obtained 0.58 g of (1S,2R,3S)-3-amino-4-cyclohexyl-1-cyclopropyl-1,2-butanediol as colourless crystals, m.p. 141°–142°.

(c) (S)-N-[(1S,2R,2S)-1-(Cyclohexylmethyl)-3-cyclopropyl-2,3-dihydroxypropyl]-1-trityl-α-(tritylamino)imidazole-4-propionamide:

A mixture of 0.65 g (2.86 mmol) of (1S,2R,3S)-3-amino-4-cyclohexyl-1-cyclopropyl-1,2-butanediol, 1.27 g (2.86 mmol) of BOP, 1.85 g (2.86 mmol) of ditrityl-L-histidine (Tetrahedron Lett. 1987, 6031) and 0.59 ml (2.86 mmol) of Hünig base in 25 ml of acetonitrile is stirred at room temperature for 6 hours. Subsequently, the reaction mixture is evaporated under reduced pressure and the residue obtained is taken up in 150 ml of ethyl acetate, washed twice with 50 ml of saturated potassium hydrogen carbonate solution and the organic phase is dried over sodium sulphate. After evaporation of the solvent the crude product is purified by chromatography on 120 g of silica gel using a 40:1 mixture of methylene chloride and methanol as the eluent. There are obtained 1.52 g of (S)-N-[(1S,2R,3S)-1-(cyclohexylmethyl)-3-cyclopropyl-2,3-dihydroxypropyl]-1-trityl-α-(tritylamino)imidazole-4-propionamide as a colourless foam; MS: 849 (M+H)$^+$.

(d) (S)-α-Amino-N-[(1S,2R,3S)-1-(cyclohexylmethyl)-3-cyclopropyl-2,3-dihydroxypropyl]-1-tritylimidazole-4-propionamide:

A solution of 1.52 g (1.79 mmol) of (S)-N-[(1S,2R,3S)-1-(cyclohexylmethyl)-3-cyclopropyl-2,3-dihydroxypropyl]-1-trityl-α-(tritylamino)imidazole-4-propionamide in a mixture of 95.5 ml of methylene chloride, 3 ml of methanol and 1.5 ml of trifluoroacetic acid is stirred at room temperature for 5 minutes. Subsequently, 150 ml of 2N potassium bicarbonate solution and 150 ml of methylene chloride are added. The organic phase is separated, dried over sodium sulphate and evaporated. For purification, the residue is chromatographed on 100 g of silica gel using a 150:10:0.1 mixture of methylene chloride, methanol and ammonia as the eluent. There are obtained 1.03 g of (S)-α-amino-N-[(1S,2R,3S)-1-(cyclohexylmethyl)-3-cyclopropyl-2,3-dihydroxypropyl]-1-tritylimidazole-4-propionamide as a colourless foam; MS: 607 (M+H)$^+$.

EXAMPLE 17

The following compounds were manufactured in an analogous manner to that described in Example 16:

From (S)-α-amino-N-[(1S,2R,3S)-1-(cyclohexylmethyl)-3-cyclopropyl-2,3-dihydroxypropyl]-1-tritylimidazole-4-propionamide and indole-2-carboxylic acid the N-[(S)-1-[[(1S,2R,3S)-1-(cyclohexylmethyl)-3-cyclopropyl-2,3-dihydroxypropyl]carbamoyl]-2-(1-tritylimidazol)-4-ylethyl]indole-2-carboxamide;

from (S)-α-amino-N-[(1S,2R,3S)-1-(cyclohexylmethyl)-3-cyclopropyl-2,3-dihydroxypropyl]-1-tritylimidazole-4-propionamide and 5-hydroxyindole-2-carboxylic acid the N-[(S)-1-[[(1S,2R,3S)-1-(cyclohexylmethyl)-3-cyclopropyl-2,3-dihydroxypropyl]carbamoyl]-2-(1-tritylimidazol)-4-ylethyl]-5-hydroxyindole-2-carboxamide;

from (S)-α-amino-N-[(1S,2R,3S)-1-(cyclohexylmethyl)-3-cyclopropyl-2,3-dihydroxypropyl]-1-tritylimidazole-4-propionamide and benzothiazole-2-carboxylic acid (Chem. Ber. 37, 3731) the (S)-α-benzothiazolecarboxamido-N-[(1S,2R,3S)-1-(cyclohexylmethyl)-3-cyclopropyl-2,3-dihydroxypropyl]-1-tritylimidazole-4-propionamide;

from (S)-α-amino-N-[(1S,2R,3S)-1-(cyclohexylmethyl)-3-cyclopropyl-2,3-dihydroxypropyl]-1-tritylimidazole-4-propionamide and pyrrole-2-carboxylic acid the (S)-N-[(1S,2R,3S)-1-(cyclohexylmethyl)-3-cyclopropyl-2,3-dihydroxypropyl]-α-pyrrole-2-carboxamido-1-tritylimidazole-4-propionamide;

from (S)-α-amino-N-[(1S,2R,3S)-1-(cyclohexylmethyl)-3-cyclopropyl-2,3-dihydroxypropyl]-1-tritylimidazole-4-propionamide and α-benzyl-phenylpropionic acid (Ann. Chem. 691, 61) the (S)-N-[(1S,2R,3S)-1-(cyclohexylmethyl)-3-cyclopropyl-2,3-dihydroxypropyl]-α-(2,2-dibenzylacetamido)-1-tritylimidazole-4-propionamide, $R_f$=0.25 (methylene chloride/methanol 20:1);

from (S)-α-amino-N-[(1S,2R,3S)-1-(cyclohexylmethyl)-3-cyclopropyl-2,3-dihydroxypropyl]-1-tritylimidazole-4-propionamide and 2-ethyl (RS)-3,4-dihydro-2,3-(1H)-isoquinolinedicarboxylate (EPA 0189203) the ethyl (RS)-3-(RS)-1-[[(1S,2R,3S)-1-(cyclohexylmethyl)-3-cyclopropyl-2,3-dihydroxypropyl]carbamoyl]-2-(1-tritylimidazol)-4-ylethyl]-3,4-dihydro-2(1H)-isoquinolinecarboxylate, Rf=0.65 and 0.6 ((methylene chloride/methanol/ammonia 150:10:0.1).

EXAMPLE 18

The following compounds were manufactured in an analogous manner to that described in Example 16:

From (R or S)-α-amino-N-[(1S,2R,3S)-1-(cyclohexylmethyl)-3-cyclopropyl-2,3-dihydroxypropyl]-4-thiazolepropionamide and indole-2-carboxylic acid the N-[(R or S)-1-[[(1S,2R,3S)-1-(cyclohexylmethyl)-3-cyclopropyl-2,3-dihydroxypropyl]carbamoyl]-2-(4-thiazolyl)ethyl]indole-2-carboxamide as a colourless solid, MS: 525 (M+H)$^+$; from (R or S)-α-amino-N-[(1S,2R,3S)-1-(cyclohexylmethyl)-3-cyclopropyl-2,3-dihydroxypropyl]-4-thiazolepropionamide and benzimidazole-2-carboxylic acid the N-[(R or S)-1-[[(1S,2R,3S)-1-(cyclohexylmethyl)-3-cyclopropyl-2,3-dihydroxypropyl]carbamoyl]-2-(4-thiazolyl)ethyl]-2-benzimidazolecarboxamide as a colourless solid, MS: 526 (M+H)$^+$.

The (R)- and (S)-α-amino-N-[(1S,2R,3S)-1-(cyclohexylmethyl)-3-cyclopropyl-2,3-dihydroxypropyl]-4-thiazolepropionamide used as the starting material was prepared as follows:

(a) tert-Butyl [(RS)-1-[[(1S,2R,3S)-1-(cyclohexylmethyl)-3-cyclopropyl-2,3-dihydroxypropyl]carbamoyl]-2-4-thiazolyl)ethyl]carbamate (1:1 epimer mixture):

In a manner analogous to the procedure described in Example 16(c), by condensing (RS)-Boc-3-(4-thiazolyl)alanine, prepared according to the synthesis described in EPA 0274259, and 3-amino-4-cyclohexyl-1-cyclopropyl-1,2-butanediol there is obtained tert-butyl [(RS)-1-[[(1S,2R,3S)-1-(cyclohexylmethyl)-3-cyclopropyl-2,3-dihydroxypropyl]carbamoyl]-2-(4-thiazolyl)ethyl]carbamate (1:1 epimer mixture) as a colourless solid; MS: 482 (M+H)$^+$.

(b) (R)- and (S)-α-Amino-N-[(1S,1R,3S)-1-cyclohexylmethyl)-3-cyclopropyl-2,3-dihydroxypropyl]-4-thiazolepropionamide:

A mixture of 900 mg (1.87 mmol) of tert-butyl [(RS)-1-[[(1S,2R,3S)-1-(cyclohexylmethyl)-3-cyclopropyl-2,3-dihydroxypropyl]carbamoyl]-2-(4-thiazolyl)ethyl]carbamate (1:1 epimer mixture) and 9.3 ml of 2N hydrochloric acid in 30 ml of methanol is heated to reflux for 3 hours. After the usual working-up the product is chromatographed on 90 g of silica gel using a 150:10:1 mixture of methylene chloride, methanol and ammonia as the eluent in order to separate the epimers. There are obtained 410 mg of the less polar epimer Rf=0.2 (methylene chloride/methanol/ammonia 150:10:1), MS: 382 (M+H)$^+$, and 293 mg of the more polar epimer, Rf=0.15 (methylene chloride/methanol/ammonia 150:10:1), MS: 382 (M+H)$^+$.

EXAMPLE 19

A mixture of 200 mg (0.55 mmol) of (S)-α-amino-N-[(1S,2R,3S)-1-(cyclohexylmethyl)-3-cyclopropyl-2,3-dihydroxypropyl]imidazole-4-propionamide, 174 mg (0.57 mmol) of (RS)-α-(sulphonylmethyl)hydrocinnamic acid guanidine salt, 95 mg (0.7 mmol) of HOBT, 62 mg (0.61 mmol) of triethylamine and 231 mg (0.61 mmol) of HBTU in 50 ml of dimethylformamide is stirred at room temperature overnight. Thereafter, the reaction mixture is evaporated to dryness in a high vacuum and, for purification, the crude product obtained is chromatographed on 50 g of silica gel with a 9:1 to 1:1 mixture of water and methanol as the eluent. This chromatography is carried out again in order to separate the two epimers obtained. After lyophilization from dioxan/water there are obtained 81 mg of the less polar (R or S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropanesulphonic acid guanidine salt and 40 mg of the more polar (S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropanesulphonic acid guanidine salt, each as a colourless powder.

The (S)-α-amino-N-[(1S,2R,3S)-1-(cyclohexylmethyl)-3-cyclopropyl-2,3-dihydroxypropyl]imidazole-4-propionamide used as the starting material was prepared as follows:

A mixture of 343 mg (1.51 mmol) of (1S,2R,3S)-3-amino-4-cyclohexyl-1-cyclopropyl-1,2-butanediol, 995 mg (1.66 mmol) of (Fmoc)$_2$His-OH, 0.21 ml (1.61 mmol) of 4-ethylmorpholine, 449 mg (3.22 mmol) of HOBT and 347 mg (1.81 mmol) of EDC in 20 ml of dimethylformamide is left to stand at room temperature overnight. Thereafter, the reaction mixture is evaporated in a high vacuum, the residue is poured into a mixture of ice and 90 ml of sodium bicarbonate solution and extracted three times with 150 ml of ethyl acetate each time. The three ethyl acetate extracts are washed in succession with 70 ml of saturated ammonium chloride solution, 70 ml of 2N sodium bicarbonate solution and 70 ml of saturated sodium chloride solution, combined, dried over magnesium sulphate, filtered and evaporated. The crude product obtained is stirred at room temperature for 3 hours in 60 ml of methylene chloride and 2 ml of piperidine. Then, the reaction mixture is evaporated and the residue is triturated with 50 ml of hexane and filtered off. The filtrate is chromatographed on 70 g of silica gel with a 65:10:1 mixture of methylene chloride, methanol and ammonia as the eluent, whereby there are obtained 390 mg of (S)-α-amino-N-[(1S,2R,3S)-1-(cyclohexylmethyl)-3-cyclopropyl-2,3-dihydroxypropyl]imidazole-4-propionamide as a colourless foam; MS: 365 (M+H)$^+$.

The (RS)-α-(sulphonylmethyl)hydrocinnamic acid guanidine salt used as the starting material was prepared as follows:

(a) Ethyl (RS)-α-(sulphonylmethyl)hydrocinnamate guanidine salt:

5.06 g (28 mmol) of guanidine carbonate are added at −10° to a solution of 4.73 g (16.2 mmol) of crude ethyl 2-benzyl-3-chlorosulphonyl-propionate, prepared according to the procedure described in EPA 0236734, in 150 ml of methylene chloride and 40 ml of dimethylformamide. The reaction mixture is stirred at room temperature overnight and thereafter evaporated. The residue is partitioned between methylene chloride and water, the aqueous phase is separated, evaporated under reduced pressure and the residue obtained is chromatographed on 50 g of silica gel using a 9:1 to 1:1 mixture of water and methanol as the eluent. The product obtained is recrystallized from a mixture of methanol and ether. There are obtained 3.29 g of ethyl (RS)-α-(sulphonylmethyl)hydrocinnamate guanidine salt as colourless crystals.

Analysis for $C_{12}H_{16}O_5S \cdot CH_5N_3$: Calculated: C 47.12; H 6.39; N 12.68; S 9.67% Found : C 47.03; H 6.39; N 12.68; S 9.51%.

(b) (RS)-α-(Sulphonylmethyl)hydrocinnamic acid guanidine salt:

A solution of 3.11 g (9.4 mmol) of ethyl (RS)-α-(sulphonylmethyl)hydrocinnamate guanidine salt in 400 ml of semi-concentrated hydrochloric acid is heated to reflux for 20 hours. Subsequently, the reaction solution is evaporated under reduced pressure and, for purification, the residue obtained is chromatographed on 50 g of silica gel using a 9:1 to 1:1 mixture of water and methanol as the eluent. After lyophilization from water there is obtained 0.6 g of (RS)-α-(sulphonylmethyl)hydrocinnamic acid guanidine salt as a colourless powder, MS: 243 (M−H)$^−$.

EXAMPLE 20

The following compounds were manufactured in an analogous manner to that described in Example 19:

From (S)-α-amino-N-[(1S,2R,3S)-1-(cyclohexylmethyl)-3-cyclopropyl-2,3-dihydroxypropyl]imidazole-4-propionamide and N-Boc-(2S,3R)-3-amino-2-hydroxy-4-phenylbutyric acid the tert-butyl [(1R,2S)-1-benzyl-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-2-hydroxyethyl]carbamate as an amorphous solid, MS: 642 (M+H)$^+$;

from (S)-α-amino-N-[(1S,2R,3S)-1-(cyclohexylmethyl)-3-cyclopropyl-2,3-dihydroxypropyl]imidazole-4-propionamide and 2-(S)-[(4-morpholinylcarbonyl)oxy]-3-phenylpropionic acid the (S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl 4-morpholinecarboxylate as an amorphous solid, MS: 626 (M+H)$^+$;

from (S)-α-amino-N-[(1S,2R,3S)-1-(cyclohexylmethyl)-3-cyclopropyl-2,3-dihydroxypropyl]imidazole-4-propionamide and 2-(S)-[(1-piperidinylcarbonyl)oxy]-3-phenylpropionic acid the (S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl 1-piperidinecarboxylate as an amorphous solid, MS: 625 (M+H)$^+$.

The phenylpropionic acids used as starting materials were prepared as follows:

2-(S)-[(4-Morpholinylcarbonyl)oxy]-3-phenylpropionic acid was obtained starting from methyl L-phenyllactate according to the procedure described in J. Med. Chem., 31, (1988), 2277.

2-(S)-[(1-piperidinylcarbonyl)oxy]-3-phenylpropionic acid was also obtained starting from methyl L-phenyllactate in analogy to the procedure described in J. Med. Chem., 31, (1988) 2277 by using piperidine instead of morpholine.

EXAMPLE 21

In an analogous manner to that described in Example 19, by condensing (S)-α-amino-N-[(1S,2R,3S)-1-(cyclohexylmethyl)-3-cyclopropyl-2,3-dihydroxypropyl]imidazole-4-propionamide with Fmoc-Phe-OH there was obtained 9H-fluoren-9-ylmethyl [(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl]carbamate which, by reaction with piperidine in methylene chloride, was converted into (S)-N-[(1S,2R,3S)-1-(cyclohexylmethyl)-3-cyclopropyl-2,3-dihydroxypropyl]-α-[(3-phenyl-L-alanyl)amino]imidazole-4-propionamide. Further condensation with Boc-D-Pro-OH, analogously to Example 19, yielded (R)-2-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl]carbamoyl]-1-pyrrolidinecarboxylic acid tert-butyl ester as an amorphous solid, MS: 709 (M+H)$^+$.

EXAMPLE 22

The following compounds were manufactured in an analogous manner to that described in Example 21:

From (S)-N-[(1S,2R,3S)-1-(cyclohexylmethyl)-3-cyclopropyl-2,3-dihydroxypropyl]-α-[(3-phenyl-L-alanyl)amino]imidazole-4-propionamide and 1-tert-butyl 4-hydrogen N-(tert-butoxycarbonyl)-N-[2-(1-tert-butoxyformamido)ethyl]-L-aspartate the di-tert-butyl
N-[(S)-1-(tert-butoxycarbonyl)-2-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl]carbamoyl]ethyl]ethylenedicarbamate as an amorphous solid, MS: 926 (M+H)$^+$;

from (S)-N-[(1S,2R,3S)-1-(cyclohexylmethyl)-3-cyclopropyl-2,3-dihydroxypropyl]-α-[(3-phenyl-L-alanyl)amino]imidazole-4-propionamide and L-pyroglutamic acid the (S)-N-[(1S,2R,3S)-1-(cyclohexylmethyl)-3-cyclopropyl-2,3-dihydroxypropyl]-α-[(S)-α-[(S)-5-oxo-2-pyrrolidinecarboxamido]hydrocinnamamido]imidazole-4-propionamide as an amorphous solid, MS: 623 (M+H)$^+$;

from (S)-N-[(1S,2R,3S)-1-(cyclohexylmethyl)-3-cyclopropyl-2,3-dihydroxypropyl]-α-[(3-phenyl-L-alanyl)amino]imidazole-4-propionamide and Boc-aminoisobutyric acid the tert-butyl [1-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl]carbamoyl]-1-methylethyl]carbamate as an amorphous solid, MS: 697 (M+H)$^+$;

from (S)-N-[(1S,2R,3S)-1-(cyclohexylmethyl)-3-cyclopropyl-2,3-dihydroxypropyl]-α-[(3-phenyl-L-alanyl)amino]imidazole-4-propionamide and N-(tert-butoxycarbonyl)-N-[2-[(tert-butoxycarbonyl)amino]ethyl]glycine (U.S. Pat. No. 4,145,337) the di-tert-butyl N-[[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl]carbamoyl]methyl]ethylenedicarbamate as an amorphous solid, MS: 813 (M+H)$^+$.

The 1-tert-butyl 4-hydrogen N-(tert-butoxycarbonyl)-N-[2-(1-tert-butoxyformamido)ethyl]-L-aspartate used as the starting material was prepared as follows:

(a) 4-Benzyl 1-tert-butyl N-[(1-tert-butoxyformamido)acetyl]-L-aspartate:

A mixture of 12 g (54 mmol) of L-aspartic acid 4-benzyl ester, 10 ml of concentrated sulphuric acid and 100 ml of liquid isobutylene in 100 ml of dry dioxan is stirred at room temperature overnight in a pressure flask. Thereafter, the solution is added dropwise to 500 ml of ice-cold 1N sodium hydroxide solution. The aqueous phase is extracted three times with ether. The combined organic phases are dried over sodium sulphate and evaporated. The viscous oil obtained (13.85 g) is dissolved in 250 ml of dry dimethylformamide and stirred at room temperature for 4 hours with 9.55 g (54.5 mmol) of Boc-glycine, 20.7 g (54.5 mmol) of HBTU and 6 ml (54.5 mmol) of N-methylmorpholine. Subsequently, the reaction mixture is evaporated in a high vacuum and the residue obtained is taken up in ether. The organic phase is washed with 5% sodium carbonate solution and water, thereafter dried over sodium sulphate and evaporated under reduced pressure. The oily residue is chromatographed on silica gel using a 1:1 mixture of hexane and ether as the eluent. There is obtained 4-benzyl 1-tert-butyl N-[(1-tert-butoxyformamido)acetyl]-L-aspartate as a viscous oil; MS: 437 (M+H)$^+$.

(b) 4-Benzyl 1-tert-butyl N-[(1-tert-butoxyformamido)thioacetyl]-L-aspartate:

A solution of 14.8 g (33.9 mmol) of 4-benzyl 1-tert-butyl N-[(1-tert-butoxyformamido)acetyl]-L-aspartate and 6.9 g (17 mmol) of Lawesson reagent in 140 ml of dry toluene is heated to 100° for 2.5 hours. Thereafter, the solvent is distilled off under reduced pressure and the residue is boiled up three times with 500 ml of a 9:1 mixture of hexane and ether. The combined organic phases are evaporated and, for purification, the residue is chromatographed on silica gel using a 9:1 mixture of hexane and ether as the eluent, whereby there is obtained 4-benzyl 1-tert-butyl N-[(1-tert-butoxyformamido)thioacetyl]-L-aspartate as a viscous oil; MS: 452 (M)$^+$.

(c) 4-Benzyl 1-tert-butyl (E/Z)-N-[2-(1-tert-butoxyformamido)-1-(methylthio)ethylidene]-L-aspartate:

A mixture of 1.1 g (2.43 mmol) of 4-benzyl 1-tert-butyl N-[(1-tert-butoxyformamido)thioacetyl]-L-aspartate, 1.95 ml of methyl iodide and 0.92 g of potassium carbonate in 50 ml of acetone is stirred at room temperature overnight. Thereafter, the solvent is distilled off under reduced pressure and the residue is taken up in ether. The organic phase is washed with water, dried over sodium sulphate and evaporated. 4-Benzyl 1-tert-butyl N-[2-(1-tert-butoxyformamido)-1-(methylthio)ethylidene]-L-aspartate is obtained as a mixture of the E- and Z-isomers; MS: 467 (M+H)$^+$.

(d) 3-[(Benzyloxy)carbonyl]-N-[2-(1-tert-butoxyformamido)ethyl]-L-alanine tert-butyl ester:

A mixture of 0.5 g (1.1 mmol) of 4-benzyl 1-tert-butyl (E/Z)-N-[2-(1-tert-butoxyformamido)-1-(methylthio) ethylidene]-L-aspartate, 1.0 g of sodium cyanoborohydride and 0.5 ml of acetic acid in 10 ml of methanol is stirred at room temperature for 2 hours. Thereafter, the solvent is distilled off under reduced pressure and the residue is taken up in ether. The ether solution is washed with water, dried over sodium sulphate and subsequently evaporated. For purification, the residual oil is chromatographed on silica gel using a 1:1 mixture of cyclohexane and ethyl acetate as the eluent, whereby 3-[(benzyloxy)carbonyl]-N-[2-(1-tert-butoxyformamido)ethyl]-L-alanine tert-butyl ester is obtained as a viscous oil; MS: 423 (M+H)$^+$.

(e) 3-[(Benzyloxy)carbonyl]-N-[(tert-butoxy)carbonyl]-N-[2-(1-tert-butoxyformamido)ethyl]-L-alanine tert-butyl ester:

A mixture of 350 mg (0.83 mmol) of 3-[(benzyloxy)carbonyl]-N-[2-(1-tert-butoxyformamido)ethyl]-L-alanine tert-butyl ester, 10 mg (0.08 mmol) of dimethylaminopyridine, 1 ml (7.2 mmol) of triethylamine and 200 mg (0.9 mmol) of di-tert-butyl dicarbonate in 5 ml of acetonitrile is stirred at room temperature for 2 hours. Subsequently, the solvent is distilled off and the residue is taken up in ether. The ether solution is washed in succession with saturated sodium bicarbonate solution, water, 1M tartaric acid solution and water, dried over sodium sulphate and evaporated. For purification, the residue is chromatographed on silica gel using a 7:3 mixture of cyclohexane and ethyl acetate as the eluent. 3-[(Benzyloxy)carbonyl]-N-[(tert-butoxy)carbonyl]-N-[2-(1-tert-butoxyformamido)ethyl]-L-alanine tert-butyl ester is obtained as a viscous oil, MS: 523 (M+H)$^+$.

(f) 1-tert-butyl 4-hydrogen N-(tert-butoxycarbonyl)-N-[2-(1-tert-butoxyformamido)ethyl]-L-aspartate:

A suspension of 250 mg (0.48 mmol) of 3-[(benzyloxy)carbonyl]-N-[(tert-butoxy)carbonyl]-N-[-(1-tert-butoxyformamido)ethyl]-L-alanine tert-butyl ester and 50 mg of palladium/carbon (5%) in 10 ml of ethanol is hydrogenated at room temperature under normal pressure. Thereafter, the catalyst is filtered off and the solution is evaporated under reduced pressure. 1-tert-Butyl 4-hydrogen N-(tert-butoxycarbonyl)-N-[2-(1-tert-butoxyformamido)ethyl]-L-aspartate is obtained as a colourless foam: MS: 433 (M+H)$^+$.

EXAMPLE 23

A mixture of 147 mg (0.64 mmol) of (1S or R,2R,3S)-3-amino-4-cyclohexyl-1-cyclopropyl-1-fluoro-2-butanol, 365 mg (0.7 mmol) of (S)-1-(tert-butoxycarbonyl)-α-[(S)-α-[(tert-butylsulphonyl)methyl]hydrocinnamamido]imidazole-4-propionic acid, 71 mg (0.7 mmol) of triethylamine, 114 mg (0.7 mmol) of HOOBT and 285 mg (0.7 mmol) of HOBTU in 15 ml of dimethylformamide is stirred at room temperature overnight under argon. Thereafter, the dimethylformamide is evaporated in a high vacuum and the residue is taken up in 50 ml of ethyl acetate. The ethyl acetate phase is washed with 20 ml of saturated sodium bicarbonate solution and 20 ml of saturated sodium chloride solution, dried over sodium sulphate and evaporated under reduced pressure. There is obtained (S)-α-[(S)-α-[(tert-butylsulphonyl)methyl]hydrocinnamamido]-N-[(1S,2R,3S)-1-(cyclohexylmethyl)-3-cyclopropyl-3-fluoro- 2-hydroxypropyl]-1-Boc-imidazole-4-propionamide as a yellowish foam.

The (1S or R,2R,3S)-3-amino-4-cyclohexyl-1-cyclopropyl-1-fluoro-2-butanol used as the starting material was prepared as follows:

(a) tert-Butyl (4S,5R)-4-(cyclohexylmethyl)-5-[(S or R)-cyclopropylfluoromethyl]-2,2-dimethyl-3-oxazolidinecarboxylate and tert-butyl (4S,5R) 4-(cyclohexylmethyl)-5-[(R or S)-cyclopropylfluoromethyl]-2,2-dimethyl-3-oxazolidinecarboxylate:

A solution of 4.0 g (10.8 mmol) of tert-butyl (4S,5R)-4-(cyclohexylmethyl)-5-[(R)-cyclopropylhydroxymethyl]-2,2-dimethyl-3-oxazolidinecarboxylate in 50 ml of methylene chloride is treated dropwise at room temperature with 2.6 g (16.3 mmol) of diethylamino-sulphur trioxide. The reddish reaction solution is stirred at room temperature overnight and subsequently treated with 50 ml of water. The organic phase is separated, dried over sodium sulphate and evaporated. For purification and separation of the resulting epimers, the crude product obtained is chromatographed on 300 g of silica gel using methylene chloride as the eluent. There are obtained 1.90 g of the less polar epimer tert-butyl (4S,5R)-4-(cyclohexylmethyl)-5-[(S or R)-cyclopropylfluoromethyl]-2,2-dimethyl-3-oxazolidinecarboxylate, MS: 354 (M–CH$_3$)$^+$, and 1.08 g of the more polar epimer tert-butyl (4S,5R)-4-(cyclohexylmethyl)-5-[(R or S)-cyclopropylfluoromethyl]-2,2-dimethyl-3-oxazolidinecarboxylate, MS: 354 (M–CH$_3$)$^+$, each as a colourless oil.

(b) (1S or R,2R,3S)-3-Amino-4-cyclohexyl-1-cyclopropyl-1-fluoro-2-butanol:

A solution of 0.7 g (1.9 mmol) of tert-butyl (4S,5R)-4-(cyclohexylmethyl)-5-[(S or R)-cyclopropylfluoromethyl]-2,2-dimethyl-3-oxazolidinecarboxylate in 3 ml of methylene chloride is treated at room temperature with 30 ml of a freshly prepared 1:1 mixture of a 1M phenol solution and a 1M trimethylchlorosilane solution, both in methylene chloride. The reaction solution is stirred at room temperature for 36 hours, subsequently poured into 30 ml of ice-cold, saturated sodium carbonate solution and extracted twice with 100 ml of ethyl acetate each time. The organic phase is thereafter dried over sodium sulphate and evaporated under reduced pressure. For purification, the crude product (300 mg) is chromatographed on 100 g of silica gel using a 9:1:0.1 mixture of methylene chloride, isopropanol and ammonia as the eluent. There are obtained 230 mg of (1S or R,2R,3S)-3-amino-4-cyclohexyl-1-cyclopropyl1-fluoro-2-butanol as a colourless foam; MS: 230 (M+H)$^+$.

The (S)-1-(tert-butoxycarbonyl)-α-[(S)-α-[(tert-butylsulphonyl)methyl]hydrocinnamamido]imidazole-4-propionic acid used as the starting material was prepared as follows:

(c) Methyl (S)-α-[(S)-α-α-(tert-butylsulphonyl)methyl] hydrocinnamamido]imidazole-4-propionamide:

A mixture of 5.7 (20 mmol) of (S)-α-[(tert-butylsulphonyl)methyl]hydrocinnamic acid (EPA 0236734) 4.85 g (20 mmol) of L-histidine methyl ester dihydrochloride, 10.3 ml (81.7 mmol) of N-ethylmorpholine and 2.98 g (20 mmol) of HOBT in 85 ml of dimethylformamide is treated portionwise under argon at 0°–2° with 4.23 g (22 mmol) of EDC and subsequently stirred at room temperature overnight. Thereafter, the solvent is evaporated in a high vacuum, the residue is taken up in 100 ml of ethyl acetate and washed in sequence three times with 10 ml of 2N sodium bicarbonate solution, twice with 10 ml of saturated sodium chloride solution, twice with 10 ml of saturated ammonium chloride solution and twice with 5 ml of saturated sodium chloride solution. The aqueous phases are extracted three times with 20 ml of ethyl acetate and the pooled organic phases are dried over sodium sulphate and evaporated under reduced pressure. For purification, the crude product obtained (9.4 g) is chromatographed on 300 g of silica gel using a 95:5 mixture of methylene chloride and methanol as the eluent. There are obtained 8.6 g of methyl (S)-α-[(S)-α-[(tert-butylsulphonyl)methyl] hydrocinnamamido]imidazole-4-propionate as a colourless foam; MS: 436 (M+H)$^+$.

(d) (S)-1-(tert-Butoxycarbonyl)-α-[(S) α-[(tert-butylsulphonyl)methyl]hydrocinnamamido]imidazole-4-propionic acid:

A solution of 1.33 g (3.06 mmol) of methyl (S)-α-[(S)-α-[(tert-butylsulphonyl)methyl]hydrocinnamamido] imidazole-4-propionate in 4 ml of dioxan is treated dropwise with 3.98 ml of 1N sodium hydroxide solution while cooling with ice and stirred at this temperature for 30 minutes, whereby the methyl ester is converted quantitatively into the corresponding acid.

Subsequently, the reaction mixture is treated dropwise at 0–5° with a solution of 0.8 g (3.67 mmol) of di-tert-butyl dicarbonate in 4 ml of dioxan and, after removal of the ice bath, stirred at room temperature for 5 hours. Thereafter, 3.98 ml of 1N hydrochloric acid and 25 ml of water are added and the mixture is extracted with 55 ml of ethyl acetate. The aqueous phase is back-washed with 50 ml of ethyl acetate and the combined organic phases are washed twice with 25 ml of water, dried over sodium sulphate and evaporated under reduced pressure. There are obtained 1.98 g of (S)-1-(tert-butoxycarbonyl)-α-[(S)-α-[(tert-butylsulphonyl)methyl]hydrocinnamamido]imidazole-4-propionic acid as a foam; MS: 522 (M+H)$^+$.

EXAMPLE 24

The following compounds were manufactured in an analogous manner to that described in Example 23:

From (S)-1-(tert-butoxycarbonyl)-α-[(S)-α-[(tert-butylsulphonyl)methyl]hydrocinnamamido]imidazole-4-propionic acid and (1R or S,2R,3S)-3-amino-4-cyclohexyl-1-cyclopropyl-1-fluoro-2-butanol the (S)-α-[(S)-α-[(tert-butylsulphonyl)methyl] hydrocinnamamido]-N-[(1S,2R,3R)-1-(cyclohexylmethyl)-3-cyclopropyl-3-fluoro-2-hydroxypropyl]-1-Boc-imidazole-4-propionamide;

from (S)-1-(tert-butoxycarbonyl)-α-[(S)-α-[(tert-butylsulphonyl)methyl]hydrocinnamamido]imidazole-4-propionic acid and (1S,2R,3S)-3-amino-4-cyclohexyl-1-cyclopropyl-1,2-butanediol the (S)-α-[(S)-α-[(tert-butylsulphonyl)methyl] hydrocinnamamido]-N-[(1S,2R,3S)-1-(cyclohexylmethyl)-3-cyclopropyl-2,3-dihydroxypropyl]-1-Boc-imidazole-4-propionamide;

from (S)-1-(tert-butoxycarbonyl)-α-[(S)-α-](tert-butylsulphonyl)methyl]hydrocinnamamido]imidazole-4-propionic acid and (1S,2R,3S)-3-amino-1-azido-4-cyclohexyl-1-cyclopropyl-2-butanol the (S)-N-[(1S,2R,3S)-3-azido-1-(cyclohexylmethyl)-3-cyclopropyl-2-hydroxypropyl]-α-[(S)-α-[(tert-butylsulphonyl) methyl]hydrocinnamamido]-1-Boc-imidazole-4-propionamide;

from (S)-1-(tert-butoxycarbonyl)-α-[(S)-α-[(tert-butylsulphonyl)methyl]hydrocinnamamido]imidazole-4-propionic acid and (2R/S,3S,4S)-4-amino-5-cyclohexyl-2-cyclopropyl-2,3-pentanediol the (S)-α-

[(S)-α-[(tert-butylsulphonyl)methyl]hydrocinnamamido]-N-[(1S,2R,3R/S)-1-(cyclohexylmethyl)-3-cyclopropyl-2,3-dihydroxybutyl]-1-Boc-imidazole-4-propionamide.

The amines used as starting materials were prepared as follows:

(1R or S,2R,3S)-3-Amino-4-cyclohexyl-1-cyclopropyl-1-fluoro-2-butanol:

In an analogous manner to that described in Example 23(b), from tert-butyl (4S,5R)-4-(cyclohexylmethyl)-5-[(R or S)-cyclopropylfluoromethyl]-2,2-dimethyl-3-oxazolidinecarboxylate there was obtained, after cleavage of the Boc and isopropylidene protecting groups, (1R or S,2R, 3S)-3-amino-4-cyclohexyl-1-cyclopropyl-1-fluoro-2-butanol as a colourless oil, MS: 230 (M+H)⁺.

(1S,2R,3S)-3-Amino-1-azido-4-cyclohexyl-1-cyclopropyl-2-butanol:

(a) tert-Butyl (4S,5R)-4-(cyclohexylmethyl)-5-[(S)-cyclopropylazidomethyl]-2,2-dimethyl-3-oxazolidinecarboxylate:

A mixture of 1.63 g (25 mmol) of sodium azide, 1.5 ml of water and 10 ml of benzene is treated dropwise with 0.67 ml (12.5 mmol) of concentrated sulphuric acid while cooling with ice (<10°) and stirring. Thereafter, the mixture is cooled to 0°, the benzene phase is decanted off and dried over magnesium sulphate. The thus-obtained nitrogen hydride solution is added to a mixture of 368 mg (1 mmol) of tert-butyl (4S,5R)-4-(cyclohexylmethyl)-5-[(R)-cyclopropylhydroxymethyl]-2,2-dimethyl-3-oxazolidinecarboxylate and 289 mg (1.1 mmol) of triphenylphosphine in 5 ml of benzene. Subsequently, 0.15 ml (1.1 mmol) of diethyl azodicarboxylate is added and the reaction mixture is stirred at room temperature overnight under argon. Thereafter, the reaction mixture is evaporated and, for purification, the residue is chromatographed on 50 g of silica gel using a 3:1 mixture of toluene and ethyl acetate as the eluent. There are obtained 210 mg of tert-butyl (4S,5R)-4-(cyclohexylmethyl)-5-[(S)-cyclopropylazidomethyl]-2,2-dimethyl-3-oxazolidinecarboxylate, MS: 393 (M+H)⁺, as an oil which gradually crystallizes as well as 130 mg of educt.

(b) (1S,2R,3S)-3-Amino-1-azido-4-cyclohexyl-1-cyclopropyl-2-butanol:

In a manner analogous to the procedure described above for the preparation of (2RS,3R,4S)-4-amino-5-cyclohexyl-1,2,3-pentanetriol, by reacting tert-butyl (4S,5R)-4-(cyclohexylmethyl)-5-[(S)-cyclopropylazidomethyl]-2,2-dimethyl-3-oxazolidinecarboxylate there is obtained (1S,2R,3S)-3-amino-1-azido-4-cyclohexyl-1-cyclopropyl-2-butanol as an oil, MS: 253 (M+H)⁺.

(2R/S,3S,4S)-4-Amino-5-cyclohexyl-2-cyclopropyl-2,3-pentanediol (c) tert-Butyl (4S,5R)-4-(cyclohexylmethyl)-5-(cyclopropylcarbonyl)-2,2-dimethyl-3-oxazolidinecarboxylate:

A mixture of 500 mg (1.36 mmol) of tert-butyl (4S,5R)-4-(cyclohexylmethyl)-5-[(R)-cyclopropylhydroxymethyl]-2,2-dimethyl-3-oxazolidinecarboxylate and 750 mg (1.77 mmol) of 1,1-dihydro-1,1,1-triacetoxy-1,2-benziodoxol-3(1H)-one in 10 ml of methylene chloride is stirred at room temperature for 3 hours. Thereafter, 50 ml of ether and 20 ml of 2N sodium hydroxide solution are added and the mixture is stirred at room temperature for 1 hour. The organic phase is separated, washed with 20 ml of 2N sodium hydroxide solution, dried over sodium sulphate and evaporated. There are obtained 400 mg of tert-butyl (4S,5R)-4-(cyclohexylmethyl)-5-(cyclopropylcarbonyl)-2,2-dimethyl-3-oxazolidinecarboxylate as a yellow oil; MS: 366 (M+H)⁺.

(d) tert-Butyl (4S,5R)-4-(cyclohexylmethyl)-5-[(R/S)-1-cyclopropyl-1-hydroxyethyl-2,2-dimethyl-3-oxazolidinecarboxylate:

A solution of 400 mg (1.09 mmol) of tert-butyl (4S,5R)-4-(cyclohexylmethyl)-5-(cyclopropylcarbonyl)-2,2-dimethyl-3-oxazolidinecarboxylate in 10 ml of diethyl ether is treated at 0° within 5 minutes with 3.9 ml of a 1.36M solution of methylmagnesium iodide in 5 ml of diethyl ether. Subsequently, the reaction mixture is stirred at room temperature for 2.5 hours, then cooled to 0° and treated with 30 ml of semi-saturated ammonium chloride solution. The aqueous phase is extracted twice with 20 ml of diethyl ether, the combined organic extracts are thereafter dried over sodium sulphate and evaporated. For purification, the residue is chromatographed on 30 g of silica gel using a 3:1 mixture of petroleum ether and ether as the eluent. There are obtained 338 mg of tert-butyl (4S,5R)-4-(cyclohexylmethyl)-5-[(R/S)-1-cyclopropyl-1-hydroxyethyl-2,2-dimethyl-3-oxazolidinecarboxylate as a crystalline solid; MS: 366 (M–CH₃)⁺.

(e) (2R/S,3S,4S)-4-amino-5-cyclohexyl-2-cyclopropyl-2,3-pentanediol:

In a manner analogous to the procedure described above for the preparation of (2RS,3R,4S)-4-amino-5-cyclohexyl-1,2,3-pentanetriol, by reacting tert-butyl (4S,5R)-4-(cyclohexylmethyl)-5-[(R/S)-1-cyclopropyl-1-hydroxyethyl-2,2-dimethyl-3-oxazolidinecarboxylate there is obtained (2R/S,3S,4S)-4-amino-5-cyclohexyl-2-cyclopropyl-2,3-pentanediol as an amorphous solid which is used in the next step without further purification.

EXAMPLE 25

In an analogous manner to that described in Example 23, by condensing N-[(S)-α-[(tert-butylsulphonyl)methyl]hydrocinnamoyl]-1-(2,4-dinitrophenyl)-L-histidine and (2R,3S)-3-amino-4-cyclohexyl-1-cyclopropyl-2-hydroxy-1-butanone there is obtained (S)-α-[(S)-α-(tert-butylsulphonyl)methyl]hydrocinnamamido]-N-[(1S,2R)-1-(cyclohexylmethyl)-3-cyclopropyl-2-hydroxy-3-oxopropyl]-1-(2,4-dinitrophenyl)imidazole-4-propionamide as a yellow solid, MS: 795 (M+H)⁺.

The N-[(S)-α-[(tert-butylsulphonyl)methyl]hydrocinnamoyl]-1-(2,4-dinitrophenyl)-L-histidine used as the starting material was prepared as follows:

23.3 g (54.6 mmol) of methyl (S)-α-[(S)-α-[(tert-butylsulphonyl)methyl]hydrocinnamamido]imidazolepropionate in 250 ml of methylene chloride are treated with 7.43 ml (54.6 mmol) of triethylamine. Subsequently, 9.94 g (54.6 mmol) of 2,4-dinitro-1-fluorobenzene in 100 ml of methylene chloride are added dropwise within about 20 minutes while cooling with ice and the reaction mixture is stirred at room temperature until the reaction has finished, this being the case after 4 hours (checked by thin-layer chromatography). Usual working-up of the reaction mixture yields 20.5 g (62%) of N-[(S)-α-[(tert-butylsulphonyl)methyl]hydrocinnamoyl]-1-(2,4-dinitrophenyl)-L-histidine methyl ester as a brown foam, Rf value 0.4 in a 30:1 mixture of methylene chloride and methanol, MS: 602 (M+H)⁺.

20.5 g (34.07 mmol) of N-[(S)-α-[(tert-butylsulphonyl)methyl]hydrocinnamoyl]-1-(2,4-dinitrophenyl)-L-histidine methyl ester are dissolved in 180 ml of dioxan, treated with 85 ml (170.34 mmol) of 2N hydrochloric acid and subsequently heated to 80° for 2.5 hours. Usual working-up and crystallization from ether/hexane yields 15.7 g (78%) of N-[(S)-α-[(tert-butylsulphonyl)methyl]hydrocinnamoyl]-1-

(2,4-dinitrophenyl)-L-histidine in the form of a pale yellow amorphous solid, Rf value 0.2 in a 5:1 mixture of methylene chloride and methanol, MS: 588 (M+H)⁺.

The (2R,3S)-3-amino-4-cyclohexyl-1-cyclopropyl-2-hydroxy-1-butanone used as the starting material was prepared as follows:
(2R,3S)-3-Amino-4-cyclohexyl-1-cyclopropyl-2-hydroxy-1-butanone:

In a manner analogous to the procedure described in Example 24 for the preparation of (2RS,3R,4S)-4-amino-5-cyclohexyl-1,2,3-pentanetriol, starting from tert-butyl (4S,5R)-4-(cyclohexylmethyl)-5-(cyclopropylcarbonyl)-2,2-dimethyl-3-oxazolidinecarboxylate there is obtained (2R,3S)-3-amino-4-cyclohexyl-1-cyclopropyl-2-hydroxy-1-butanone, MS: 226 (M+H)⁺.

EXAMPLE 26

A mixture of 62.8 mg (0.1 mmol) of (S)-α-[(S)-α-[(tert-butylsulphonyl)methyl]hydrocinnamamido]-N-[(1S,2R)-1-(cyclohexylmethyl)-3-cyclopropyl-2-hydroxy-3-oxopropyl] imidazole-4-propionamide, 12 mg (0.2 mmol) of hydroxylamine hydrochloride and 0.027 ml (0.2 mmol) of triethylamine in 2.5 ml of methanol is heated to reflux for 20 hours. After the usual working-up the crude product obtained is purified by chromatography on 10 g of silica gel using a 8:1 mixture of methylene chloride and methanol as the eluting agent. There are obtained 28 mg of (S)-α-[(S)-α-[(tert-butylsulphonyl)methyl]hydrocinnamamido]-N-[(1S,2R,E/Z=2:1)-1-(cyclohexylmethyl)-3-cyclopropyl-2-hydroxy-3-(hydroxyimino)propyl]imidazole-4-propionamide as an amorphous solid; MS: 644 (M+H)⁺.

EXAMPLE 27

A solution of 85 mg (0.12 mmol) of tert-butyl (R)-2-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl]carbamoyl]-1-pyrrolidinecarboxylate in 1 ml of methanol and 1 ml of 2N hydrochloric acid is stirred at 50° for 2 hours. Subsequently, the reaction mixture is evaporated under reduced pressure and water is removed azeotropically twice with toluene. For purification, the residue is chromatographed on 20 g of silica gel using a 65:10:1 mixture of methylene chloride, methanol and ammonia as the eluting agent. The resulting 50 mg of crude product are thereafter re-precipitated in a methylene chloride-methanol-ether mixture. There are obtained 35 mg of (S)-N-[(1S,2R,3S)-1-(cyclohexylmethyl)-3-cyclopropyl-2,3-dihydroxypropyl]-α-[(S)-α-(D-propylamino)hydrocinnamamido]imidazole-4-propionamide as a colourless powder; MS: 609 (M+H)⁺.

EXAMPLE 28

The following compounds were obtained in an analogous manner to that described in Example 27:

From di-tert-butyl N-[(S)-1-(tert-butoxycarbonyl)-2-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl]carbamoyl]ethyl]ethylene dicarbamate the N2-(2-aminoethyl)-N4-[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl]-L-asparagine as an amorphous solid, MS: 670 (M+H)⁺;

from di-tert-butyl N-[[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl]carbamoyl]methyl]ethylene dicarbamate the (S)-α-[(S)-α-[2-[(2-aminoethyl)amino]acetamido]hydrocinnamamido]-N-[(1S,2R,3S)-1-(cyclohexylmethyl)-3-cyclopropyl-2,3-dihydroxypropyl]imidazole-4-propionamide as an amorphous solid, MS: 612 (M+H)⁺.

EXAMPLE 29

A mixture of 610 mg (0.8 mmol) of crude (S)-α-[(S)-α-[(tert-butylsulphonyl)methyl]hydrocinnamamido]-N-[(1S,2R,3S)-1-(cyclohexylmethyl)-3-cyclopropyl-3-fluoro-2-hydroxypropyl]-1-Boc-imidazole-4-propionamide and 110 mg (0.8 mmol) of potassium carbonate in 10 ml of methanol is stirred at room temperature under argon for 1 hour. Subsequently, 100 mg (1.9 mmol) of ammonium chloride are added. The mixture is stirred at room temperature for a further 15 minutes and thereafter evaporated under reduced pressure. The residue is dissolved in 20 ml of ethyl acetate and washed in succession with 10 ml of water and 10 ml of saturated sodium chloride solution. The aqueous phases are back-extracted twice with 20 ml of ethyl acetate. The pooled organic phases are dried over sodium sulphate and evaporated under reduced pressure. For purification, the residue (300 mg of a foam) is purified on 50 g of silica gel using a 9:1:0.1 mixture of methylene chloride, isopropanol and ammonia as the eluent. After lyophilization from dioxan there are obtained 95 mg of (S)-α-[(S)-α-[(tert-butylsulphonyl)methyl]hydrocinnamamido]-N-[(1S,2R,3S)-1-(cyclohexylmethyl)-3-cyclopropyl-3-fluoro-2-hydroxypropyl]imidazole-4-propionamide as a colourless powder; MS: 633 (M+H)⁺.

EXAMPLE 30

The following compounds were manufactured in an analogous manner to that described in Example 29:

From (S)-α-[(S)-α-[(tert-butylsulphonyl)methyl]hydrocinnamamido]-N-[(1S,2R,3R)-1-(cyclohexylmethyl)-3-cyclopropyl-3-fluoro-2-hydroxypropyl]-1-Boc-imidazole-4-propionamide the (S)-α-[(S)-α-[(tert-butylsulphonyl)methyl]hydrocinnamamido]-N-[(1S,2R,3R)-1-(cyclohexylmethyl)-3-cyclopropyl-3-fluoro-2-hydroxypropyl]imidazole-4-propionamide as a colourless, amorphous solid, MS: 633 (M+H)⁺;

from (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]-1-Boc-imidazole-4-propionamide the (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]-imidazole-4-propionamide, MS: 631 (M+H)⁺, as an amorphous solid;

from (S)-N-[(1S,2R,3S)-3-azido-1-(cyclohexylmethyl)-3-cyclopropyl-2-hydroxypropyl]-α-[(S)-α-(tert-butylsulphonyl)methyl]hydrocinnamamido]-1-Boc-imidazole-4-propionamide the (S)-N-[(1S,2R,3S)-3-azido-1-(cyclohexylmethyl)-3-cyclopropyl-2-hydroxypropyl]-α-[(S)-α-(tert-butylsulphonyl)methyl]hydrocinnamamido]imidazole-4-propionamide, MS: 656 (M+H)⁺;

from (S)-α-[(S)-α-[(tert-butylsulphonyl)methyl]hydrocinnamamido]-N-[(1S,2R,3R/S)-1-(cyclohexylmethyl)-3-cyclopropyl-2,3-dihydroxybutyl]-1-Boc-imidazole-4-propionamide the (S)-α-[(S)-α-[(tert-butylsulphonyl)methyl] hydrocinnamamido]-N-[(1S,2R,3R/S)-1-(cyclohexylmethyl)-3-cyclopropyl-2,3-dihydroxybutyl]imidazole-4-propionamide, MS 645 (M+H)⁺, as an amorphous solid.

EXAMPLE 31

A mixture of 375 mg (0.39 mmol) of (S)-α-2-benzimidazolecarboxamido-N-[(1S,2R,3S)-1-(cyclohexylmethyl)-3-cyclopropyl-2,3-dihydroxypropyl]-1-tritylimidazole-4-propionamide and 1.8 g (15.6 mmol) of pyridinium hydrochloride in 40 ml of methanol is heated to reflux for 3.5 hours. Thereafter, the reaction mixture is evaporated and the residue is partitioned between 100 ml of ethyl acetate and 50 ml of water. The organic phase is washed with 100 ml of semi-saturated ammonium chloride solution and 100 ml of 2N potassium bicarbonate solution, thereafter dried over sodium sulphate and evaporated under reduced pressure. For purification, the residue is chromatographed on 40 g of silica gel using a 6:1 mixture of methylene chloride and methanol as the eluent. There are obtained 110 mg of N-[(S)-1-[[(1S,2R,3S)-1-(cyclohexylmethyl)-3-cyclopropyl-2,3-dihydroxypropyl]carbamoyl]-2-imidazol-4-ylethyl]-2-benzimidazolecarboxamide as an amorphous solid; MS: 509 (M+H)⁺.

EXAMPLE 32

The following compounds were manufactured in an analogous manner to that described in Example 31:

From N-[(S)-1-[[(1S,2R,3S)-1-(cyclohexylmethyl)-3-cyclopropyl-2,3-dihydroxypropyl]carbamoyl]-2-(1-tritylimidazol)-4-ylethyl]indole-2-carboxamide the N-[(S)-1-[[(1S,2R,3S)-1-(cyclohexylmethyl)-3-cyclopropyl-2,3-dihydroxypropyl]carbamoyl]-2-imidazol-4-ylethyl]indole-2-carboxamide as an amorphous solid, MS: 508 (M+H)⁺;

from N-[(S)-1-[[(1S,2R,3S)-1-(cyclohexylmethyl)-3-cyclopropyl-2,3-dihydroxypropyl]carbamoyl]-2-(1-tritylimidazol)-4-ylethyl]-5-hydroxyindole-2-carboxamide the N-[(S)-1-[[(1S,2R,3S)-1-(cyclohexylmethyl)-3-cyclopropyl-2,3-dihydroxypropyl]carbamoyl]-2-imidazol-4-ylethyl]-5-hydroxy-indole-2-carboxamide as an amorphous solid, MS: 524 (M+H)⁺;

from (S)-α-benzothiazolecarboxamido-N-[(1S,2R,3S)-1-(cyclohexylmethyl)-3-cyclopropyl-2,3-dihydroxypropyl]-1-tritylimidazole-4-propionamide the (S)-α-benzothiazolecarboxamido-N-[(1S,2R,3S)-1-(cyclohexylmethyl)-3-cyclopropyl-2,3-dihydroxypropyl]imidazole-4-propionamide as an amorphous solid, MS: 526 (M+H)⁺;

from (S)-N-[(1S,2R,3S)-1-(cyclohexylmethyl)-3-cyclopropyl-2,3-dihydroxypropyl]-α-pyrrole-2-carboxamido-1-tritylimidazole-4-propionamide the (S)-N-[(1S,2R,3S)-1-(cyclohexylmethyl)-3-cyclopropyl-2,3-dihydroxypropyl]-α-pyrrole-2-carboxamidoimidazole-4-propionamide as an amorphous solid, MS: 458 (M+H)⁺;

from (S)-N-[(1S,2R,3S)-1-(cyclohexylmethyl)-3-cyclopropyl-2,3-dihydroxypropyl]-α-(2,2-dibenzylacetamido)-1-tritylimidazole-4-propionamide the (S)-N-[(1S,2R,3S)-1-(cyclohexylmethyl)-3-cyclopropyl-2,3-dihydroxypropyl]-α-(2,2-dibenzylacetamido)imidazole-4-propionamide as an amorphous solid, MS: 587 (M+H)⁺;

from ethyl (RS)-3-[(S)-1-[[(1S,2R,3S)-1-(cyclohexylmethyl)-3-cyclopropyl-2,3-dihydroxypropyl]carbamoyl]-2-(1-tritylimidazol)-4-ylethyl]-3,4-dihydro-2(1H)-isoquinolinecarboxylate (1:1 epimer mixture) the ethyl (RS)-3-[(S)-1-[[(1S,2R,3S)-1-(cyclohexylmethyl)-3-cyclopropyl-2,3-dihydroxypropyl]carbamoyl]-2-imidazol-4-ylethyl]-3,4-dihydro-2(1H)-isoquinolinecarboxylate (1:1 epimer mixture) as an amorphous solid, MS: 596 (M+H)⁺.

EXAMPLE 33

In an analogous manner to that described in Example 29, starting from (S)-α-[(S)-α-[(tert-butylsulphonyl)methyl] hydrocinnamamido]-N-[(1S,2R)-1-(cyclohexylmethyl)-3-cyclopropyl-2-hydroxy-3-oxopropyl]-1-(2,4-dinitrophenyl) imidazole-4-propionamide by treatment with potassium carbonate in methanol there is obtained (S)-α-[(S)-α-[(tert-butylsulphonyl)methyl]hydrocinnamamido]-N-[(1S,2R)-1-(cyclohexylmethyl)-3-cyclopropyl-2-hydroxy-3-oxopropyl] imidazole-4-propionamide as an amorphous solid; MS: 629 (M+H)⁺.

EXAMPLE 34

A suspension of 450 mg (0.57 mmol) of benzyl [[(2S or R,3R,4S)-4-[(S)-α-[(S)-α-[(tert-butylsulphonyl)methyl] hydrocinnamamido]imidazole-4-propionamido]-5-cyclohexyl-2,3-dihydroxypentyl]cyclopropylcarbamate and 90 mg of palladium/carbon (10%) in 20 ml of glacial acetic acid is hydrogenated at room temperature for 5.5 hours. Subsequently, the catalyst is filtered off, the filtrate is evaporated and the residue obtained (440 mg) is purified by chromatography using a 140:10:1 mixture of methylene chloride, methanol and ammonia as the eluent. There are obtained 103 mg of (S)-α-[(S)-α-[(tert-butylsulphonyl) methyl]hydrocinnamamido]-N-[(1S,2R)-1-(cyclohexylmethyl)-2-[(S or R)-3-cyclopropyl-2-oxo-5-oxazolidinyl]-2-hydroxyethyl]imidazole-4-propionamide as an amorphous solid; MS: 660 (M+H)⁺.

The benzyl [[(2S or R,3R,4S)-4-[(S)-α-[(S)-α-[(tert-butylsulphonyl)methyl]hydrocinnamamido]imidazole-4-propionamido]-5-cyclohexyl-2,3-dihydroxypentyl] cyclopropylcarbamate used as the starting material was prepared as follows:

(a) tert-Butyl (4S,5R)-4-(cyclohexylmethyl)-5-[(S)-2-(cyclopropylamino)-1-hydroxyethyl]-2,2-dimethyl-3-oxazolidinecarboxylate (and tert-butyl (4S,5R)-4-(cyclohexylmethyl)-5-[(R)-2-(cyclopropylamino)-1-hydroxyethyl]-2,2-dimethyl-3-oxazolidinecarboxylate):

A mixture of 733 mg (2.16 mmol) of tert-butyl (4S,5R)-4-(cyclohexylmethyl)-2,2-dimethyl-5-[(RS)-2-oxiranyl]-3-oxazolidinecarboxylate (WO 88/4664) and 2 ml of cyclopropylamine in 15 ml of methanol is stirred at 50° overnight under argon. Thereafter, the reaction mixture is evaporated and, for purification and separation of the epimers, the residue is chromatographed on 100 g of silica gel using a 98:2 mixture of chloroform and methanol as the eluent. There are obtained 185 mg of the less polar tert-butyl (4S,5R)-4-(cyclohexylmethyl)-5-[(S)-2-(cyclopropylamino)-1-hydroxyethyl]-2,2-dimethyl-3-oxazolidinecarboxylate, MS: 397 (M+H)⁺, and 341 mg of the more polar tert-butyl (4S,5R)-4-(cyclohexylmethyl)-5-[(R)-2-(cyclopropylamino)-1-hydroxyethyl]-2,2-dimethyl-3-oxazolidinecarboxylate, MS: 397 (M+H)⁺, each as a colourless oil.

(b) tert-Butyl (4S,5R)-5-[(S)-2-[1-(benzyloxy)-N-cyclopropylformamido]-1-hydroxyethyl]-4-

(cyclohexylmethyl)-2,2-dimethyl-3-oxazolidinecarboxylate:

A mixture of 180 mg (0.45 mmol) of tert-butyl (4S,5R)-4-(cyclohexylmethyl)-5-[(S)-2-(cyclopropylamino)-1-hydroxyethyl]-2,2-dimethyl-3-oxazolidinecarboxylate, 0.126 ml (0.98 mmol) of triethylamine and 136 mg (0.545 mmol) of N-(benzyloxycarbonyloxy)succinimide in 5 ml of methylene chloride is stirred at room temperature for 2 hours. Subsequently, the residue is poured on to ice and 2N sodium bicarbonate solution and then extracted three times with 150 ml of ether each time. The organic phase is washed with 70 ml of water, then dried over magnesium sulphate and evaporated. There are obtained 296 mg of tert-butyl (4S,5R)-5-[(S)-2-[1-(benzyloxy)-N-cyclopropylformamido]-1-hydroxyethyl]-4-(cyclohexylmethyl)-2,2-dimethyl-3-oxazolidinecarboxylate as a colourless oil; MS: 531 (M+H)$^+$.

(c) Benzyl [(2S or R,3R,4S)-4-amino-5-cyclohexyl-2,3-dihydroxypentyl]cyclopropylcarbamate:

In an analogous manner to that described in Example 24, from tert-butyl (4S,5R)-5-[(S)-2-[1-(benzyloxy)-N-cyclopropylformamido]-1-hydroxyethyl]-4-(cyclohexylmethyl)-2,2-dimethyl-3-oxazolidinecarboxylate there was obtained, after cleaving off the Boc and isopropylidene protecting groups using hydrochloric acid in methanol, the benzyl [(2S or R,3R,4S)-4-amino-5-cyclohexyl-2,3-dihydroxypentyl]cyclopropylcarbamate as an amorphous solid.

(d) Benzyl [[(2S or R,3R,4S)-4-[(S)-α-[(S)-α-[(tert-butylsulphonyl)methyl]hydrocinnamamido]imidazole-4-propionamido]-5-cyclohexyl-2,3-dihydroxypentyl]cyclopropylcarbamate:

In an analogous manner to that described in Example 23, by condensing (S)-1-(tert-butoxycarbonyl)-α-[(S)-α-[(tert-butylsulphonyl)methyl]hydrocinnamamido]imidazole-4-propionic acid and benzyl [(2S or R,3R,4S)-4-amino-5-cyclohexyl-2,3-dihydroxypentyl]cyclopropylcarbamate and subsequently cleaving off the Boc protecting group using potassium carbonate in methanol, analogously to Example 29, there was prepared benzyl [[(2S or R,3R,4S)-4-[(S)-α-[(S)-α-[(tert-butylsulphonyl)methyl]hydrocinnamamido]imidazole-4-propionamido]-5-cyclohexyl-2,3-dihydroxypentyl]cyclopropylcarbamate.

EXAMPLE 35

In an analogous manner to that described in Example 34, by catalytically hydrogenating benzyl [[(2R or S,3R,4S)-4-[(S)-α-[(S)-α-[(tert-butylsulphonyl)methyl]hydrocinnamamido]imidazole-4-propionamido]-5-cyclohexyl-2,3-dihydroxypentyl]cyclopropylcarbamate there was obtained (S)-α-[(S)-α-[(tert-butylsulphonyl)methyl]hydrocinnamamido]-N-[(1S,2R)-1-(cyclohexylmethyl)-2-[(R or S)-3-cyclopropyl-2-oxo-5-oxazolidinyl]-2-hydroxyethyl]-imidazole-4-propionamide as an amorphous solid; MS: 660 (M+H)$^+$.

The benzyl [[(2R or S,3R,4S)-4-[(S)-α-[(S)-α-[(tert-butylsulphonyl)methyl]hydrocinnamamido]imidazole-4-propionamido]-5-cyclohexyl-2,3-dihydroxypentyl]cyclopropylcarbamate used as the starting material was prepared as follows:

Starting from tert-butyl (4S,5R)-4-(cyclohexylmethyl)-5-[(R)-2-(cyclopropylamino)-1-hydroxyethyl]-2,2-dimethyl-3-oxazolidinecarboxylate there was obtained in a manner analogous to Example 34(b)—(d) by introduction of the benzyloxycarbonyl protecting group using N-benzyloxycarbonyloxy)succinimide followed by cleavage of the Boc and isopropylidene protecting groups using hydrochloric acid in methanol the benzyl [[(2R or S,3R,4S)-4-[(S)-α-[(S)-α-[(tert-butylsulphonyl)methyl]hydrocinnamamido]imidazole-4-propionamido]-5-cyclohexyl-2,3-dihydroxypentyl]cyclopropylcarbamate.

EXAMPLE 36

A suspension of 60 mg (0.09 mmol) of (S)-N-[(1S,2R,3S)-3-azido-1-(cyclohexylmethyl)-3-cyclopropyl-2-hydroxypropyl]-α-[(S)-α-[(tert-butylsulphonyl)methyl]hydrocinnamamido]imidazole-4-propionamide and 20 mg of palladium/carbon (5%) in 15 ml of methanol is hydrogenated at room temperature for 4 hours. After filtering off the catalyst the solvent is evaporated under reduced pressure. For purification, the crude product (40 mg) is chromatographed on 10 g of silica gel using a 80:10:1 mixture of methylene chloride, methanol and ammonia as the eluent. There are obtained 35 mg of (S)-N-[(1S,2R,3S)-3-amino-1-(cyclohexylmethyl)-3-cyclopropyl-2-hydroxypropyl]-α-[(S)-α-[(tert-butylsulphonyl)methyl]hydrocinnamamido]imidazole-4-propionamide as a colourless solid; MS: 630 (M+H)$^+$.

EXAMPLE 37

A solution of 90 mg (0.3 mmol) of (S)-α-[(S)-α-[(tert-butylsulphonyl)methyl]hydrocinnamamido]-N-[(S)-1-[(4R,5S)-5-cyclopropyl-2,2-dimethyl-1,3-dioxolan-4-yl]-2-(4-oxocyclohexyl)ethyl]imidazole-4-propionamide in 1 ml of methanol and 1 ml of 2N hydrochloric acid is stirred at room temperature for 3 hours. Subsequently, the reaction solution is evaporated and, for purification, the residue is chromatographed on 20 g of silica gel using a 14:1:0.1 mixture of methylene chloride, methanol and ammonia as the eluent. There are obtained 13 mg of (S)-α-[(S)-α-[(tert-butylsulphonyl)methyl]hydrocinnamamido]-N-[(1S,2R,3S)-3-cyclopropyl-2,3-dihydroxy-1-[(4-oxocyclohexyl)methyl]propyl]imidazole-4-propionamide as a colourless solid; MS: 684 (M+H)$^+$.

The (S)-α-[(S)-α-[(tert-butylsulphonyl)methyl]hydrocinnamamido]-N-[(S)-1-[(4R,5S)-5-cyclopropyl-2,2-dimethyl-1,3-dioxolan-4-yl]-2-(4-oxocyclohexyl)ethyl]-imidazole-4-propionamide used as the starting material was prepared as follows:

(a) Boc-[(RS)-4-Hydroxycyclohexyl]alanine methyl ester:

A suspension of 65.8 g (0.22 mol) of Boc-tyrosine methyl ester and 6.6 g of rhodium/aluminium oxide catalyst (5%) in 175 ml of methanol is hydrogenated at 50° and 4 bar hydrogen pressure for 3 hours. Subsequently, the catalyst is filtered off, the filtrate is evaporated under reduced pressure and, for purification, the residue obtained is chromatographed on 1 kg of silica gel using a 4:1 mixture of toluene and ethyl acetate as the eluent. There are obtained 41.97 g of Boc-[(RS)-4-hydroxycyclohexyl]alanine methyl ester, MS: 302 (M+H)$^+$, and 6.1 g of Boc-(4-oxocyclohexyl)alanine methyl ester, MS: 300 (M+H)$^+$, each as a colourless oil.

(b) (1S,2R,3S)-Amino-1-cyclopropyl-4-[(RS)-4-hydroxycyclohexyl]-1,2-butanediol:

This compound was obtained as an amorphous powder, MS: 244 (M+H)$^+$, analogously to the procedure which is described in WO 87/05302 for the synthesis of tert-butyl (4S,5R)-4-(cyclohexylmethyl)-5-formyl-2,2-dimethyl-3-oxazolidinecarboxylate from Boc-cyclohexylalanine methyl ester by replacing the Boc-cyclohexylalanine methyl ester by Boc-[(RS)-4-hydroxycyclohexyl]alanine methyl ester followed by the Grignard reaction with cyclopropylmagnesium bromide and cleaving off the Boc and isopropylidene protecting groups analogously to Example 16(a) and (b).

(c) (S)-α-[(S)-α-[(tert-Butylsulphonyl)methyl] hydrocinnamamido]-N-[(1S,2R,3S)-1-[[(RS)-4-hydroxycyclohexyl]methyl]-3-cyclopropyl-2,3-dihydroxypropyl]imidazole-4-propionamide:

In a manner analogous to the procedure described in Examples 23 and 29, by condensing (S)-1-(tert-butoxycarbonyl)-α-[(S)-α-[(tert-butylsulphonyl)methyl] hydrocinnamamido]imidazole-4-propionic acid with (1S, 2R)-3-amino-1-cyclopropyl-4-[(RS)-4-hydroxycyclohexyl]-1,2-butanediol and subsequently cleaving off the Boc protecting group there is obtained (S)-α-[(S)-α-[(tert-butylsulphonyl)methyl]hydrocinnamamido]-N-[(1S,2R,3S)-1-[[(RS)-4-hydroxycyclohexyl]methyl]-3-cyclopropyl-2,3-dihydroxypropyl]-imidazole-4-propionamide as a colourless solid: MS: 647 (M+H)$^+$.

(d) (S)-α-[(S)-α-[(tert-Butylsulphonyl)methyl] hydrocinnamamido]-N-[(S)-1-[(4R,5S)-5-cyclopropyl-2,2-dimethyl-1,3-dioxolan-4-yl]-2-[(RS)-4-hydroxycyclohexyl] ethyl]imidazole-4-propionamide:

A mixture of 300 mg (0.46 mmol) of (S)-α-[(S)-α-[(tert-butylsulphonyl)methyl]hydrocinnamamido]-N-[(1S,2R,3S)-1-[[(RS)-4-hydroxycyclohexyl]methyl]-3-cyclopropyl-2,3-dihydroxypropyl]imidazole-4-propionamide, 300 mg (1.5 mmol) of p-toluenesulphonic acid and 15 ml (122 mmol) of 2,2-dimethoxypropane in 5 ml of acetone is stirred at room temperature for 2 hours. Subsequently, the reaction mixture is poured on to ice and 70 ml of 2N sodium bicarbonate solution and extracted twice with 150 ml of ethyl acetate each time. The combined organic extracts are washed with 70 ml of water, thereafter dried over sodium sulphate and evaporated under reduced pressure. The residue is chromatographed on 30 g of silica gel using a 14:1:0.1 mixture of methylene chloride, methanol and ammonia as the eluent. There are obtained 270 mg of (S)-α-[(S)-α-[(tert-butylsulphonyl)methyl]hydrocinnamamido]-N-[(S)-1-[(4R, 5S)-5-cyclopropyl-2,2-dimethyl-1,3-dioxolan-4-yl]-2-[(RS) -4-hydroxycyclohexyl]ethyl]imidazole-4-propionamide as a colourless foam: MS: 687 (M+H)$^+$.

(e) (S)-α-[(S)-α-[(tert-Butylsulphonyl)methyl] hydrocinnamamido]-N-[(S)-1-[(4R,5S)-5-cyclopropyl-2,2-dimethyl-1,3-dioxolan-4-yl]-2-(4-oxocyclohexyl)ethyl] imidazole-4-propionamide:

A mixture of 260 mg (0.38 mmol) of (S)-α-[(S)-α-[(tert-butylsulphonyl)methyl]hydrocinnamamido]-N-[(S)-1-[(4R, 5S)-5-cyclopropyl-2,2-dimethyl-1,3-dioxolan-4-yl]-2-[(RS) -4-hydroxycyclohexyl]ethyl]imidazole-4-propionamide and 300 mg (1.9 mmol) of pyridine-sulphur trioxide complex in 5 ml of dimethyl sulphoxide is stirred at room temperature for 1.5 hours. The reaction mixture is thereafter poured into saturated ammonium chloride solution and extracted three times with 150 ml of ethyl acetate each time. The combined organic extracts are washed with 70 ml of saturated ammonium chloride solution and 70 ml of water, dried over sodium sulphate and evaporated. The residue (190 mg) is chromatographed on 20 g of silica gel using a 14:1:0.1 mixture of methylene chloride, methanol and ammonia as the eluent. There are obtained 90 mg of (S)-α-[(S)-α-[(tert-butylsulphonyl)methyl]hydrocinnamamido]-N-[(S)-1-[(4R, 5S)-5-cyclopropyl-2,2-dimethyl-1,3-dioxolan-4-yl]-2-(4-oxocyclohexyl)ethyl]imidazole-4-propionamide as a colourless oil; MS: 685 (M+H)$^+$.

EXAMPLE 38

A solution of 335 mg (0.44 mmol) of (S)-α-[(S)-α-[(tert-butylsulphonyl)methyl]hydrocinnamamido]-N-[(1S,2R, 3S)-1-(cyclohexylmethyl)-3-cyclopropyl-2,3-dihydroxypropyl]-5-iodoimidazole-4-propionamide and 79 mg (0.88 mmol) of copper-(I) cyanide in 25 ml of dimethylformamide is stirred at 120° overnight under argon. Subsequently, the reaction mixture is evaporated under reduced pressure, the residue is suspended in 30 ml of a 95:5 mixture of methylene chloride and methanol and filtered over Dicalite. The filtrate is evaporated and, for purification, the residue is chromatographed on 50 g of silica gel using a 160:10:1 mixture of methylene chloride, methanol and ammonia as the eluent. After precipitation from a methylene chloride-ether mixture there are obtained 40 mg of (S)-α-[ (S)-α-[(tert-butylsulphonyl)methyl]hydrocinnamamido]-N-[(1S,2R,3S)-1-(cyclohexylmethyl)-3-cyclopropyl-2,3-dihydroxypropyl]-5-cyanoimidazole-4-propionamide as a colourless powder; MS: 656 (M+H)$^+$.

The (S)-α-[(S)-α-[(tert-butylsulphonyl)methyl] hydrocinnamamido]-N-[(1S,2R,3S)-1-(cyclohexylmethyl)-3-cyclopropyl-2,3-dihydroxypropyl]-5-iodoimidazole-4-propionamide used as the starting material was prepared as follows:

10.4 ml (2.08 mmol) of a 0.2N methanolic iodine solution and 2.4 ml (0.48 mmol) of 0.2N sodium hydroxide solution are simultaneously added dropwise at 0° while stirring to a mixture of 630 mg (1 mmol) of (S)-α-[(S)-α-[(tert-butylsulphonyl)methyl]hydrocinnamamido]-N-[(1S,2R,3S) -1-(cyclohexylmethyl)-3-cyclopropyl-2,3-dihydroxypropyl] imidazole-4-propionamide and 20 ml (4 mmol) of 0.2N sodium hydroxide solution in 20 ml of methanol. The colourless reaction mixture is stirred at 0° for 5 minutes and thereafter at room temperature for 2.5 hours. Subsequently, the mixture is diluted with 25 ml of water and extracted twice with 80 ml of ethyl acetate each time. The combined organic extracts are washed with saturated sodium chloride solution, dried over sodium sulphate and evaporated under reduced pressure. For purification, the residue (750 mg) is chromatographed using a 15:1 mixture of methylene chloride and methanol as the eluent. There are obtained 504 mg of (S)-α-[(S)-α-[(tert-butylsulphonyl)methyl] hydrocinnamamido]-N-[(1S,2R, 3S)-1-(cyclohexylmethyl)-3-cyclopropyl-2,3-dihydroxypropyl]-5-iodoimidazole-4-propionamide, MS: 757 (M+H)$^+$, and 38 mg of (S)-α-[(S)-α-[(tert-butylsulphonyl)methyl]hydrocinnamamido]-N-[ (1S,2R,3S)-1-(cyclohexylmethyl)-3-cyclopropyl-2,3-dihydroxypropyl]-2,5-diiodoimidazole-4-propionamide, MS: 883 (M+H)$^+$, each as a colourless solid.

EXAMPLE 39

1.5 ml (2.8 mmol) of phosgene in toluene (20%) are added at room temperature to a solution of 150 mg (0.2 mmol) of (S)-α-[(S)-α-[(tert-butylsulphonyl)methyl] hydrocinnamamido]-N-[(1S,2R,3S)-1-(cyclohexylmethyl)-3-cyclopropyl-2,3-dihydroxypropyl]imidazole-4-propionamide in 15 ml of methylene chloride and the reaction solution is stirred for 3 hours. Thereafter, it is evaporated and, for purification, the residue is chromatographed on 10 g of silica gel using a 96:4 mixture of methylene chloride and methanol as the eluent. After lyophilization from dioxan/water there are obtained 57 mg of (1R,2S)-1-[(S)-1-[(S)-α-[(S)-α-[(tert-butylsulphonyl) hydrocinnamamido]imidazole-4-propionamido]-2-cyclohexylethyl]-2-cyclopropylethylene cyclic carbonate hydrochloride as a colourless powder; MS: 657 (M+H)$^+$.

EXAMPLE 40

A mixture of 200 mg (0.3 mmol) of (S)-α-[(S)-α-[(tert-butylsulphonyl)methyl]hydrocinnamamido]-N-[(1S,2R, 3S)-1-(cyclohexylmethyl)-3-cyclopropyl-2,3-dihydroxypropyl]imidazole-4-propionamide and 543 mg (3 mmol) of sulphur trioxide-triethylamine complex in 3 ml of dimethylformamide is stirred at room temperature for 48 hours. Thereafter, 480 mg (5.8 mmol) of sodium acetate dissolved in the least possible water are added and the reaction mixture is evaporated in a high vacuum. The residue is triturated in 5 ml of acetonitrile, thereafter insolubles are filtered off and the filtrate is evaporated under reduced pressure. The residue obtained is purified by chromatography on 50 g of silica gel with a 25:5:3 mixture of ethyl acetate, methanol and water as the eluent. After lyophilization from dioxan/water there are obtained 159 mg of (1R,2S)-1-[(S)-1-[(S)-α-[(S)-α-[(tert-butylsulphonyl]hydrocinnamamido]imidazole-4-propionamido]-2-cyclohexylethyl]-2-cyclopropylethylene disulphate sodium salt (1:2) as a colourless powder; MS: 808 (M+NH$_4$)$^+$.

EXAMPLE 41

A suspension of 304 mg (1.6 mmol) of monomethyl (S)-2-acetoxysuccinate (Hua Hsüh Hsüh Pao 38, 502, 1980, CA 94, 174940), 330 mg (1.6 mmol) of dicyclohexylcarbodiimide, 14 mg (0.12 mmol) of 4-dimethylaminopyridine and 252 mg (0.4 mmol) of (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]imidazole-4-propionamide in 20 ml of methylene chloride is stirred at room temperature for 4 hours. Subsequently, the reaction mixture is evaporated, the residue is triturated with 50 ml of ether and thereafter insoluble dicyclohexylurea is filtered off. After evaporation of the ether solution the residue obtained (500 mg) is chromatographed on 50 g of silica gel using a 20:1 mixture of methylene chloride and methanol as the eluent. There are obtained 76 mg of (1R,2S)-1-[(S)-1-[(S)-α-[(S)-α-[(tert-butylsulphonyl)methyl]hydrocinnamamido]imidazole-4-propionamido]-2-cyclohexylethyl]-2-cyclopropylethylene bis[(S)-2-acetoxy-3-(methoxycarbonyl)propionate as an amorphous solid; MS: 976 (M+H)$^+$.

EXAMPLE 42

The following compounds were manufactured in an analogous manner to that described in Example 41:

From (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]imidazole-4-propionamide and 2-acetoxybenzoic acid the (1R,2S)-1-[(S)-1-[(S)-α-[(S)-α-[(tert-butylsulphonyl)methyl]hydrocinnamamido]imidazole-4-propionamido]-2-cyclohexylethyl]-2-cyclopropylethylene bis(o-acetoxybenzoate) as an amorphous solid, MS: 956 (M+H)$^+$;

from (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]imidazole-4-propionamide and 2-aminobenzoic acid the (1S,2R,3S)-3-[(S)-α-[(S)-α-[(tert-butylsulphonyl)methyl]hydrocinnamamido]imidazole-4-propionamido]-4-cyclohexyl-1-cyclopropyl-2-hydroxybutyl o-aminobenzoate as an amorphous solid, MS: 750 (M+H)$^+$.

EXAMPLE 43

A mixture of 315 mg (0.5 mmol) of (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]imidazole-4-propionamide, 0.345 ml (2.5 mmol) of triethylamine and 426 mg (2.5 mmol) of chloroacetic anhydride in 25 ml of methylene chloride is stirred at room temperature for 2 hours. Subsequently, the mixture is partitioned between 50 ml of methylene chloride and 50 ml of water, the organic phase is separated and dried over sodium sulphate. After evaporation the residue obtained (350 mg) is purified by chromatography on 25 g of silica gel using a 20:1 mixture of methylene chloride and methanol as the eluent. There are obtained 371 mg of (1R,2S)-1-[(S)-1-[(S)-α-[(S)-α-[(tert-butylsulphonyl)methyl]hydrocinnamamido]imidazole-4-propionamido]-2-cyclohexylethyl]-2-cyclopropylethylene bis(chloroacetate) as a foam; MS: 783 (M+H)$^+$.

A solution of 371 mg (0.47 mmol) of (1R,2S)-1-[(S)-1-[(S)-α-[(S)-α-[(tert-butylsulphonyl)methyl]hydrocinnamamido]imidazole-4-propionamido]-2-cyclohexylethyl]-1-cyclopropylethylene bis(chloroacetate) in 15 ml (172 mmol) of morpholine is stirred at 90° for 16 hours. Thereafter, the morpholine is evaporated under reduced pressure, the residue is taken up in 100 ml of ethyl acetate and washed with 100 ml of water. The organic phase is dried over sodium sulphate and thereafter evaporated. For purification, the residue obtained is chromatographed on 30 g of silica gel using a 10:1 mixture of methylene chloride and methanol as the eluent. There are obtained 101 mg of (1R,2S)-1-[(S)-1-[(S)-α-[(S)-α-[(tert-butylsulphonyl)methyl]hydrocinnamamido]imidazole-3-propionamido]-2-cyclohexylethyl]-2-cyclopropylethylene di-4-morpholinoacetate as an amorphous solid; MS: 763 [M+H-(CH$_3$)$_3$CSO$_2$H]$^+$.

EXAMPLE 44

A mixture of 100 mg (0.16 mmol) of (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]imidazole-4-propionamide, 126 mg (0.63 mmol) of 2-(3-pyridyl)benzoic acid [Z. Chem. 7, 22 (1967)], 195 mg (10.6 mmol) of 4-dimethylaminopyridine and 212 mg (0.56 mmol) of HBTU in 10 ml of methylene chloride is stirred at room temperature for 24 hours under argon. Subsequently, the reaction mixture is evaporated and the residue is taken up in 160 ml of ethyl acetate. The ethyl acetate solution is washed with 80 ml of 2N sodium carbonate solution and 80 ml of saturated ammonium chloride solution. The combined aqueous phases are again extracted twice with 160 ml of ethyl acetate each time. The combined ethyl acetate solutions are dried over magnesium sulphate and evaporated under reduced pressure. For purification, the crude product obtained (350 mg) is chromatographed on 50 g of silica gel using a 250:10:1 mixture of methylene chloride, methanol and ammonia as the eluent. There are obtained 140 mg of (1R,2S)-1-[(S)-1-[(S)-α-[(S)-α-[(tert-butylsulphonyl)methyl]hydrocinnamamido]imidazole-4-propionamido]-2-cyclohexylethyl]-2-cyclopropylethylene bis[o-(2-pyridyl)benzoate] as an amorphous solid; MS: 993 (M+H)$^+$.

EXAMPLE 45

The following compounds were manufactured in an analogous manner to that described in Example 44:

From (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]imidazole-4-propionamide and 3-(3-pyridyl)propionic acid (J. Chem. Soc. Japan 62, 183, 1941) the (1R,2S)-1-[(S)-1-[(S)-α-[(S)-α-[(tert-butylsulphonyl)methyl]hydrocinnamamido]imidazole-4-propionamido]-2-cyclohexylethyl]-2-cyclopropylethylene di-3-pyridinepropionate as an amorphous solid, MS: 897 (M+H)⁺;

from (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]imidazole-4-propionamide and cyclopropanecarboxylic acid the (1S,2R,3S)-3-[(S)-α-[(S)-α-[(tert-butylsulphonyl)methyl]hydrocinnamamido]imidazole-4-propionamido]-4-cyclohexyl- 1-cyclopropyl-2-hydroxybutylcyclopropanecarboxylate, MS: 699 (M+H)⁺, and the (1R,2S)-1-[(S)-1-[(S)-α-[(S)-α-[(tert-butylsulphonyl)methyl]hydrocinnamamido]imidazole-4-propionamido]-2-cyclohexylethyl]-2-cyclopropylethylene dicyclopropanecarboxylate MS: 767 (M+H)⁺, both as an amorphous solid;

from (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]imidazole-4-propionamide and 3-(4-imidazole)propionic acid the (1R,2S)-1-[(S)-1-[(S)-α-[(S)-α-[(tert-butylsulphonyl)methyl]hydrocinnamamido]imidazole-4-propionamido]-2-cyclohexylethyl]-2-cyclopropylethylene diimidazole-4-carboxylate, MS: 875 (M+H)⁺, and the (1S,2R,3S)-3-[(S)-α-[(S)-α-[(tert-butylsulphonyl)methyl]hydrocinnamamido]imidazol-4-propionamido]-4-cyclohexyl-1-cyclopropyl-2-hydroxybutylimidazole-4-propionate, MS: 753 (M+H)⁺, each as an amorphous solid.

EXAMPLE 46

A mixture of 150 mg (0.24 mmol) of (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]imidazole-4-propionamide, 340 mg (1.2 mmol) of 3-phenylpropionic anhydride and 40 mg (0.33 mmol) of 4-dimethylaminopyridine in 1.5 ml of pyridine is stirred at room temperature for 24 hours. Subsequently, the reaction mixture is evaporated under reduced pressure and, for purification, the residue is chromatographed on 35 g of silica gel using a 200:10:1 mixture of methylene chloride, methanol and ammonia as the eluent. There are obtained 240 mg of (1R,2S)-1-[(S)-1-[(S)-α-[(S)-α-[(tert-butylsulphonyl)methyl]hydrocinnamamido]imidazole-4-propionamido]-2-cyclohexylethyl]-2-cyclopropylethylene dihydrocinnamate as a colourless oil; MS: 895 (M+H)⁺.

EXAMPLE 47

A solution of 200 mg (0.32 mmol) of (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]imidazole-4-propionamide, 0.23 ml (1.6 mmol) of diethyl chlorophosphate and 50 mg of dimethylaminopyridine in 5 ml of pyridine is left to stand at room temperature for 2 days. The reaction mixture is subsequently evaporated to dryness under reduced pressure and the residue is taken up in ethyl acetate. The organic phase is washed twice with saturated sodium bicarbonate solution, dried over sodium sulphate and subsequently evaporated. For purification, the crude product (340 mg) is chromatographed on 50 g of silica gel using a 150:10:1 mixture of methylene chloride, methanol and ammonia as the eluent, whereby there are obtained, in addition to starting material, 35 mg of (1S,2R,3S)-3-[(S)-α-[(S)-α-[(tert-butylsulphonyl)methyl]hydrocinnamamido]imidazole-4-propionamido]-4-cyclohexyl-1-cyclopropyl-2-hydroxybutyl diethyl phosphate as a colourless foam; MS: 767 (M+H)⁺.

EXAMPLE 48

In an analogous manner to that described in Example 47, by reacting (S)-α-[(S)-α-[(tert-butylsulphonyl)methyl]hydrocinnamamido]-N-[(1S,2R,3S)-1-(cyclohexylmethyl)-3-cyclopropyl-2,3-dihydroxypropyl]imidazole-4-propionamide with acetic anhydride there is obtained (1R,2S)-1-[(S)-1-[(S)-1-acetyl-α-(S)-α-[(tert-butylsulphonyl)methyl]imidazole-4-propionamido]-2-cyclohexylethyl]-2-cyclopropylethylene diacetate as a colourless solid; MS: 757 (M+H)⁺.

EXAMPLE 49

The following compounds were manufactured in an analogous manner to that described in Example 16:

From (S)-α-amino-N-[(1S,2R,3S)-1-(cyclohexylmethyl)-3-cyclopropyl-2,3-dihydroxypropyl]-1-tritylimidazole-4-propionamide and 5-chloroindole-2-carboxylic acid the 5-chloro-N-[(S)-1-[[(1S,2R,3S)-1-(cyclohexylmethyl)-3-cyclopropyl-2,3-dihydroxypropyl]carbamoyl]-2-(1-tritylimidazol)-4-ylethyl]indole-2-carboxamide;

from (S)-α-amino-N-[(1S,2R,3S)-1-(cyclohexylmethyl)-3-cyclopropyl-2,3-dihydroxypropyl]-1-tritylimidazole-4-propionamide and 5-fluoroindol-2-carboxylic acid the N-[(S)-1-[[(1S,2R,3S)-1-(cyclohexylmethyl)-3-cyclopropyl-2,3-dihydroxypropyl]carbamoyl]-2-(1-tritylimidazol)-4-ylethyl]-5-fluoroindole-2-carboxamide;

from (S)-α-amino-N-[(1S,2R,3S)-1-(cyclohexylmethyl)-3-cyclopropyl-2,3-dihydroxypropyl]-1-tritylimidazole-4-propionamide and 5-methylindole-2-carboxylic acid the N-[(S)-1-[[(1S,2R,3S)-1-(cyclohexylmethyl)-3-cyclopropyl-2,3-dihydroxypropyl]carbamoyl]-2-(1-tritylimidazol)-4-ylethyl]-5-methylindole-2-carboxamide;

from (S)-α-amino-N-[(1S,2R,3S)-1-(cyclohexylmethyl)-3-cyclopropyl-2,3-dihydroxypropyl]-1-tritylimidazole-4-propionamide and 5-methoxyindole-2-carboxylic acid the N-[(S)-1-[[(1S,2R,3S)-1-(cyclohexylmethyl)-3-cyclopropyl-2,3-dihydroxypropyl]carbamoyl]-2-(1-tritylimidazol)-4-ylethyl]-5-methoxyindole-2-carboxamide;

from (S)-α-amino-N-[(1S,2R,3S)-1-(cyclohexylmethyl)-3-cyclopropyl-2,3-dihydroxypropyl]-1-tritylimidazole-4-propionamide and 3-chloroindole-2-carboxylic acid (J. Med. Chem. 1972, 659) the 3-chloro-N-[(S)-1-[[(1S,2R,3S)-1-(cyclohexylmethyl)-3-cyclopropyl-2,3-dihydroxypropyl]carbamoyl]-2-(1-tritylimidazol)-4-ylethyl]indole-2-carboxamide;

from (S)-α-amino-N-[(1S,2R,3S)-1-(cyclohexylmethyl)-3-cyclopropyl-2,3-dihydroxypropyl]-1-tritylimidazole-4-propionamide and 3,6-dichloroindole-2-carboxylic acid the 3,6-dichloro-N-[(S)-1-[[(1S,2R,3S)-1-(cyclohexylmethyl)-3-cyclopropyl-2,3-dihydroxypropyl]carbamoyl]-2-(1-tritylimidazol)-4-ylethyl]indole-2-carboxamide;

from (S)-α-amino-N-[(1S,2R,3S)-1-(cyclohexylmethyl)-3-cyclopropyl-2,3-dihydroxypropyl]-1-tritylimidazole-4-propionamide and quinoline-2-carboxylic acid the N-[(S)-1-[[(1S,2R,3S)-1-(cyclohexylmethyl)-3-cyclopropyl-2,3-dihydroxypropyl]carbamoyl]-2-(1-tritylimidazol)-4-ylethyl]-2-quinolinecarboxamide;

from (S)-α-amino-N-[(1S,2R,3S)-1-(cyclohexylmethyl)-3-cyclopropyl-2,3-dihydroxypropyl]-1-tritylimidazole-4-propionamide and 1,4-benzodioxane-2-carboxylic acid (Chim. Ther. 1984, 411) the (S)-α-[(RS)-1,4-benzodioxane-2-carboxamido]-N-[(1S,2R,3S)-1-(cyclohexylmethyl)-3-cyclopropyl-2,3-dihydroxypropyl]-1-tritylimidazole-4-propionamide;

from (S)-α-amino-N-[(1S,2R,3S)-1-(cyclohexylmethyl)-3-cyclopropyl-2,3-dihydroxypropyl]-1-tritylimidazole-4-propionamide and (RS)-Boc-(3-pyridyl)alanine (Pharmacology 1969, 271) the tert.butyl [(RS)-1-[[(S)-1-[[(1S,2R,3S)-1-(cyclohexylmethyl)-3-cyclopropyl-2,3-dihydroxypropyl]carbamoyl]-2-(1-tritylimidazol)-4-ylethyl]carbamoyl]-2-(3-pyridyl)ethyl]carbamate.

The 3,6-dichloroindole-2-carboxylic acid used as the starting material was prepared analogously to the process described in J. Med. Chem. 1972, 659 for the preparation of 3-chloroindole-2-carboxylic acid.

EXAMPLE 50

The following compounds were manufactured in an analogous manner to that described in Example 16:

From (R)-2-amino-N-[(1S,2R,3S)-1-(cyclohexylmethyl)-3-cyclopropyl-2,3-dihydroxypropyl]-3-(methylthio)propionamide and N-[3-[1-(tert-butoxy)formamido]-3-methylbutyryl]-3-(p-methoxyphenyl)-L-alanine the tert-butyl [2-[[(S)-α-[[(R)-1-[[(1S,2R,3S)-1-(cyclohexylmethyl)-3-cyclopropyl-2,3-dihydroxypropyl]-carbamoyl-2-(methylthio)ethyl]carbamoyl]-p-methoxyphenethyl]carbamoyl]-1,1-dimethyl]carbamate as an amorphous solid, MS: 621 (M+H–Boc)⁺;

from (S)-α-amino-N-[(1S,2R,3S)-1-(cyclohexylmethyl)-3-cyclopropyl-2,3-dihydroxypropyl]-4-thiazolepropionamide (prepared as described in Example 18) and N-[3-[1-(tert-butoxy)formamido]-3-methylbutyryl]-3-(p-methoxyphenyl)-L-alanine the tert-butyl [2-[[(S)-α-[[(S)-1-[[(1S,2R,3S)-1-(cyclohexylmethyl)-3-cyclopropyl-2,3-dihydroxypropyl]carbamoyl]-2-(5-thiazolyl)ethyl]carbamoyl]-p-methoxyphenethyl]carbamoyl]-1,1-dimethylethyl]carbamate as a colourless foam, MS: 758 (M+H)⁺;

from (S)-2-amino-N¹-[(1S,2R,3S)-1-(cyclohexylmethyl)-3-cyclopropyl-2,3-dihydroxypropyl]succinamide and (S)-α-[(tert-butylsulphonyl)methyl]hydrocinnamic acid the (S)-2-[(S)-α-[(tert-butylsulphonyl)methyl]hydrocinnamido]-N¹-[(1S,2R,3S)-1-(cyclohexylmethyl)-3-cyclopropyl-2,3-dihydroxypropyl]succinamide as a colourless foam, MS: 608 (M+H)⁺.

The (R)-2-amino-N-[(1S,2R,3S)-1-(cyclohexylmethyl)-3-cyclopropyl-2,3-dihydroxypropyl]-3-(methylthio)propionamide used as the starting material was prepared as follows:

In an analogous manner to that described in Example 18 a) and b), by condensing (R)-Boc-(S-methyl)cysteine (J. Chem. Soc. C 1967, 2632) and (1S,2R,3S)-3-amino-4-cyclohexyl-1-cyclopropyl-1,2-butanediol there was obtained tert-butyl [(R)-1-[[(1S,2R,3S)-1-(cyclohexylmethyl)-3-cyclopropyl-2,3-dihydroxypropyl]carbamoyl]-2-(methylthio)ethyl]carbamate as an amorphous solid, MS: 445 (M+H)⁺. Subsequent cleavage of the Boc protecting group using hydrochloric acid in methanol yielded (R)-2-amino-N-[(1S,2R,3S)-1-(cyclohexylmethyl)-3-cyclopropyl-2,3-dihydroxypropyl]-3-(methylthio)propionamide.

The N-[3-[1-(tert-butoxy)formamido]-3-methylbutyryl]-3-(p-methoxyphenyl)-L-alanine used as the starting material was prepared as follows:

In an analogous manner to that described in Example 20 for the preparation of N-[3-[1-(benzyloxy)formamido]-3-methylbutyryl]-3-(p-methoxyphenyl)-L-alanine, N-[3-[1-(tert-butoxy)formamido]-3-methylbutyryl]-3-(p-methoxyphenyl)-L-alanine methyl ester was obtained by using in the condensation, in place of N-[(benzyloxy)carbonyl]-2,3-dimethyl-β-alanine (EPA 0230266), N-[(tert-butoxy)carbonyl]-2,3-dimethyl-β-alanine which in turn was obtained in an analogous manner to that described in EPA 0230266 for N-[(benzyloxy)carbonyl]-2,3-dimethyl-β-alanine by replacing the benzyl alcohol by tert-butanol. Subsequent basic hydrolysis gave the N-[3-[1-(tert-butoxy)formamido]-3-methylbutyryl]-3-(p-methoxyphenyl)L-alanine as an amorphous solid.

The (S)-2-amino-N¹-[(1S,2R,3S)-1-(cyclohexylmethyl)-3-cyclopropyl-2,3-dihydroxypropyl]succinamide used as the starting material was prepared as follows:

In an analogous manner to that described in Example 18a), by condensing N-α-Fmoc-asparagine and (1S,2R,3S)-3-amino-4-cyclohexyl-1-cyclopropyl-1,2-butanediol and subsequently cleaving off the Fmoc protecting group using piperidine in methylene chloride there was obtained (S)-2-amino-N¹-[(1S,2R,3S)-1-(cyclohexylmethyl)-3-cyclopropyl-2,3-dihydroxypropyl]succinamide as a colourless solid, MS: 342 (M+H)⁺.

EXAMPLE 51

The following compounds were obtained in an analogous manner to that described in Example 19:

From (S)-α-amino-N-[(1S,2R,3S)-1-(cyclohexylmethyl)-3-cyclopropyl-2,3-dihydroxypropyl]imidazole-4-propionamide and N-(4-morpholinylcarbonyl)-L-phenylalanine (J. Med. Chem. 1988, 31, 2277) the (S)-N-[(1S,2R,3S)-1-(cyclohexylmethyl)-3-cyclopropyl-2,3-dihydroxypropyl]-α-[(S)-α-(4-morpholinecarboxamido)hydrocinnamamido] imidazole-4-propionamide as an amorphous solid, MS: 625 (M+H)⁺;

from (S)-α-amino-N-[(1S,2R,3S)-1-(cyclohexylmethyl)-3-cyclopropyl-2,3-dihydroxypropyl]imidazole-4-propionamide and N-[3-[1-(benzyloxy)formamido]-3-methylbutyryl]-3-(p-methoxyphenyl)-L-alanine the benzyl [2-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-p-methoxyphenethyl]carbamoyl]-1,1-dimethylethyl]carbamate as a colourless foam, MS: 775 (M+H)⁺;

from (S)-α-amino-N-[(1S,2R,3S)-1-(cyclohexylmethyl)-3-cyclopropyl-2,3-dihydroxypropyl]imidazole-4-propionamide and N-[3-[1-(benzyloxy)formamido]propionyl]-3-(p-methoxyphenyl)-L-alanine the benzyl [2-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-p-methoxyphenethyl]carbamoyl]ethyl]carbamate as a colourless solid, MS: 747 (M+H)⁺;

from (S)-α-amino-N-[(1S,2R,3S)-1-(cyclohexylmethyl)-3-cyclopropyl-2,3-dihydroxypropyl]imidazole-4- propionamide and N-[6-[-1-(benzyloxy)formamido]hexanoyl]-3-(p-methoxyphenyl)-L-alanine the benzyl [5-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-p-methoxyphenethyl]carbamoyl]pentyl]carbamate as a colourless solid, MS: 789 (M+H)$^+$;

from (S)-α-amino-N-[(1S,2R,3S)-1-(cyclohexylmethyl)-3-cyclopropyl-2,3-dihydroxypropyl]imidazole-4-propionamide and N-[[p-[1-(benzyloxy)formamido]phenyl]acetyl]-3-(p-methoxyphenyl)-L-alanine the p-[[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-p-methoxyphenethyl]carbamoyl]methyl]carbanilic acid benzyl ester as a colourless solid, MS: 809 (M+H)$^+$;

from (S)-α-amino-N-[(1S,2R,3S)-1-(cyclohexylmethyl)-3-cyclopropyl-2,3-dihydroxypropyl]imidazole-4-propionamide and N-[[cis/trans-4-[1-(benzyloxy)formamido]cyclohexyl]acetyl]-3-(p-methoxyphenyl)-L-alanine the benzyl cis/trans-4-[[[(S)-α-1-[[(1S,2R,3S)-1-(cyclohexylmethyl)-3-cyclopropyl-2,3-dihydroxypropyl]carbamoyl-2-imidazol-4-ylethyl]carbamoyl]-p-methoxyphenethyl]carbamoyl]methyl]cyclohexanecarbamate as an amorphous solid, MS: 815 (M+H)$^+$;

from (S)-α-amino-N-[(1S,2R,3S)-1-(cyclohexylmethyl)-3-cyclopropyl-2,3-dihydroxypropyl]imidazole-4-propionamide and N-[(S)-4-[1-(benzyloxy)formamido]-2-hydroxybutyryl]-3-(p-methoxyphenyl)-L-alanine the benzyl [(S)-3-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-p-methoxyphenethyl]carbamoyl]-2-hydroxyethyl]carbamate as a colourless foam, MS: 777 (M+H)$^+$;

from (S)-α-amino-N-[(1S,2R,3S)-1-(cyclohexylmethyl)-3-cyclopropyl-2,3-dihydroxypropyl]imidazole-4-propionamide and N-(3-hydroxy-3-methylbutyryl)-3-(p-methoxyphenyl)-L-alanine the (S)-N-[(1S,2R,3S)-1-(cyclohexylmethyl)-3-cyclopropyl-2,3-dihydroxypropyl]-α-[(S)-α-(3-hydroxy-3-methylbutyramido)-p-methoxyhydrocinnamamido]imidazole-4-propionamide as a colourless foam, MS: 642 (M+H)$^+$;

from (S)-α-amino-N-[(1S,2R,3S)-1-(cyclohexylmethyl)-3-cyclopropyl-2,3-dihydroxypropyl]imidazole-4-propionamide and 3-(p-methoxyphenyl)-N-[3-methyl-3-(4-morpholinecarboxamido)-3-methylbutyryl]-L-alanine the N-[1-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-p-methoxyphenethyl]-carbamoyl]-1-methylethyl]-4-morpholinecarboxamide as a colourless foam, MS: 754 (M+H)$^+$;

from (S)-α-amino-N-[(1S,2R,3S)-1-(cyclohexylmethyl)-3-cyclopropyl-2,3-dihydroxypropyl]imidazole-4-propionamide and N-[[1-[1-(benzyloxy)formamido]cyclopropyl]acetyl]-3-(p-methoxyphenyl)-L-alanine the benzyl [1-[[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-p-methoxyphenethyl]carbamoyl]methyl]cyclopropyl]carbamate as a colourless solid, MS: 773 (M+H)$^+$;

from (S)-α-amino-N-[(1S,2R,3S)-1-(cyclohexylmethyl)-3-cyclopropyl-2,3-dihydroxypropyl]imidazole-4-propionamide and N-[(RS)-3-quinuclidinyl]-3-phenyl-L-alanine (Peptides, Proc. 11th Am. Pept. Sym. 1989, editors J. E. Rivier and G. R. Marshall p. 411) the (S)-N-[(1S,2R,3S)-1-(cyclohexylmethyl)-3-cyclopropyl-2,3-dihydroxypropyl-α-[(S)-[[(RS)-3-quinuclidinyl]amino]hydrocinnamamido]imidazole-4-propionamide as a colourless solid, MS: 621 (M+H)$^+$;

from (S)-α-amino-N-[(1S,2R,3S)-1-(cyclohexylmethyl)-3-cyclopropyl-2,3-dihydroxypropyl]imidazole-4-propionamide and (RS)-α-[4-[1-(benzyloxy)formamido]-4-methyl-2-oxopentyl]hydrocinnamic acid the benzyl [(R or S)-5-[[(S)-1-[[(1S,2R,3S)-1-(cyclohexylmethyl)-3-cyclopropyl-2,3-dihydroxypropyl]carbamoyl]2-imidazol-4-ylethyl]carbamoyl]-1,1-dimethyl-3-oxo-6-phenylhexyl]carbamate, MS: 744 (M+H)$^+$, and its more polar epimer benzyl [(S or R)-5-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-1,1-dimethyl-3-oxo-6-phenylhexyl]carbamate, MS: 744 (M+H)$^+$, each as a colourless solid.

The (RS)-α-[4-[1-(benzyloxy)formamido]-4-methyl-2-oxopentyl]hydrocinnamic acid used as the starting material was prepared as follows:

(RS)-α-[4-[1-(Benzyloxy)formamido]-4-methyl-2-oxopentyl]hydrocinnamic acid was obtained as a colourless foam, MS: 398 (M+H)$^+$, from N-[(benzyloxy)carbonyl]-3,3-dimethyl-β-alanine (EPA 0230266) and diethyl benzylmalonate analogously to the general method for the preparation of N-protected dipeptide ketoisoesters described in J. Med. Chem. 32, 1378 (1989).

The 3-(p-methoxyphenyl)-L-alanine derivatives used as the starting materials were prepared as follows:

N-[3-[1-(Benzyloxy)formamido]-3-methylbutyryl]-3-(p-methoxyphenyl)-L-alanine (a) N-[3-[1-(Benzyloxy)formamido]-3-methylbutyryl]-3-(p-methoxyphenyl)-L-alanine methyl ester A suspension of 1.12 g (4.47 mmol) of N-[(benzyloxy)carbonyl]-2,3-dimethyl-β-alanine (EPA 0230266), 1.1 g (4.47 mmol) of 3-(p-methoxyphenyl)-L-alanine methyl ester hydrochloride, 1.7 g (4.47 mmol) of HBTU and 1.25 ml (8.94 mmol) of triethylamine in 40 ml of acetonitrile is stirred at room temperature for 4 hours. After the addition of 50 ml of saturated sodium chloride solution the mixture is extracted 3 times with 50 ml of ethyl acetate each time. The combined organic phases are washed in sequence with 2N hydrochloric acid, water, 50% sodium hydrogen carbonate solution and water, dried over sodium sulphate and evaporated under reduced pressure. For purification, the residue is chromatographed on silica gel using a 95:5 mixture of methylene chloride and methanol as the eluent. N-[3-[1-(Benzyloxy)formamido]-3-methylbutyryl]-3-(p-methoxyphenyl)-L-alanine methyl ester is obtained as a colourless oil; MS: 443 (M+H)$^+$.

(b) N-[3-[1-(Benzyloxy)formamido]-3-methylbutyryl]-3-(p-methoxyphenyl)-L-alanine 0.184 g (4.39 mmol) of lithium hydroxide hydrate dissolved in 8 ml of water is added dropwise to a solution of 1.7 g (3.84 mmol) of N-[3-[1-(benzyloxy)formamido]-3-methylbutyryl]-3-(p-methoxyphenyl)-L-alanine methyl ester in 16 ml of dioxan. The solution is stirred at 0° for 1 hour, then treated with 20 ml of water and extracted twice with ether. The aqueous phase is acidified with 6N hydrochloric acid and extracted twice with ether. The combined ether extracts are washed with saturated sodium chloride solution, dried over sodium sulphate and then evaporated under reduced pressure. N-[3-[1-(Benzyloxy)formamido]-3-methylbutyryl]-3-(p-methoxyphenyl)-L-alanine is obtained as a colourless oil, MS: 429 (M+H)⁺.

The following compounds were prepared in an analogous manner to that described for the preparation of N-[3-[1-(benzyloxy)formamido]-3-methylbutyryl]-3-(p-methoxyphenyl)-L-alanine:

N-[3-[1-(Benzyloxy)formamido]propionyl]-3-(p-methoxyphenyl)-L-alanine as a colourless solid, MS: 401 (M+H)⁺, by the condensation of N-benzyloxycarbonyl-β-alanine and 3-(p-methoxyphenyl)-L-alanine methyl ester hydrochloride and subsequent basic hydrolysis;

N-[6-[1-(benzyloxy)formamido]hexanoyl]-3-(p-methoxyphenyl)-L-alanine as a colourless solid, MS: 443 (M+H)⁺, by the condensation of 6-[1-(benzyloxy)formamido]hexanoic acid (EPA 0229667) and 3-(p-methoxyphenyl)-L-alanine methyl ester hydrochloride and subsequent basic hydrolysis;

N-[[p-[1-(benzyloxy)formamido]phenyl]acetyl]-3-(p-methoxyphenyl)-L-alanine as a colourless solid, MS: 463 (M+H)⁺, by the condensation of [p-[1-(benzyloxy)formamido]phenyl]acetic acid [Chem. Ber. 101, 1223 (1968)] and 3-(p-methoxyphenyl)-L-alanine methyl ester hydrochloride and subsequent basic hydrolysis;

N-[[cis/trans-4-[1-(benzyloxy)formamido]cyclohexyl]acetyl]-3-(p-methoxyphenyl)-L-alanine as a colourless solid, MS: 469 (M+H)⁺, by the condensation of cis/trans-4-[1-(benzyloxy)formamido]cyclohexaneacetic acid (Izv. Akad. Nauk, SSSR, Set. Khim. 1980, 1426) and 3-(p-methoxyphenyl)-L-alanine methyl ester hydrochloride and subsequent basic hydrolysis;

N-[(S)-4-[1-(benzyloxy)formamido]-2-hydroxybutyryl]-3-(p-methoxyphenyl)-L-alanine as a colourless solid, MS: 431 (M+H)⁺, by the condensation of (S)-4-[1-(benzyloxy)formamido]-2-hydroxybutyric acid [Carbohydrate Res. 28, 263 (1973)] and 3-(p-methoxyphenyl)-L-alanine methyl ester hydrochloride and subsequent basic hydrolysis;

N-(3-hydroxy-3-methylbutyryl)-3-(p-methoxyphenyl)-L-alanine as a colourless oil, MS: 296 (M+H)⁺, by the condensation of β-hydroxyvaleric acid and 3-(p-methoxyphenyl)-L-alanine methyl ester hydrochloride and subsequent basic hydrolysis;

3-(p-methoxyphenyl)-N-[3-methyl-3-(4-morpholinecarboxamido)-3-methylbutyryl]-L-alanine as a colourless foam, MS: 408 (M+H)⁺, by the condensation of 3-(4-morpholinecarboxamido)-3-methylbutyric acid and 3-(p-methoxyphenyl)-L-alanine methyl ester hydrochloride and subsequent basic hydrolysis;

N-[[1-[1-(Benzyloxy)formamido]cyclopropyl]acetyl]-3-(p-methoxyphenyl)-L-alanine as a colourless solid, MS: 427 (M+H)⁺, by the condensation of 1-[1-(benzyloxy)formamido]cyclopropaneacetic acid and 3-(p-methoxyphenyl)-L-alanine methyl ester hydrochloride and subsequent basic hydrolysis.

The 3-(4-morpholinecarboxamido)-3-methylbutyric acid used as the starting material was prepared analogously to the procedure described in EPA 0230266 for the preparation of N-[(benzyloxy)carbonyl]-3,3-dimethyl-β-alanine by using morpholine in place of benzyl alcohol.

The 1-[1-(benzyloxy)formamido]cyclopropaneacetic acid used as the starting material was synthesized analogously to the procedure described in EPA 0230266 for the preparation of N-[(benzyloxy)carbonyl]-3,3-dimethyl-β-alanine by using 1-carboxycyclopropaneacetic acid (Bull. Soc. Chim. Fr. 1971, 2290) in place of 2,2-dimethyl-succinic acid.

EXAMPLE 52

In an analogous manner to that described in Example 21, by replacing Boc-D-proline by N-benzyloxycarbonyl-D-alanine in the condensation with (S)-N-[(1S,2R,3S)-1-(cyclohexylmethyl)-3-cyclopropyl-2,3-dihydroxypropyl]-α-[(3-phenyl-L-alanyl)amino]imidazole-4-propionamide there was obtained benzyl [(R)-1-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl]carbamoyl]ethyl]carbamate as an amorphous solid, MS: 717 (M+H)⁺.

EXAMPLE 53

In an analogous manner to that described in Example 19, by condensing (S)-α-amino-N-[(1S,2R,3S)-1-(cyclohexylmethyl)-3-cyclopropyl-2,3-dihydroxypropyl]-imidazole-4-propionamide and N-Boc-p-methoxy-L-phenylalanine there was obtained tert-butyl [(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-p-methoxyphenethyl]carbamate as a colourless solid, MS: 642 (M+H)⁺. Subsequent cleavage of the Boc protecting group using hydrochloric acid in methanol analogously to Example 18b) yielded (S)-α-[(S)-α-amino-p-methoxyhydrocinnamamido]-N-[(1S,2R,3S)-1-(cyclohexylmethyl)-3-cyclopropyl-2,3-dihydroxypropyl] imidazole-4-propionamide hydrochloride as a colourless solid, MS: 542 (M+H)⁺. Further condensation with N-benzyloxycarbonyl-L-adipic acid α-methyl ester [J. Org. Chem. 52, 5342 (1987)] analogously to Example 19 gave benzyl [(S)-4-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-p-methoxyphenethyl]carbamoyl]-1-(methoxycarbonyl)butyl]carbamate as an amorphous solid, MS: 833 (M)⁺.

EXAMPLE 54

The following compounds were manufactured in an analogous manner to that described in Example 1:

From (S)-α-amino-N-[(1S,2R,3S)-1-(cyclohexylmethyl)-3-cyclopropyl-2,3-dihydroxypropyl]imidazole-4-propionamide and (S)-α-[(phenylsulphonyl)methyl] hydrocinnamic acid (EPA 0236734) the (S)-N-[(1S,2R,3S)-1-(cyclohexylmethyl)-3-cyclopropyl-2,3-dihydroxypropyl]-α-[(S)-α-[(phenylsulphonyl)methyl] hydrocinnamamido]imidazole-4-propionamide as an amorphous solid, MS: 651 (M+H)⁺;

from (S)-α-amino-N-[(1S,2R,3S)-1-(cyclohexylmethyl)-3-cyclopropyl-2,3-dihydroxypropyl]imidazole-4-propionamide and (S)-α-[tert-butylsulphonyl)methyl]-3-thiophenepropionic acid the (S)-α-[(S)-α-[tert-butylsulphonyl)methyl]-3-thiophenepropionamido]-N-[(1S,2R, 3S)-1-(cyclohexylmethyl)-3-cyclopropyl-2,3-dihydroxypropyl]imidazole-4-propionamide as a colourless foam, MS: 637 (M+H)⁺;

from (S)-α-amino-N-[(1S,2R,3S)-1-(cyclohexylmethyl)-3-cyclopropyl-2,3-dihydroxypropyl]imidazole-4-propionamide and (S)-α-[[(cyclopropylmethyl)sulphonyl]methyl]hydrocinnamic acid the (S)-N-[(1S,2R,3S)-1-(cyclohexylmethyl)-3-cyclopropyl-2,3-dihydroxypropyl]-α-[(S)-α-[[(cyclopropylmethyl)sulphonyl]methyl]hydrocinnamamido]imidazole-4-propionamide as a colourless foam, MS: 629 (M+H)⁺;

from (R)-2-amino-N-[(1S,2R,3S)-1-(cyclohexylmethyl)-3-cyclopropyl-2,3-dihydroxypropyl]-3-(methylthio) propionamide and (S)-α-[(tert-butylsulphonyl)methyl] hydrocinnamic acid (EPA 0236734) the (S)-α-[(tert-butylsulphonyl)methyl]-N-[(R)-1-[[(1S,2R,3S)-1-(cyclohexylmethyl)-3-cyclopropyl-2,3- dihydroxypropyl]carbamoyl]-2-(methylthio)ethyl] hydrocinnamamide as an amorphous solid, MS: 611 (M+H)⁺.

The (R)-2-amino-N-[(1S,2R,3S)-1-(cyclohexylmethyl)-3-cyclopropyl-2,3-dihydroxypropyl]-3-(methylthio) propionamide used as the starting material was prepared as follows:

tert-Butyl [(R)-1-[[(1S,2R,3S)-1-(cyclohexylmethyl)-3-cyclopropyl-2,3-dihydroxypropyl]carbamoyl]-2-(methylthio)ethyl]carbamate was obtained as an amorphous solid, MS: 445 (M+H)⁺, by condensing (R)-Boc-(S-methyl) cysteine (J. Chem. Soc. C 1967, 2632) and (1S,2R,3S)-3-amino-4-cyclohexyl-1-cyclopropyl-1,2-butanediol in an analogous manner to that described in Example 1g). Subsequent cleavage of the Boc protecting group using hydrochloric acid in methanol yielded (R)-2-amino-N-[(1S,2R,3S)-1-(cyclohexylmethyl)-3-cyclopropyl-2,3-dihydroxypropyl]-3-(methylthio)propionamide.

The acid derivatives used as the starting materials were prepared as follows:

(S)-α-[(tert-Butylsulphonyl)methyl]-3-thiophenepropionic acid

This compound was prepared analogously to Example 1 by the enzymatic hydrolysis of ethyl (RS)-α-[(tert-butylsulphonyl)methyl]-3-thiophenepropionate which, in turn, was prepared starting from diethyl 3-thienylmethylmalonate [J. Am. Chem. Soc. 76, 4466 (1954)] analogously to the synthesis of ethyl (RS)-α-[(tert-butylsulphonyl)methyl]hydrocinnamate described in EPA 0236734, MS: 318 (M)⁺.

(S)-α-[[(Cyclopropylmethyl)sulphonyl]methyl] hydrocinnamic acid

This compound was prepared analogously to Example 1d) by the enzymatic hydrolysis of ethyl (RS)-α-[[(cyclopropylmethyl)sulphonyl]methyl]hydrocinnamate which, in turn, was prepared analogously to the synthesis of ethyl (RS)-α-[(tert-butylsulphonyl)methyl]hydrocinnamate described in EPA 0236734 by replacing tert-butylthiol by cyclopropylmethylthiol, MS: 282 (M)⁺.

EXAMPLE 55

The following compounds were manufactured in an analogous manner to that described in Example 4:

From (S)-1-(tert-butoxycarbonyl)-α-[(S)-α-[(tert-butylsulphonyl)methyl]hydrocinnamamido]imidazole-4-propionic acid and rac-ribo-3-amino-1-cyclopropyl-4-[(cyclopropylmethyl)thio]-1,2-butanediol the (S)-α-[(S)-α-[(tert-butylsulphonyl)methyl] hydrocinnamamido]-N-[(1R,2R,3S)-3-cyclopropyl-1-[[(cyclopropylmethyl)thio]methyl]-2,3-dihydroxypropyl]-1-Boc-imidazole-4-propionamide and the (S)-α-[(S)-α-[(tert-butylsulphonyl)methyl] hydrocinnamamido]-N-[(1S,2S,3R)-3-cyclopropyl-1-[[(cyclopropylmethyl)thio]methyl]-2,3-dihydroxypropyl]-1-Boc-imidazole-4-propionamide.

The rac-ribo-3-amino-1-cyclopropyl-4-[(cyclopropylmethyl)thio]-1,2-butanediol used as the starting material was prepared analogously to the procedure which is described in WO 87/05302 for the synthesis of tert-butyl (4S,5R)-4-(cyclohexylmethyl)-5-formyl-2,2-dimethyl-3-oxazolidinecarboxylate starting from Boc-cyclohexylalanine methyl ester followed by the Grignard reaction with cyclopropylmagnesium bromide and cleavage of the Boc and isopropylidene protecting groups analogously to Example 1f). Replacement of the Boc-cyclohexylalanine methyl ester gave, starting from tert-butyl rac-[2-[(cyclopropylmethyl)thio]-1-(ethoxycarbonyl)ethyl]carbamate, rac-ribo-3-amino-1-cyclopropyl-4-[(cyclopropylmethyl)thio]-1,2-butanediol as a colourless solid, MS: 232 (M+H)⁺.

The tert-butyl rac-[2-[(cyclopropylmethyl)thio]-1-(ethoxycarbonyl)ethyl]carbamate used as the starting material was prepared as follows:

14.7 g (59 mmol) of N-Boc-L-cysteine ethyl ester dissolved in 300 ml of dimethylformamide are added dropwise at 0° to a suspension of 2.49 g (64.8 mmol) of sodium hydride (60% in oil) in 200 ml of dimethylformamide and the mixture is stirred at 0° for 30 minutes. Subsequently, 8.37 g (62 mmol) of bromomethylcyclopropane in 30 ml of dimethylformamide are added dropwise thereto. The solution is stirred at room temperature overnight. The dimethylformamide is evaporated under reduced pressure, the residue is partitioned between ether and water and the aqueous phase is extracted 4 times with ether. The combined organic phases are washed twice with water and twice with saturated sodium chloride solution, dried over sodium sulphate and evaporated under reduced pressure. For purification, the residue is chromatographed on silica gel using a 1:19 mixture of ethyl acetate and hexane as the eluent. There are obtained 8.4 g of tert-butyl rac-[2-[(cyclopropylmethyl)thio]-1-(ethoxycarbonyl)ethyl] carbamate as a colourless oil, MS: 304 (M+H)⁺.

EXAMPLE 56

The following compounds were manufactured in an analogous manner to that described in Example 4:

From (S)-1-(tert-butoxycarbonyl)-α-[(S)-α-[(tert-butylsulphonyl)methyl]hydrocinnamamido]imidazole-4-propionic acid and (1R or S,2S or R,3R,4S)-4-amino-5-cyclohexyl-1-cyclopropyl-1,2,3-pentanetriol the (S)-α-[(S)-α-[(tert-butylsulphonyl)methyl] hydrocinnamamido]-N-[(1S,2R,3S or R,4R or S)-1-(cyclohexylmethyl)-4-cyclopropyl-2,3,4-trihydroxybutyl]-1-Boc-imidazole-4-propionamide;

from (S)-1-(tert-butoxycarbonyl)-α-[(S)-α-[(tert-butylsulphonyl)methyl]hydrocinnamamido]imidazole-4-propionic acid and (1S or R,2S or R,3R,4S)-4-amino-5-cyclohexyl-1-cyclopropyl-1,2,3-pentanetriol the (S)-α-[(S)-α-[(tert-butylsulphonyl)methyl] hydrocinnamamido]-N-[(1S,2R,3S or R,4S or R)-1-(cyclohexylmethyl)-4-cyclopropyl-2,3,4-trihydroxybutyl]-1-Boc-imidazole-4-propionamide;

from (S)-1-(tert-butoxycarbonyl)-α-[(S)-α-[(tert-butylsulphonyl)methyl]hydrocinnamamido]imidazole-4-propionic acid and (1R or S,2R or S,3R,4S)-4-amino-5-cyclohexyl-1-cyclopropyl-1,2,3-pentanetriol the (S)-α-[(S)-α-[(tert-butylsulphonyl)methyl] hydrocinnamamido]-N-[(1S,2R,3R or S,4R or S)-1-(cyclohexylmethyl)-4-cyclopropyl-2,3,4-trihydroxybutyl]-1-Boc-imidazole-4-propionamide;

from (S)-1-(tert-butoxycarbonyl)-α-[(S)-α-[(tert-butylsulphonyl)methyl]hydrocinnamamido]imidazole-4-propionic acid and (1S or R,2R or S,3R,4S)-4-amino-5-cyclohexyl-1-cyclopropyl-1,2,3-pentanetriol the (S)-α-[(S)-α-[(tert-butylsulphonyl)methyl] hydrocinnamamido]-N-[(1S,2R,3R or S,4S or R)-1-(cyclohexylmethyl)-4-cyclopropyl-2,3,4-trihydroxybutyl]-1-Boc-imidazole-4-propionamide.

The 4-amino-5-cyclohexyl-1-cyclopropyl-1,2,3-pentanetriols used as the starting materials were prepared as follows:

(a) tert-Butyl (4S,5R)-4-(cyclohexylmethyl)-5-[(S or R)-cyanohydroxymethyl]-2,2-dimethyl-3- oxazolidinecarboxylate and tert-butyl (4S,5R)-4-(cyclohexylmethyl)-5-[(R or S)-cyanohydroxymethyl]-2,2-dimethyl-3-oxazolidinecarboxylate:

A solution of 1.14 g (5 mmol) of tetraethyl orthotitanate in 5 ml of tetrahydrofuran is added to a solution of 325.4 mg (1 mmol) of tert-butyl (4S,5R)-4-(cyclohexylmethyl)-5-formyl-2,2-dimethyl-3-oxazolidinecarboxylate (WO 87/05302) in 10 ml of tetrahydrofuran. After stirring for 30 minutes there are added 20 mg of potassium-cyanide/18-crown-6 complex followed by a solution of 0.25 ml (2 mmol) of trimethylsilyl cyanide in 5 ml of tetrahydrofuran. The reaction has finished after 60 minutes. The reaction mixture is poured into a saturated ammonium chloride solution, extracted 3 times with ethyl acetate and the combined organic phases are washed with saturated sodium chloride solution, dried over magnesium sulphate and evaporated under reduced pressure. For purification, the crude product is chromatographed on 50 g of silica gel using a 3:2 mixture of hexane and ether as the eluent. The material obtained is recrystallized twice from ether/hexane. There is thus obtained tert-butyl (4S,5R)-4-(cyclohexylmethyl)-5-[(S or R)-cyanohydroxymethyl]-2,2-dimethyl-3-oxazolidinecarboxylate as colourless crystals, MS: 353 (M+H)$^+$, while tert-butyl (4S,5R)-4-(cyclohexyl-methyl)-5-[(R or S)-cyanohydroxymethyl]-2,2-dimethyl-3-oxazolidinecarboxylate is present in enriched form in the mother liquor.

(b) tert-Butyl (4S,5R)-4-(cyclohexylmethyl)-5-[(R or S)-cyclopropylcarbonyl)hydroxymethyl]-2,2-dimethyl-3-oxazolidinecarboxylate and tert-butyl (4S,5R)-4-(cyclohexylmethyl)-5-[(S or R)-(cyclopropylcarbonyl]hydroxymethyl-2,2-dimethyl-3-oxazolidinecarboxylate:

A solution of 2.64 g (7.5 mmol) of tert-butyl (4S,5R)-4-(cyclohexylmethyl)-5-[(S or R)-cyanohydroxymethyl]-2,2-dimethyl-3-oxazolidinecarboxylate and tert-butyl (4S,5R)-4-(cyclohexylmethyl)-5-[(R or S)-cyanohydroxymethyl]-2,2-dimethyl-3-oxazolidinecarboxylate in 30 ml of ether is added dropwise at 40° within 20 minutes to a Grignard reagent prepared in the usual manner from 3.3 ml (41.2 mmol) of cyclopropylbromide and 1.0 g (41.2 gram atom) of magnesium in 35 ml of ether. After removing the oil bath the reaction mixture is stirred at room temperature for 2 hours. Subsequently, the mixture is acidified at 0° with 35 ml of aqueous citric acid and stirred for 1 hour while cooling with ice. Thereafter, the mixture is extracted with ether, the organic phase is washed with 2N sodium hydrogen carbonate solution, dried over magnesium sulphate and evaporated under reduced pressure. For purification, the residue is chromatographed on 450 g of silica gel using a 4:1 and 7:3 mixture of hexane and ether as the eluent. There are obtained 500 mg of tert-butyl (4S,5R)-4-(cyclohexylmethyl)-5-[(R or S)-(cyclopropylcarbonyl)hydroxymethyl]-2,2-dimethyl-3-oxazolidinecarboxylate as a colourless solid, MS: 396 (M+H)$^+$, and 850 mg of tert-butyl (4S 5R)-4-(cyclohexylmethyl)-5-[(S or R)-(cyclopropylcarbonyl) hydroxymethyl]-2,2-dimethyl-3-oxazolidinecarboxylate as a colourless foam, MS: 396 (M+H)$^+$.

(c) tert-butyl (4S,5R)-4-(cyclohexylmethyl)-5-[(1S or R,2S or R)-2-cyclopropyl-1,2-dihydroxyethyl]-2,2-dimethyl-3-oxazolidinecarboxylate and tert-butyl (4S,5R)-4-(cyclohexylmethyl)-5-[(1S or R,2R or S)-2-cyclopropyl-1,2-dihydroxyethyl]-2,2-dimethyl-3-oxazolidinecarboxylate:

0.3 ml (5.16 mmol) of acetic acid is added to a solution of 340 mg (0.86 mmol) of tert-butyl (4S,5R)-4-(cyclohexylmethyl)-5-[(R or S)-(cyclopropylcarbonyl) hydroxymethyl]-2,2-dimethyl-3-oxazolidinecarboxylate in 15 ml of methylene chloride, the mixture is cooled to 0° and treated with 65 mg (1.72 mmol) of sodium borohydride. The reaction mixture is stirred at 0° for 5 hours. Thereafter, 6.5 ml of a 2N sodium hydrogen carbonate solution are added dropwise and the reaction mixture is taken up in methylene chloride. The organic phase is washed with water, dried over magnesium sulphate and evaporated under reduced pressure. For purification, the residue is chromatographed on 60 g of silica gel using a 4:1 mixture of toluene and ethyl acetate as the eluent. There are obtained 90 mg of tert-butyl (4S,5R)-4-(cyclohexylmethyl)-5-[(1S or R,2S or R)-2-cyclopropyl-1,2-dihydroxyethyl]-2,2-dimethyl-3-oxazolidinecarboxylate as a colourless solid, MS: 398 (M+H)$^+$, and 247 mg of tert-butyl (4S,5R)-4-(cyclohexylmethyl)-5-[(1S or R,2R or S)-2-cyclopropyl-1,2-dihydroxyethyl]-2,2-dimethyl-3-oxazolidinecarboxylate as a colourless solid, MS: 398 (M+H)$^+$.

In an analogous manner to that described above, from tert-butyl (4S,5R)-4-(cyclohexylmethyl)-5-[(S or R)-(cyclopropylcarbonyl)hydroxymethyl]-2,2-dimethyl-3-oxazolidinecarboxylate there were obtained tert-butyl (4S, 5R)-4-(cyclohexylmethyl)-5-[(1R or S,2S or R)-2-cyclopropyl-1,2-dihydroxyethyl]-2,2-dimethyl-3-oxazolidinecarboxylate as a colourless solid, MS: 398 (M+H)$^+$, and tert-butyl (4S 5R)-4-(cyclohexylmethyl)-5-[(1R or S,2R or S)-2-cyclopropyl-1,2-dihydroxyethyl]-2,2-dimethyl-3-oxazolidinecarboxylate as a colourless solid, MS: 398 (M+H)$^+$.

(d) (1R or S,2S or R,3R,4S)-4-Amino-5-cyclohexyl-1-cyclopropyl-1,2,3-pentanetriol:

90 mg (0.2 mmol) of tert-butyl (4S,5R)-4-(cyclohexylmethyl)-5-[(1S or R,2R or S)-2-cyclopropyl-1, 2-dihydroxyethyl]-1,2-dimethyl-3-oxazolidinecarboxylate are left to stand at room temperature for 3 days in 5 ml of 0.3N methanolic hydrochloric acid. Thereafter, the mixture is evaporated to dryness under reduced pressure. For purification, the residue is chromatographed on 25 g of silica gel using a 65:10:1 mixture of methylene chloride, methanol and ammonia as the eluent. There are obtained 46 mg of (1R or S,2S or R,3R,4S)-4-amino-5-cyclohexyl-1-cyclopropyl-1,2,3-pentanetriol as a colourless solid, MS: 258 (M+H)$^+$.

The following amines were obtained in an analogous manner:

From tert-butyl (4S,5R)-4-(cyclohexylmethyl)-5-[(1S or R,2S or R)-2-cyclopropyl-1,2-dihydroxyethyl]-2,2-dimethyl-3-oxazolidinecarboxylate the (1S or R,2S or R,3R,4S)-4-amino-5-cyclohexyl-1-cyclopropyl-1,2,3-pentanetriol as a colourless solid, MS: 258 (M+H)$^+$;

from tert-butyl (4S,5R)-4-(cyclohexylmethyl)-5-[(1R or S,2S or R)-2-cyclopropyl-1,2-dihydroxyethyl]-2,2-dimethyl-3-oxazolidinecarboxylate the (1S or R,2R or S,3R,4S)-4-amino-5-cyclohexyl-1-cyclopropyl-1,2,3-pentanetriol as a colourless solid, MS: 258 (M+H)$^+$;

from tert-butyl (4S,5R)-4-(cyclohexylmethyl)-5-[(1R or S,2R or S)-2-cyclopropyl-1,2-dihydroxyethyl]-2,2-dimethyl-3-oxazolidinecarboxylate the (1R or S,2R or S,3R,4S)-4-amino-5-cyclohexyl-1-cyclopropyl-1,2,3-pentanetriol as a colourless solid, MS: 258 (M+H)$^+$.

EXAMPLE 57

The following compounds were manufactured in an analogous manner to that described in Example 10:

From (S)-α-[(S)-α-[(tert-butylsulphonyl)methyl] hydrocinnamamido]-N-[(1R,2R,3S)-3-cyclopropyl-1-[[(cyclopropylmethyl)thio]methyl]-2,3-dihydroxypropyl]-1-Boc-imidazole-4-propionamide the (S)-α-[(S)-α-[(tert-butylsulphonyl)methyl]
hydrocinnamamido]-N-[(1R,2R,3S)-3-cyclopropyl-1-
[[(cyclopropylmethyl)thio]methyl]-2,3-
dihydroxypropyl]imidazole-4-propionamide as a
colourless solid, MS: 635 (M+H)$^+$;

from (S)-α-[(S)-α-[(tert-butylsulphonyl)methyl]
hydrocinnamamido]-N-[(1S,2S,3R)-3-cyclopropyl-1-
[[(cyclopropylmethyl)thio]methyl]-2,3-
dihydroxypropyl]-1-Boc-imidazole-4-propionamide
the (S)-α-[(S)-α-[(tert-butylsulphonyl)methyl]
hydrocinnamamido]-N-[(1S,2S,3R)-3-cyclopropyl-1-
[[(cyclopropylmethyl)thio]methyl]-2,3-
dihydroxypropyl]imidazole-4-propionamide as a
colourless solid, MS: 635 (M+H)$^+$.

EXAMPLE 58

The following compounds were manufactured in an analogous manner to that described in Example 10:

From (S)-α-[(S)-α-[(tert-butylsulphonyl)methyl]
hydrocinnamamido]-N-[(1S,2R,3S or R,4R or S)-1-
(cyclohexylmethyl)-4-cyclopropyl-2,3,4-
trihydroxybutyl]-1-Boc-imidazole-4-propionamide the
(S)-α-[(S)-α-[(tert-butylsulphonyl)methyl]
hydrocinnamamido]-N-[(1S,2R,3S or R,4R or S)-1-
(cyclohexylmethyl)-4-cyclopropyl-2,3,4-
trihydroxybutyl]imidazole-4-propionamide as a
colourless solid, MS: 661 (M+H)$^+$;

from (S)-α-[(S)-α-[(tert-butylsulphonyl)methyl]
hydrocinnamamido]-N-[(1S,2R,3S or R,4S or R)-1-
(cyclohexylmethyl)-4-cyclopropyl-2,3,4-
trihydroxybutyl]-1-Boc-imidazole-4-propionamide the
(S)-α-[(S)-α-[(tert-butylsulphonyl)methyl]
hydrocinnamamido]-N-[(1S,2R,3S or R,4S or R)-1-
(cyclohexylmethyl)-4-cyclopropyl-2,3,4-
trihydroxybutyl]imidazole-4-propionamide as a
colourless solid, MS: 661 (M+H)$^+$;

from (S)-α-[(S)-α-[(tert-butylsulphonyl)methyl]
hydrocinnamamido]-N-[(1S,2R,3R or S,4R or S)-1-
(cyclohexylmethyl)-4-cyclopropyl-2,3,4-
trihydroxybutyl]-1-Boc-imidazole-4-propionamide the
(S)-α-[(S)-α-[(tert-butylsulphonyl)methyl]
hydrocinnamamido]-N-[(1S,2R,3R or S,4R or S)-1-
(cyclohexylmethyl)-4-cyclopropyl-2,3,4-
trihydroxybutyl]imidazole-4-propionamide as a
colourless solid, MS: 661 (M+H)$^+$;

from (S)-α-[(S)-α-[(tert-butylsulphonyl)methyl]
hydrocinnamamido]-N-[(1S,2R,3R or S,4S or R)-1-
(cyclohexylmethyl)-4-cyclopropyl-2,3,4-
trihydroxybutyl]-1-Boc-imidazole-4-propionamide the
(S)-α-[(S)-α-[(tert-butylsulphonyl)methyl]
hydrocinnamamido]-N-[(1S,2R,3R or S,4S or R)-1-
(cyclohexylmethyl)-4-cyclopropyl-2,3,4-
trihydroxybutyl]imidazole-4-propionamide as a
colourless solid, MS: 661 (M+H)$^+$.

EXAMPLE 59

The following compounds were manufactured in an analogous manner to that described in Example 31:

From N-[(S)-1-[[(1S,2R,3S)-1-(cyclohexylmethyl)-3-
cyclopropyl-2,3-dihydroxypropyl]carbamoyl]-2-(1-
tritylimidazol)-4-ylethyl]-5-fluoroindole-2-
carboxamide the N-[(S)-1-[[(1S,2R,3S)-1-
(cyclohexylmethyl)-3-cyclopropyl-2,3-
dihydroxypropyl]carbamoyl]-2-imidazol-4-ylethyl]-5-
fluoroindole-2-carboxamide as an amorphous solid,
MS: 526 (M+H)$^+$;

from N-[(S)-1-[[(1S,2R,3S)-1-(cyclohexylmethyl)-3-
cyclopropyl-2,3-dihydroxypropyl]carbamoyl]-2-(1-
tritylimidazol)-4-ylethyl]-5-methylindole-2-
carboxamide the N-[(S)-1-[[(1S,2R,3S)-1-
(cyclohexylmethyl)-3-cyclopropyl-2,3-
dihydroxypropyl]carbamoyl]-2-imidazol-4-ylethyl]-5-
methylindole-2-carboxamide as an amorphous solid,
MS: 522 (M+H)$^+$;

from N-[(S)-1-[[(1S,2R,3S)-1-(cyclohexylmethyl)-3-
cyclopropyl-2,3-dihydroxypropyl]carbamoyl]-2-(1-
tritylimidazol)-4-ylethyl]-5-methoxyindole-2-
carboxamide the N-[(S)-1-[[(1S,2R,3S)-1-
(cyclohexylmethyl)-3-cyclopropyl-2,3-
dihydroxypropyl]carbamoyl]-2-imidazol-4-ylethyl]-5-
methoxyindole-2-carboxamide as an amorphous solid,
MS: 538 (M+H)$^+$;

from 3-chloro-N-[(S)-1-[[(1S,2R,3S)-1-
(cyclohexylmethyl)-3-cyclopropyl-2,3-
dihydroxypropyl]carbamoyl]-2-(1-tritylimidazol)-4-
ylethyl]indole-2-carboxamide the 3-chloro-N-[(S)-1-[[
(1S,2R,3S)-1-(cyclohexylmethyl)-3-cyclopropyl-2,3-
dihydroxypropyl]carbamoyl]-2-imidazol-4-ylethyl]
indole-2-carboxamide as an amorphous solid, MS: 542
(M+H)$^+$;

from 3,6-dichloro-N-[(S)-1-[[(1S,2R,3S)-1-
(cyclohexylmethyl)-3-cyclopropyl-2,3-
dihydroxypropyl]carbamoyl]-2-(1-tritylimidazol)-4-
ylethyl]indole-2-carboxamide the 3,6-dichloro-N-[(S)-
1-[[(1S,2R,3S)-1-(cyclohexylmethyl)-3-cyclopropyl-2,
3-dihydroxypropyl]carbamoyl]-2-imidazol-4-ylethyl]]
indole-2-carboxamide as an amorphous solid, MS: 576
(M+H)$^+$;

from (S)-α-benzothiazolecarboxamido-N-[(1S,2R,3S)-1-
(cyclohexylmethyl)-3-cyclopropyl-2,3-
dihydroxypropyl]-1-tritylimidazole-4-propionamide
the (S)-α-benzothiazolecarboxamido-N-[(1S,2R,3S)-
1-(cyclohexylmethyl)-3-cyclopropyl-2,3-
dihydroxypropyl]imidazole-4-propionamide as an
amorphous solid, MS: 526 (M+H)$^+$;

from N-[(S)-1-[[(1S,2R,3S)-1-(cyclohexylmethyl)-3-
cyclopropyl-2,3-dihydroxypropyl]carbamoyl]-2-(1-
tritylimidazol)-4-ylethyl]-2-quinolinecarboxamide the
N-[(S)-1-[[(1S,2R,3S)-1-(cyclohexylmethyl)-3-
cyclopropyl-2,3-dihydroxypropyl]carbamoyl]-2-
imidazol- 4-ylethyl]-2-quinolinecarboxamide as an
amorphous solid, MS: 611 (M+H)$^+$;

from (S)-α-[(RS)-1,4-benzodioxane-2-carboxamido]-N-
[(1S,2R,3S)-1-(cyclohexylmethyl)-3-cyclopropyl-2,3-
dihydroxypropyl]-1-tritylimidazole-4-propionamide
the (S)-α-[(RS)-1,4-benzodioxane-2-carboxamido]-N-
[(1S,2R,3S)-1-(cyclohexylmethyl)-3-cyclopropyl-2,3-
dihydroxypropyl]imidazole-4-propionamide as an
amorphous solid, MS: 527 (M+H)$^+$;

from tert-butyl [(RS)-1-[[(S)-1-[[[(1S,2R,3S)-1-
(cyclohexylmethyl)-3-cyclopropyl-2,3-
dihydroxypropyl]carbamoyl]-2-(1-tritylimidazol)-4-
ylethyl]carbamoyl]-2-(3-pyridyl)ethyl]carbamate the
tert-butyl [(RS)-1-[[(S)-1-[[(1S,2R,3S)-1-
(cyclohexylmethyl)-3-cyclopropyl-2,3-
dihydroxypropyl]carbamoyl]-2-imidazol-4-ylethyl]
carbamoyl]-2-(3-pyridyl)ethyl]carbamate as an
amorphous solid, MS: 613 (M+H)$^+$.

EXAMPLE 60

The following compounds were manufactured by catalytic hydrogenation in an analogous manner to that described in Example 34:

From benzyl [(R or S)-5-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-1,1-dimethyl-3-oxo-6-phenylhexyl]carbamate the (S)-α-[(R or S)-α-(4-amino-4-methyl-2-oxopentyl)hydrocinnamamido]-N-[(1S,2R,3S)-1-(cyclohexylmethyl)-3-cyclopropyl-2,3-dihydroxypropyl]imidazole-4-propionamide diacetate as a colourless solid, MS: 610 (M+H)⁺;

from benzyl [(S or R)-5-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-1,1-dimethyl-3-oxo-6-phenylhexyl]carbamate the (S)-α-[(S or R)-α-(4-amino-4-methyl-2-oxopentyl)hydrocinnamamido]-N-[(1S,2R,3S)-1-(cyclohexylmethyl)-3-cyclopropyl-2,3-dihydroxypropyl]imidazole-4-propionamide diacetate as a colourless solid, MS: 610 (M+H)⁺;

from benzyl cis/trans-4-[[[(S)-α-1-[[(1S,2R,3S)-1-(cyclohexylmethyl)-3-cyclopropyl-2,3-dihydroxypropyl]carbamoyl-2-imidazol-4-ylethyl]carbamoyl]-p-methoxyphenethyl]carbamoyl]methyl]cyclohexanecarbamate the (S)-α-[(S)-α-[2-(p-aminophenyl)acetamido]-p-methoxyhydrocinnamamido]-N-[(1S,2R,3S)-1-(cyclohexylmethyl)-3-cyclopropyl-2,3-dihydroxypropyl]imidazole-4-propionamide diacetate as a colourless, amorphous powder, MS: 675 (M+H)⁺;

from benzyl [(S)-3-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-p-methoxyphenethyl]carbamoyl]-2-hydroxyethyl]carbamate the (S)-α-[(S)-α-[(S)-4-amino-2-hydroxybutyramido]-p-methoxyhydrocinnamamido]-N-(1S,2R,3S)-1-(cyclohexylmethyl)-3-cyclopropyl-2,3-dihydroxypropyl]imidazole-4-propionamide diacetate as a colourless, amorphous powder, MS: 643 (M+H)⁺;

from benzyl [(S)-4-[[(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-p-methoxyphenethyl]carbamoyl]-1-(methoxycarbonyl)butyl]carbamate the methyl (S)-2-amino-5-[[(S)-α-[[(S)-1-[[(1S,-2R,3S)-1-(cyclohexylmethyl)-3-cyclopropyl-2,3-dihydroxypropyl]carbamoyl]-2-imidazol-4-ylethyl]carbamoyl]-p-methoxyphenethyl]carbamoyl]valerate diacetate as a colourless, amorphous powder, MS: 643 (M+H)⁺.

EXAMPLE 61

In an analogous manner to that described in Example 18b) from tert.butyl [2-[[(S)-α-[[(R)-1-[[(1S,2R,3S)-1-(cyclohexylmethyl)-3-cyclopropyl-2,3-dihydroxypropyl]carbamoyl-2-(methylthio)ethyl]carbamoyl]-p-methoxyphenethyl]carbamoyl]-1,1-dimethyl]carbamate there was obtained by cleaving off the Boc protecting group using hydrochloric acid in methanol the (S)-α-(3-amino-3-methylbutyramido)-N-[(S)-1-[[(1S,2R,3S)-1-(cyclohexylmethyl)-3-cyclopropyl-2,3-dihydroxypropyl]carbamoyl]-2-(methylthio)ethyl]-p-methoxyhydrocinnamamide as a colourless solid, MS: 621 (M+H)⁺.

EXAMPLE 62

A sterile filtered aqueous solution of (S)-α-[(S)-α-[(tert-butylsulphonyl)methyl]hydrocinnamamido]-N-[(1S,2R)-1-(cyclohexylmethyl)-2-[(R or S)-3-cyclopropyl-2-oxo-5-oxazolidinyl]-2-hydroxyethyl]imidazole-4-propionamide is mixed while warming with a sterile gelatine solution, which contains phenol as a preserving agent, under aseptic conditions so that 1.0 ml of solution has the following composition:

(S)-α-[(S)-α-[(tert-Butylsulphonyl)-methyl]hydrocinnamamido]-N-[(1S,2R)-1-(cyclohexylmethyl)-2-[(R or S)-3-cyclopropyl-2-oxo-5-oxazolidinyl]-2-hydroxyethyl]imidazole-4-propionamide 3.0 mg Gelatine 150.0 mg Phenol 4.7 mg Dist. water ad 1.0 ml The mixture is filled into 1.0 ml vials under aseptic conditions.

EXAMPLE 63

5 mg of (S)-α-[(S)-α-[(tert-butylsulphonyl)methyl]hydrocinnamamido]-N-[(1S,2R)-1-(cyclohexylmethyl)-2-[(R or S)-3-cyclopropyl-2-oxo-5-oxazolidinyl]-2-hydroxyethyl]imidazole-4-propionamide are dissolved in 1 ml of an aqueous solution with 20 mg of mannitol. The solution is filtered sterile and filled under aseptic conditions into a 2 ml ampoule, cooled to a low temperature and lyophilized. Prior to administration the lyophilizate is dissolved in 1 ml of distilled water or 1 ml of physiological saline. The solution is used intramuscularly or intravenously. This formulation can also be filled into double chamber injection ampoules.

EXAMPLE 64

500 mg of finely milled (5.0 μm) (S)-α-[(S)-α-[(tert-butylsulphonyl)methyl]hydrocinnamamido]-N-[(1S,2R)-1-(cyclohexylmethyl)-2-[(R or S)-3-cyclopropyl-2-oxo-5-oxazolidinyl]-2-hydroxyethyl]imidazole-4-propionamide are suspended in a mixture of 3.5 ml of Myglyol 812 and 0.08 g of benzyl alcohol. This suspension is filled into a container having a dosage valve. 5.0 g of Freon 12 are filled into the container through the valve under pressure. The Freon is dissolved in the Myglyol-benzyl alcohol mixture by shaking. This spray container contains about 100 single doses which can be applied individually.

EXAMPLE 65

When the procedures described in Examples 62–64 are followed, corresponding galenical preparations can be manufactured from the following, likewise preferred, compounds:

(S)-α-[(S)-α-[[[(2-Amino-1,1-dimethylethyl)sulphonyl]methyl]hydrocinnamamido]-N-[(1S,2R,3S)-1-(cyclohexylmethyl)-3-cyclopropyl-2,3-dihydroxypropyl]imidazole-4-propionamide dihydrochloride, (S)-α-[(S)-α-[[(2-amino-2-methylpropyl)sulphonyl]methyl]hydrocinnamamido]-N-[(1S,2R,3S)-1-(cyclohexylmethyl)-3-cyclopropyl-2,3-dihydroxypropyl]imidazole-4-propionamide diacetate, (S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl 1-piperidinecarboxylate, (S)-α-[(S)-α-[(tert-butylsulphonyl)methyl]hydrocinnamamido]-N-[(1S,2R,3S)-1-(cyclohexylmethyl)-3-cyclopropyl-3-fluoro-2-hydroxypropyl]imidazole-4-propionamide and N-[(S)-1-[[(1S,2R,3S)-1-(cyclohexylmethyl)-3-cyclopropyl-2,3-dihydroxypropyl]carbamoyl]-2-imidazol-4-ylethyl]indole-2-carboxamide.

We claim:

1. A compound of the formula:

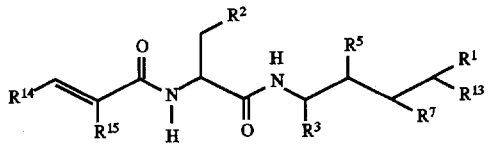

wherein:

$R^2$ is imidazol-4-yl, $R^3$ is cyclohexylmethyl or 4,4-difluorocyclohexylmethyl, $R^5$ and $R^7$ each are hydroxy or aminomethylcarbonyloxy, $R^{12}$ and $R^{13}$ together with the carbon atom to which they are attached are cyclopropyl or cyclobutyl, $R^{14}$ is phenyl and $R^{15}$ is $C_1$–$C_4$-alkylcarbonylmethyl, heterocycloalkylcarbonylmethyl, substituted aminocarbonylmethyl, $C_1$–$C_4$alkylsulphonylmethyl, $C_3$–$C_6$-cycloalkylsulphonylmethyl, $C_3$–$C_6$-cycloalkyl-$C_1$–$C_4$-alkylsulphonylmethyl, substituted amino-$C_1$–$C_4$-alkylcarbonylmethyl, heterocycloalkylcarbonyloxy, amino-$C_1$–$C_4$-alkylsulphonylmethyl or substituted amino-$C_1$–$C_4$-alkylsulphonylmethyl.

2. The compound of claim 1 wherein said compound is (S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl-1-piperidinecarboxylate.

3. The compound of claim 1 wherein said compound is(S)-α-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]phenethyl-4-morpholinecarboxylate.

4. The compound of claim 1 wherein said compound is (S)-N-[(1S,2R,3S)-1-(cyclohexylmethyl)-3-cyclopropyl-2,3-dihydroxypropyl]-α-[(S)-α-[[(cyclopropylmethyl)sulphonyl]methyl]hydrocinnamamido]imidazole-4-propionamide.

5. The compound of claim 1 wherein said compound is (S)-α-[(S)-α-[[[(2-Amino-1,1-dimethylethyl)sulphonyl]methyl]hydrocinnamamido]-N-[(1S,2R,3S)-1-(cyclohexylmethyl)-3-cyclopropyl-2,3-dihydroxypropyl]imidazole-4-propionamide dihydrochloride.

6. (S)-α-[(S)-α-[(tert-Butylsulphonyl)methyl]hydrocinnamamido]-N-[(1S,2R,3S)-1-(cyclohexylmethyl)-3-cyclopropyl-2,3-dihydroxypropyl]-5-cyanoimidazole-4-propionamide.

7. The compound of claim 1 wherein said compound is (S)-α-[(S)-α-[(tert-Butylsulphonyl)methyl]hydrocinnamamido]-N-[(1S,2R,3S)-3-cyclopropyl-1-[(4,4-difluorocyclohexyl)methyl]-2,3-dihydroxypropyl]imidazole-4-propionamide.

8. (S)-α-[(S)-α-[(tert-Butylsulphonyl)methyl]hydrocinnamamido]-N-[(1S,2R,3S)-3-cyclopropyl-1-(p-fluorobenzyl)-2,3-dihydroxypropyl]imidazole-4-propionamide.

9. The compound of claim 1 wherein said compound is (S)-α-[(S)-α-[[(2-Amino-2-methylpropyl)sulphonyl]methyl]hydrocinnamamido]-N-[(1S,2R,3S)-1-(cyclohexylmethyl)-3-cyclopropyl-2,3-dihydroxypropyl]imidazole-4-propionamide diacetate.

10. (S)-N-[(1S,2R,3S)-3-Azido-1-(cyclohexylmethyl)-3-cyclopropyl-2-hydroxypropyl]-α-[(S)-α-(tert-butylsulphonyl)methyl]-hydrocinnamamido]imidazole-4-propionamide.

11. (S)-α-[(S)-α-[(tert-butylsulphonyl)methyl]hydrocinnamamido]-N-[(1S,2R)-1-(cyclohexylmethyl)-2-[(R or S)-3-cyclopropyl-2-oxo-5-oxazolidinyl]-2-hydroxyethyl]-imidazole-4-propionamide.

12. (S)-α-[(S)-α-[(tert-butylsulphonyl)methyl]hydrocinnamamido]-N-[(1S,2R,3S)-1-(cyclohexylmethyl)-3-cyclopropyl-3-fluoro-2-hydroxypropyl]imidazole-4-propionamide.

13. (S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropanesulphonic acid guanidine salt.

14. N-[(S)-1-[[(1S,2R,3S)-1-(cyclohexylmethyl)-3-cyclopropyl-2,3-dihydroxypropyl]carbamoyl]-2-imidazol-4-ylethyl]-indole-2-carboxamide.

15. (S)-N-[(1S,2R,3S)-1-(cyclohexylmethyl)-3-cyclopropyl-2,3-dihydroxy-propyl]-α-(2,2-dibenzylacetamido)imidazole-4-propionamide.

16. N-[(S)-1-[[(1S,2R,3S)-1-(cyclohexylmethyl)-3-cyclopropyl-2,3-dihydroxypropyl]carbamoyl]-2-imidazol-4-ylethyl]-2-benzimidazolecarboxamide.

17. (1R,2S)-1-[(S)-1--(5)-1-acetyl-α-(S)-α-[(tert-butylsulphonyl)methyl]imidazole-4-propionamido]-2-cyclohexylethyl]-2-cyclopropylethylene diacetate.

18. (1S,2R,3S)-3-[(S)-α-[(S)-α-[(tert-butylsulphonyl)methyl]hydrocinnamamido]imidazole-4-propionamido]-4-cyclohexyl-1-cyclopropyl-2-hydroxybutyl o-aminobenzoate.

19. (1R,2S)-1-[(S)-1-[(S)-α-[(S)-α-[(tert-butylsulphonyl)methyl]hydrocinnamamido]imidazole-4-propionamido]-2-cyclohexylethyl]-2-cyclopropylethylene dicyclopropane carboxylate.

20. Ethyl 4-[(S)-2-[(S)-α-[(tert-butylsulphonyl)methyl]hydrocinnamamido]-2-[[(1S,2R,3S)-1-(cyclohexylmethyl)-3-cyclopropyl-2,3-dihydroxypropyl]carbamoyl]ethyl]imidazole-1-carboxylate.

* * * * *